United States Patent [19]
Muzyczka et al.

[11] Patent Number: 6,020,192
[45] Date of Patent: *Feb. 1, 2000

[54] HUMANIZED GREEN FLUORESCENT PROTEIN GENES AND METHODS

[75] Inventors: Nicholas Muzyczka; Sergei Zolotukhin; William Hauswirth, all of Gainesville, Fla.

[73] Assignee: University of Florida, Gainesville, Fla.

[*] Notice: This patent is subject to a terminal disclaimer.

[21] Appl. No.: 08/893,327

[22] Filed: Jul. 16, 1997

Related U.S. Application Data

[63] Continuation-in-part of application No. 08/588,201, Jan. 18, 1997.

[51] Int. Cl.$^7$ ............................ C12N 15/63; C07H 21/04
[52] U.S. Cl. .................................... 435/320.1; 435/235.1; 536/23.1; 536/23.5
[58] Field of Search ..................... 425/6, 172.3, 173.3, 425/235.1, 325, 320.1; 536/23.1

[56] References Cited

U.S. PATENT DOCUMENTS 5,625,048   4/1997   Tsien et al. ............................. 536/24.5

FOREIGN PATENT DOCUMENTS

WO97/26333   7/1997   WIPO .

OTHER PUBLICATIONS

Carey, "Evidence using a green fluorescent protein–glucocorticoid receptor chimera that the RAN/TC4 GTPhase mediates an essential function independent of nuclear protein import," *J. Cell Biol.*, 133(5):985–996, 1996.

De Giorgi et al., "Targeting aequorin and green fluorescent protein to intracellular organelles," *Gene*, 173:113–117, 1996.

Picard and Yamamoto, "Two signals mediate hormone–dependent nuclear localization of the glucocordicoid receptor," *EMBOJ.*, 6(11):3333–3340, 1987.

Rizzuto et al., "Double labelling of subcellular structures with organelle–targeted GFP mutants in vivo," *Curr. Biol.*, 6(2):183–188, 1996.

Delagrave et al., Red–shifted excitation mutants of the green fluorescent protein, Bio/Technology, vol. 13, pp. 151–154, Feb. 1995.

Grantham et al., Codon catalog usage and the genome hypothesis, Nucleic Acids Research, vol. 8 (1), pp. r49–r62, 1980.

Wada et al., Codon usage tabulated from the Genbank genetic sequence data, Nucleic Acids Research, vol. 18 (suppl), pp. 2367–2411, 1990.

Cubitt et al., Understanding, improving and using green fluorescent proteins, TIBS, vol. 20, pp. 448–455, Nov. 1995.

Goodman et al., Recombinant adeno–associated virus mediated gene transfer into hematopoietic progenitor cells, Blood, vol. 84 (5), pp. 1492–1500, Sep. 1, 1994.

*Primary Examiner*—Nancy Degen
*Assistant Examiner*—Andrew Wang
*Attorney, Agent, or Firm*—Arnold, White & Durkee

[57] ABSTRACT

Disclosed are synthetic and "humanized" versions of green fluorescent protein (GFP) genes adapted for high level expression in mammalian cells, especially those of human origin. Base substitutions are made in various codons in order to change the codon usage to one more appropriate for expression in mammalian cells. Recombinant vectors carrying such humanized genes are also disclosed. In addition, various methods for using the efficient expression of humanized GFP in mammalian cells and in animals are described.

11 Claims, 22 Drawing Sheets

```
       1   2   3   4   5   6   7   8   9  10  11  12  13  14  15  16  17  18  19  20
       M   S   K   G   E   E   L   F   T   G   V   V   P   I   L   V   E   L   D   G
      ATG AGT AAA GGA GAA GAA CTT TTC ACT GGA GTT GTC CCA ATT CTT GTT GAA TTA GAT GGT
               C   G   C   G       G           C   G                   C   G       C
                                                                                    G 21  22  23  24  25  26  27  28  29  30  31  32  33  34  35  36  37  38  39  40
       D   V   N   G   H   K   F   S   V   S   G   E   G   E   G   D   A   T   Y   G
      GAT GTT AAT GGG CAC AAA TTT TCT GTC AGT GGA GAG GGT GAA GGT GAT GCA ACA TAC GGA
       G                           C                                           C 41  42  43  44  45  46  47  48  49  50  51  52  53  54  55  56  57  58  59  60
       K   L   T   L   K   F   I   C   T   T   G   K   L   P   V   P   W   P   T   L
      AAA CTT ACC CTT AAA TTT ATT TGC ACT ACT GGA AAA CTA CCT GTT CCA TGG CCA ACA CTT
       G   C       C   C   C       C               G   C           G
                                                                                    G
                                                       ─────────────── EaeI ───

61  62  63  64  65  66  67  68  69  70  71  72  73  74  75  76  77  78  79  80
       V   T   T   F  S/T Y/H  G   V   Q   C   F   S   R   Y   P   D   H   M   K   Q
      GTC ACT ACT TTC TCT TAT GGT GTT CAA TGC TTT TCA AGA TAC CCA GAT CAT ATG AAA CAG
       G   C   C       ACC  C   G                   C                   C           G
```

FIG. 1A

```
                                        100                                    120                                           140                                     160
         H   D   F   F   K   S   A   M   P   E   G   Y   V   Q   E   R   T   I   F   F
         CAT GAC TTT TTC AAG AGT GCC ATG CCC GAA GGT TAT GTA CAG GAA AGA ACT ATA TTT TTC
                             C       G   C               G           G               C   C
                                     90                                    110
         K   D   D   G   N   Y   K   T   R   A   E   V   K   F   E   G   D   T   L   V
         AAA GAT GAC GGG AAC TAC AAG ACA CGT GCT GAA GTC AAG TTT GAA GGT GAT ACC CTT GTT
                                             C   C                       G          C EcoRII G   G
                                                                          130
         N   R   I   E   L   K   G   I   D   F   K   E   D   G   N   I   L   G   H   K
         AAT AGA ATC GAG TTA AAA GGT ATT GAT TTT AAA GAA GAT GGA AAC ATT CTT GGA CAC AAA
                         G   G   C                       G           C       C           G
                                                                          150
         L   E   Y   N   Y   N   S   H   N   V   Y   I   M   A   D   K   Q   K   N   G
         TTG GAA TAC AAC TAT AAC TCA CAC AAT GTA TAC ATC ATG GCA GAC AAA CAA AAG AAT GGA
         C                                   G                   C       G                   C
```

```
     I   K   V   N   F   K   I   R   H   N   I   E   D   G   S   V   Q   L   A   D
                                            170                 180
    ATC AAA GTT AAC TTC AAA ATT AGA CAC AAC ATT GAA GAT GGA AGC GTT CAA CTA GCA GAC
         G       C           G   C                       G       C       G   G   C
                                                          ─────BamHI─────

H   Y   Q   Q   N   T   P   I   G   D   G   P   V   L   L   P   D   N   H   Y
                                            190                 200
    CAT TAT CAA CAA AAT ACT CCA ATT GGC GAT GGC CCT GTC CTT TTA CCA GAC AAC CAT TAC
                 G   C                   C           G   C   C

L   S   T   Q   S   A   L   S   K   D   P   N   E   K   R   D   H   M   V   L
                                            210                 220
    CTG TCC ACA CAA TCT GCC CTT TCG AAA GAT CCC AAC GAA AAG AGA GAC CAC ATG GTC CTT
                 C   G           T                                   C           G
                 ──────────────────

L   E   F   V   T   A   A   G   I   T   H   G   M   D   E   L   Y   K
                                            230       238
    CTT GAG TTT GTA ACA GCT GCT GGG ATT ACA CAT GGC ATG GAT GAA CTA TAC AAA TAA
     G           G           C                   C       C       G   C       G G
```

HUMANIZED GREEN FLUORESCENT PROTEIN GENES AND METHODS

This application is a continuation-in-part of United States patent application number 08/588,201 filed Jan. 18, 1997.

BACKGROUND OF THE INVENTION

1. Field of the Invention

The present invention relates generally to the field of reporter genes and particularly provides improved green fluorescent protein (GFP) genes, constructs and methods of use. The gfp genes disclosed herein are humanized gfp genes adapted for expression in mammalian and human cells by using preferred DNA codons.

2. Description of the Related Art

Reporter molecules are frequently used in biological systems to monitor gene expression. Commonly used reporter genes include β-galactosidase, firefly luciferase, alkaline phosphatase, chloramphenicol acetyltransferase (CAT) and β-glucuronidase (GUS). However, the available reporter genes have certain drawbacks that limit their use. A frequently encountered limitation is that the introduction of a substrate is required. Other drawbacks include, for example, the size of certain proteins which means that expression of reporter-fusion proteins can be difficult.

Another useful strategy is to label a protein with a fluorescent tag to enable subsequent detection and localization in intact cells. Fluorescent labeling is used in conjunction with immunofluorescence and fluorescence analog cytochemistry, in which the biochemistry and trafficking of proteins are monitored after microinjection into living cells.

Fluorescence labeling has generally been achieved by purifying proteins and covalently conjugating them to reactive derivatives of organic fluorophores. In these methods, the stoichiometry and locations of dye attachment are often difficult to control and careful repurification of the proteins is usually necessary. A further problem is introducing the labeled proteins into a cell, which often involve microinjection techniques or methods of reversible permeabilization to introduce the proteins through the plasma membrane.

A molecular biological alternative to fluorescent-tagged proteins has been made possible by recent advances and the cloning of green fluorescent protein (GFP). The green fluorescent protein (GFP) encoded by the gfp10 gene from the jellyfish *Aequorea victoria* is a protein of 238 amino acids which absorbs blue light (major peak at 395 nm) and emits green light (major peak at 509 nm) (Morin and Hastings, 1971; Ward et al., 1980; Prasher et al., 1992). The GFP hexapeptide chromophore starts at amino acid 64 and is derived from the primary amino acid sequence through the cyclization of serine-dehydrotyrosine-glycine within this hexapeptide (Shimomura, 1979; Cody et al., 1993).

The light-stimulated GFP fluorescence is species-independent and does not require any cofactors, substrates, or additional gene products from *A. victoria* (Chalfie et al., 1994). This allows GFP detection in living cells other than *A. victoria* so long as meaningful gene expression can be achieved. The small size of gfp10 and the "real-time" detection of the product thus makes GFP a promising candidate for use as a reporter gene.

Certain GFP variants have recently been reported that have improved spectral properties. For example, Heim et. al. (1994) described a mutant that fluoresces blue and contains a histidine in place of Tyr66. Heim et. al. (1995) later described a Ser65→Thr GFP mutant that has a spectrum much closer to that of *Renilla reniformis*, which has an extinction coefficient per monomer more than 10 times that of the longer-wavelength peak of Aequorea GFP.

However, despite certain developments, such as the variants described above, the present usefulness of GFP is still limited by variable and, at best, low expression levels in mammalian cells. Therefore, it is evident that new developments in GFP technology are needed before the full potential of this protein can be realized, particularly in applications that require expression in mammalian cells, including gene therapy strategies.

SUMMARY OF THE INVENTION

The present invention seeks to overcome these and other drawbacks inherent in the prior art by providing humanized green fluorescent protein (GFP) genes adapted for expression in mammalian and human cells. The humanized gfp genes of the invention are prepared by incorporating codons preferred for use in human genes into the DNA sequence. Also provided are humanized gfp expression constructs and various methods of using the humanized genes and vectors.

Accordingly, the present invention provides humanized green fluorescent protein (GFP) genes and methods of making and using such genes. As used herein the term a "humanized green fluorescent protein (GFP) gene" means a gene that has been adapted for expression in mammalian and human cells by replacing at least one, and preferably, more than one, and most preferably, a significant number, of jellyfish gfp codons with one or more codons that are more frequently used in human genes.

The humanized genes of the invention are preferably cDNAs, although genomic copies are by no means excluded. The humanized genes are also preferably humanized versions adapted from the *A. victoria* gfp gene, although other gfp gene sources are, again, not excluded.

In certain embodiments, the present invention provides humanized gfp genes that encode a green fluorescent protein that has the amino acid sequence of SEQ ID NO:2.

In other embodiments, humanized gfp genes will encode GFP variants that are generally based upon the foregoing sequence, but that have certain changes. A particular example is a humanized gene that encodes a GFP with an amino acid sequence of SEQ ID NO:2 in which Serine at position 65 has been replaced by Threonine.

A further example is a humanized gfp gene that encodes a green fluorescent protein that has the amino acid sequence of SEQ ID NO:2 in which Tyrosine at position 66 has been replaced by Histidine.

Another example is a humanized gfp gene that encodes a GFP that has the amino acid sequence of SEQ ID NO:2 in which the chromophore sequence Phe Ser Tyr Gly Val Gln (SEQ ID NO:4) between positions 64 and 69 has been replaced by the sequence Met Gly Tyr Gly Val Leu (SEQ ID NO:5).

Structural equivalents of the humanized gfp genes are also included within the present invention. However, mutants that are truncated by more than one amino acid residue at the amino terminus or more than about 10 or 15 amino acid residues from the carboxyl terminus are not generally considered to be useful in the context of producing a fluorescent protein. The encoded GFP should therefore be a minimum of about 222 amino acids in length, with proteins of about 238 amino acids in length generally being preferred.

The humanized genes of the present invention are also definable by genes in which at least about 10% of said codon positions contain a humanized codon. That is, they contain a codon that is preferentially used in human genes in place of a codon that is not so frequently used in human genes.

In other embodiments, the humanized genes will have at least about 15%, about 20%, about 25%, about 30% or about 35% of the codon positions defined by the presence of a humanized codon.

Humanized gfp genes wherein at least about 50% or above of the codon positions contain a humanized codon are also contemplated.

Preferred humanized gfp genes of the invention are those genes that contain certain key changes. Examples are genes that comprises at least seven humanized codons from the 10 codons located at codon positions 18, 53, 93, 125, 150, 178, 195, 208, 236 and 224 of the jellyfish gfp sequence.

Preferably, humanized gfp genes will comprise at least eight, at least nine, or ten, humanized codons from the 10 codons located at codon positions 18, 53, 93, 125, 150, 178, 195, 208, 236 and 224 of the jellyfish gfp gene sequence.

Such constructs are exemplified by humanized genes that comprise any one of the humanized Leucine codons CTG, CTC or TTG at codon positions 18, 53, 125, 178, 195 and 236 of the GFP gene sequence. A further example is a humanized gfp gene that comprises the humanized Valine codon GTG at codon positions 93, 150 and 224 of the GFP gene sequence. Other examples are humanized genes that comprise the humanized Serine codon TCT at codon position 208 of the GFP gene sequence.

The humanized gfp genes encompassed by this invention also include those genes that comprises an increased number of GCC or GCT Alanine-encoding codons in comparison to the wild type jellyfish gene sequence of SEQ ID NO: 1.

By the phrase "increased number of codons in comparison to the wild type jellyfish gene sequence of SEQ ID NO: 1" is meant that the humanized sequence contain an increased number of codons encoding a particular amino acid within the GFP coding region that encodes the amino acid sequence of SEQ ID NO:2, or one of the mutants or other equivalents described herein, in comparison to those codons encoding the same amino acid that are present within the coding region of the wild type jellyfish gene sequence of SEQ ID NO:1. Thus it will be understood that the term "increased", when used in this context, does not mean the addition of one or more codons to a terminal portion of the coding region, but rather means replacement of an unfavorable codon within the coding region with a codon that is more favorable for translation in a human or mammalian cell.

In light of the definition set forth above, the humanized gfp genes of the invention may also be defined as those genes that comprise an increased number of TGC Cysteine-encoding codons; an increased number of GAC Aspartate-encoding codons; an increased number of GAG Glutamate-encoding codons; an increased number of TTC Phenylalanine-encoding codons; an increased number of GGC Glycine-encoding codons; an increased number of CAC Histidine-encoding codons; an increased number of ATC Isoleucine-encoding codons; an increased number of AAG Lysine-encoding codons; an increased number of CTG or CTC Leucine-encoding codons; an increased number of AAC Asparagine-encoding codons; an increased number of CCC or CCT Proline-encoding codons; an increased number of CAG Glutamine-encoding codons; an increased number of CGC, AGG or CGG Arginine-encoding codons; an increased number of AGC or TCC Serine-encoding codons; an increased number of ACC Threonine-encoding codons; an increased number of GTG or GTC Valine-encoding codons; and/or an increased number of TAC Tyrosine-encoding codons in comparison to the wild type jellyfish gene sequence of SEQ ID NO:1.

In certain embodiments, the humanized gfp genes may also comprise a TGA termination codon.

Humanized gfp genes may also be defined by comprising a decreased number of certain codons in comparison to the wild type jellyfish gene sequence of SEQ ID NO:1. "Decreased" in this context also means that the humanized sequence contain a decreased number of codons encoding a particular amino acid within the GFP coding region that encodes the amino acid sequence of SEQ ID NO:2, or a mutant or equivalent thereof, in comparison to those codons encoding the same amino acid that are present within the coding region of the wild type jellyfish gene sequence of SEQ ID NO:1. Thus it will be understood that "decreased" does not in any way reflect the simple deletion of codons from any portion of the coding region, but again refers to replacement of a jellyfish codon with a codon that occurs more frequently in human genes.

Accordingly, humanized gfp genes of the present invention are also be defined as those genes that comprise a decreased number of GCA Alanine-encoding codons; a decreased number of GGU Glycine-encoding codons; a decreased number of CTT, CTA or TTA Leucine-encoding codons; a decreased number of AGA Arginine-encoding codons; a decreased number of AGT, TCA or TCG Serine-encoding codons; or a decreased number of GTT or GTA Valine-encoding codons.

Although not believed to be required, it is currently preferred that the humanized gfp genes should include a Kozak consensus sequence operatively positioned upstream from the humanized gene sequence (i.e., the gene is positioned downstream from the Kozak consensus sequence).

Certain preferred humanized gfp genes will comprise the nucleic acid sequence of SEQ ID NO:3. However, this is by no means limiting and is just one exemplary embodiment of the present invention. Detailed directions as how to make and use many other such humanized gfp genes are included herein. For example, one may refer to the information in Table 2, Table 3 and Table 4 in creating any one of a number of suitable humanized gfp genes.

Genes humanized in the manner of the invention may also be operatively linked to other protein-encoding nucleic acid sequences. This will generally result in the production of a fusion protein following expression of such a nucleic acid construct. Both N-terminal and C-terminal fusion proteins are contemplated.

Virtually any protein- or peptide-encoding DNA sequence, or combinations thereof, may be fused to a humanized gfp sequence in order to encode a fusion protein. This includes DNA sequences that encode targeting peptides, therapeutic proteins, proteins for recombinant expression, proteins to which one or more targeting peptides is attached, protein subunits and the like.

Recombinant vectors and plasmids form another important aspect of the present invention. In such vectors, the humanized gfp gene is positioned under the transcriptional control of a promoter, generally a promoter operative in a mammalian or human cell. "Positioned under the transcriptional control of" means that the humanized gfp sequence is positioned downstream from and under the transcriptional control of the promoter such the promoter is capable of directing expression of the encoded GFP protein in a mammalian or human host cell upon introduction of the vector into such a cell.

The recombinant vectors of the invention will thus generally comprise a humanized gfp reporter gene operatively positioned downstream from a promoter, wherein the promoter is capable of directing expression of the humanized GFP gene in a mammalian or human cell. Preferably the promoter will direct expression of GFP in an amount sufficient to allow GFP detection by detecting the green fluorescence following expression of GFP in the cell. Such promoters are thus "operative" in mammalian and human cells.

Expression vectors and plasmids in accordance with the present invention may comprise one or more constitutive promoters, such as viral promoters or promoters from mammalian genes that are generally active in promoting transcription. Examples of constitutive viral promoters include the HSV, TK, RSV, SV40 and CMV promoters, of which the CMV promoter is a currently preferred example. Examples of constitutive mammalian promoters include various housekeeping gene promoters, as exemplified by the β actin promoter.

Inducible promoters and/or regulatory elements are also contemplated for use with the expression vectors of the invention. Examples of suitable inducible promoters include promoters from genes such as cytochrome P450 genes, heat shock protein genes, metallothionein genes, hormone-inducible genes, such as the estrogen gene promoter, and such like. Promoters that are activated in response to exposure to ionizing radiation, such as fos, jun and egr-1, are also contemplated. The tetVP16 promoter that is responsive to tetracycline is a currently preferred example.

Tissue-specific promoters and/or regulatory elements will be useful in certain embodiments. Examples of such promoters that may be used with the expression vectors of the invention include promoters from the liver fatty acid binding (FAB) protein gene, specific for colon epithelial cells; the insulin gene, specific for pancreatic cells; the transphyretin, α1-antitrypsin, plasminogen activator inhibitor type 1 (PAI-1), apolipoprotein AI and LDL receptor genes, specific for liver cells; the myelin basic protein (MBP) gene, specific for oligodendrocytes; the glial fibrillary acidic protein (GFAP) gene, specific for glial cells; OPSIN, specific for targeting to the eye; and the neural-specific enolase (NSE) promoter that is specific for nerve cells.

The construction and use of expression vectors and plasmids is well known to those of skill in the art. Virtually any mammalian cell expression vector may thus be used connection with the humanized genes disclosed herein.

Preferred vectors and plasmids will be constructed with at least one multiple cloning site. In certain embodiments, the expression vector will comprise a multiple cloning site that is operatively positioned between a promoter and a humanized gfp gene sequence. Such vectors may be used, in addition to their uses in other embodiments, to create N-terminal fusion proteins by cloning a second protein-encoding DNA segment into the multiple cloning site so that it is contiguous and in-frame with the humanized gfp sequence.

In other embodiments, expression vectors may comprise a multiple cloning site that is operatively positioned downstream from the expressible humanized gfp gene sequence. These vectors are useful, in addition to their uses, in creating C-terminal fusion proteins by cloning a second protein-encoding DNA segment into the multiple cloning site so that it is contiguous and in-frame with the humanized gfp sequence.

Vectors and plasmids in which a second protein- or RNA-encoding nucleic acid segment is also present are, of course, also encompassed by the invention, irrespective of the nature of the nucleic acid segment itself.

A second reporter gene may be included within an expression vector of the present invention. The second reporter gene may be comprised within a second transcriptional unit. Suitable second reporter genes include those that confer resistance to agents such as neomycin, hygromycin, puromycin, zeocin, mycophenolic acid, histidinol and methotrexate.

Expression vectors may also contain other nucleic acid sequences, such as IRES elements, polyadenylation signals, splice donor/splice acceptor signals, and the like.

Particular examples of suitable expression vectors are those adapted for expression using a recombinant adenoviral, recombinant adeno-associated viral (AAV) or recombinant retroviral system. Vaccinia virus, herpes simplex virus, cytomegalovirus, and defective hepatitis B viruses, amongst others, may also be used.

In certain embodiments, the expression vector or plasmid may comprise a humanized GFP reporter gene that has the nucleic acid sequence of SEQ ID NO:3.

Reporter gene expression kits are also provided, which kits generally comprise, in suitable container means, at least one expression vector or plasmid that comprises a humanized GFP gene. The vector or plasmid will generally be one that is capable of expressing GFP in an amount sufficient to allow GFP detection by green fluorescence following expression in a mammalian or human cell.

Recombinant host cells form another aspect of the present invention. Such host cells will generally comprise at least one copy of a humanized GFP gene. Preferred cells for expression purposes will be mammalian and human cells. However, it will understood that other cell types are not excluded from those of the invention. Accordingly, cells such as bacterial, yeast, fungal, insect, nematode and plant cells are also possible, although such cells are not preferred for expression purposes.

In certain embodiments, the recombinant host cells will preferably incorporate a humanized GFP gene in a manner effective to allow the cell to express, or to be stimulated to express, GFP, most preferably, in an amount sufficient to allow GFP detection by its fluorescence. The recombinant host cell will thus preferably include a humanized GFP gene that was introduced into the cell by means of a recombinant vector.

In certain embodiments, the recombinant host cell will express the humanized GFP gene to produce the encoded GFP protein, preferably, in an amount sufficient to allow GFP detection by its fluorescence. It is contemplated that cells containing as few as about 20 copies of a humanized gfp gene will often express the GFP protein in an amount sufficient to allow GFP detection by green fluorescence. In certain embodiments, cells containing as few as about 10 copies, about 5 copies or even about 1 or 2 copies of a humanized gfp gene will also likely satisfy the desired expression criteria, especially where the humanized gfp gene is a mutant gene. In other embodiments, the recombinant host cells may be capable of expressing a humanized gene in order to produce detectable GFP protein within a time frame of about 10 hours, and preferably within about 8 hours, and most preferably within about 6 hours or even less.

Examples of suitable recombinant host cells include VERO cells, HeLa cells, cells of Chinese hamster ovary (CHO) cell lines, COS cells, such as COS-7, and W138, BHK, HepG2, 3T3, RIN, MDCK, A549, PC12, K562 and 293 cells.

Cells of primary cell lines that have been established after removing cells from a mammal and culturing the cells for a limited period of time are also included within the cells of the present invention. These cells may be engineered by the hand of man and returned to the same host animal from which they were originally recovered. Such cells that contain a humanized gfp gene fall within the scope of the invention, irrespective of their location.

Naturally, recombinant cells also include those cells that are located within the body of an animal or human subject, as may have been targeted by gene therapy. These cells include all those that comprise at least one copy of a humanized gfp gene or vector, irrespective of the manner in which gene was acquired, e.g., by transfection, infection and the like.

In certain particular embodiments, recombinant host cells that comprise a humanized GFP gene that comprises the nucleic acid sequence of SEQ ID NO:3 are contemplated.

Many methods of using humanized gfp genes are provided by the present invention. The method of labeling or tagging a mammalian or human cell by expressing at least one humanized GFP gene in the cell is central to each of the methods. The humanized gfp gene should preferably produce GFP in an amount sufficient to allow ready detection of GFP in the cell by detecting GFP fluorescence.

Methods of identifying a mammalian or human cell within a population of cells are also provided. Such methods generally first comprise expressing at least one humanized GFP gene in the cell in a manner effective to produce an amount of GFP sufficient to allow GFP detection by fluorescence. The cell is then admixed, or allowed to become naturally admixed, with a population of cells that do not express GFP, following which the cell is identified by means of identifying a GFP-fluorescent cell.

The term "a GFP-fluorescent cell", as used herein, means that a cell expresses a humanized GFP gene in a manner effective to result in the production of the GFP product in an amount sufficient to allow subsequent detection of the cell by detecting green fluorescence from GFP in the cell.

The invention further provides methods for identifying a mammalian or human cell that contains an exogenous DNA segment, which methods generally first comprise introducing into a mammalian or human cell an expression vector comprising a humanized GFP gene operatively linked to an exogenous DNA segment. The cell is then preferably cultured under conditions and for a period of time effective to allow expression of the humanized gfp gene in order to produce an amount of GFP sufficient to allow GFP detection by green fluorescence. Subsequently identifying a cell that contains the exogenous DNA segment is then achieved by identifying a GFP-fluorescent cell.

These methods are suitable for identifying exogenous DNA segments that encode untranslated products, such as an antisense nucleic acid molecule, ribozyme or other RNA species; and also, for identifying exogenous DNA segments that encode translated products, such as selected proteins or peptides.

In certain such embodiments, the expression vector for use in such methods will comprise a first coding region defined as the humanized gfp gene that encodes GFP and will also comprise a second coding region that comprises the exogenous DNA segment. These vectors are generally known as vectors that comprises at least two transcriptional or translational units. Two transcriptional units will naturally include two promoters that direct expression of their respective downstream genes.

The methods of identifying mammalian or human cells that contain an exogenous DNA segment are also suitable for use with expression vectors that comprise a first coding region that encodes a fusion protein that comprises GFP operatively linked to a selected protein or peptide, with the vector expressing a fusion protein that comprises GFP operatively linked to the selected protein or peptide. These aspects of the invention are generally, although not necessarily exclusively, confined to the detection of exogenous DNA segments that encode translated products.

Fusion proteins that are expressed in such a manner may comprise GFP operatively linked to a peptide that comprises a sub-cellular localization signal, such as a nuclear targeting peptide or a mitochondrial targeting peptide. The fusion proteins may also comprise GFP operatively linked to both a selected protein and a peptide that comprises a sub-cellular localization signal.

Such identification methods may be carried out in vitro with a variety of aims in mind, as described below. These identification methods may also be carried out in vivo, wherein the cell is located within a mammal or human subject.

Two or more humanized gfp genes, each expressing a GFP protein with different spectral properties, may be detected in a cell in the manner described above. GFP-fluorescent cells, whether expressing one, two or more humanized gfp genes, may be identified by a variety of methods, including microscopy and fluorescence activated cell sorting (FACS).

Further examples of methods of the invention are methods for determining the location of a selected protein within a mammalian or human cell. These methods generally comprise first introducing into a cell an expression vector comprising a contiguous DNA sequence comprising a humanized GFP gene operatively linked to a gene encoding said selected protein. The vector will generally express a fusion protein comprising GFP operatively linked to the selected protein, wherein the fusion protein is produced in amounts sufficient to allow cell detection by detecting the green fluorescence of GFP. One can then identify the location of the selected protein within the cell by identifying the location of the green fluorescence from GFP.

These methods are suitable for determining the location of selected proteins within cells wherein the location is known or believed to be dependent upon external stimuli, such as, e.g., heat, cold, salt, or the presence of various agonists such as hormones, cytokines, neurotransmitters and the like. These methods are also suitable for determining the location of selected proteins within cells wherein the location is known or believed to be dependent upon internal signals, such as are present during changes in the cell cycle, during cell aging and apoptosis and the like.

Still further examples of methods of the invention are methods for targeting a protein to a selected location within a mammalian or human cell. These methods generally comprise first introducing into the cell an expression vector comprising a DNA sequence comprising a DNA sequence element that encodes a targeting peptide operatively linked and contiguous with a DNA sequence element of a humanized GFP gene, which is also operatively linked and contiguous with a DNA sequence element that encodes a protein. Such vectors express a fusion protein comprising a targeting peptide operatively linked to GFP and to a protein, wherein the fusion protein is produced in the cell in an amount sufficient to allow cell detection by detecting the GFP fluorescence. The protein is then targeted to a selected location within the cell and the location is confirmed by identifying the location of the green fluorescence.

Yet further examples of methods associated with this invention are methods for testing candidate promoters in mammalian or human cells.

These methods generally comprises introducing into a cell an expression vector comprising a humanized GFP gene under the control of the candidate promoter and maintaining the cell under conditions effective and for a period of time sufficient to allow expression of the humanized GFP gene by the candidate promoter. "Conditions effective" and "periods of time sufficient" are defined as those conditions and times that would ordinarily result in GFP being produced in an amount sufficient to allow GFP detection by green fluorescence when using a known operative promoter.

After maintaining the cell under the suitable conditions one would then identity any GFP-fluorescent cells, wherein the presence of GFP-fluorescent cells would be indicative of an active promoter in the expression construct within the identified cell.

These methods are suitable for analyzing candidate tissue-specific promoters, where the promoter may be tested in a range of mammalian or human cells; and for analyzing candidate inducible promoters, where the promoter is generally tested under a range of conditions. As used herein, the term "tissue-specific promoter" is used to refer to promoters that direct gene expression exclusively in certain tissues and promoters that direct gene expression preferentially in given tissues, which may also be termed "tissue-preferential" promoters. The candidate promoter may also be a promoter naturally associated with a candidate gene that is being tested for expression in a mammalian or human cell.

These methods are again suitable for analyzing promoters in vitro and in vivo, wherein in the latter case, the cell would be located within a mammal or human subject.

A further example of methods for using humanized gfp in the context of promoters are those methods for detecting substances that stimulate transcription from a selected promoter in a mammalian or human cell. Again, one generally introduces into a mammalian or human cell an expression vector comprising a humanized GFP gene under the control of a given promoter. One then exposes the cell to a composition suspected of containing a substance known or suspected to be capable of stimulating transcription from the given promoter. The cell is then cultured or maintained for a period of time that would ordinarily allow an active promoter to stimulate GFP-fusion protein production in an amount sufficient to allow cell detection by detecting the GFP-derived green fluorescence The subsequent identification of a GFP-fluorescent cell is then indicative of the original presence of a substance that stimulates transcription from the given promoter.

These methods are also suitable for use in vitro and in vivo. In vitro uses allow substances such as toxins and pollutants to detected by using appropriate promoters within the humanized gfp gene constructs.

As part of gene therapy, it is often necessary to determine gene expression levels in the treated mammalian animal or human subject. The present invention also provides methods for determining such the expression levels. These methods generally comprise expressing in cells of the animal an expression vector comprising a humanized GFP gene operatively linked to a selected gene. The expression vector will preferably be either a vector that expresses a GFP-fusion protein or a vector in which the humanized gfp gene and the selected protein gene each use the same or an equivalent promoter. The promoter will have preferably been shown to result in sufficient GFP expression to allow detection in vitro. One then determines the GFP-fluorescence in the cells of the animal, wherein the level of GFP-fluorescence is indicative of the expression level of the selected gene in the animal.

These methods can be adapted to provide methods for analyzing the expression of a selected gene in different tissues of a mammal or human subject. Such methods generally comprise introducing into the cells of the mammal an expression vector comprising the selected gene under the control of the natural gene promoter, wherein the gene is operatively linked to a humanized GFP gene. The vector will preferably express a fusion protein that comprises the encoded gene product operatively linked to GFP, the fusion protein being produced in an amount sufficient to allow cell detection by detecting the green fluorescence of GFP. After maintaining the mammal under conditions effective and for a period of time sufficient to allow expression of the gene one then analyzes the cells of the tissues of the mammal to detect GFP-fluorescent cells, wherein the presence of GFP-fluorescent cells in a given tissue is indicative of gene expression in the tissue.

A further example in which the humanized gfp genes may be employed is in the recombinant production of GFP itself. Such methods of using a humanized GFP gene simply comprise expressing the humanized gene in a mammalian or human host cell and collecting the GFP expressed by said cell.

These methods may be more fully described as comprising the steps of:

(a) preparing a recombinant vector in which a humanized GFP gene is positioned under the control of a promoter operative in a mammalian or human cell;

(b) introducing the recombinant vector into a mammalian or human host cell;

(c) culturing the host cell under conditions effective and for a period of time sufficient to allow expression of the encoded green fluorescent protein (GFP); and (d) collecting said expressed GFP and, preferably, purifying the GFP free from a significant amount of other cellular proteins.

Adaptations of such methods include those wherein the humanized GFP gene is fused to a DNA sequence encoding a protein or peptide of known molecular weight. Expression by the host cell thus results in a GFP fusion protein that may be used as a fluorescent molecular weight marker. A range of such fluorescent molecular weight markers could be so-produced to produce a molecular weight determining kit.

BRIEF DESCRIPTION OF THE DRAWINGS

The following drawings form part of the present specification and are included to furthers demonstrate certain aspects of the present invention. The invention may be better understood by reference to one or more of these drawings in combination with the detailed description of specific embodiments presented herein.

FIG. 1A, FIG. 1B and FIG. 1C. Nucleotide sequence of the gfp10 cDNA and the deduced amino acid sequence. Above each codon is the single letter designation for the amino acid. The mutations introduced in the $gfp_h$ sequence are shown below the substituted nucleotide of gfp10. The horizontal lines underline overlap regions of mutually priming oligonucleotides used to synthesize the $gfp_h$ cDNA. The sites of the restriction enzymes used to assemble extended pairs of oligonucleotides are shown in bold letters. The codons mutated to produce the $Ser_{65}Thr$ mutation, which produces higher fluorescence yield, and the $Tyr_{66}His$ mutation, which produces blue fluorescence, are shown in bold. In FIG. 1A, FIG. 1B and FIG. 1C the jellyfish gfp10 nucleotide sequence is SEQ ID NO:1. The deduced amino acid sequence is SEQ ID NO:2. In SEQ ID NO:2, Xaa at position 65 may be Ser or Thr; and Xaa at position 66 may be Tyr or His. The exemplary. humanized gfp sequence shown below the substituted nucleotide of gfp10 in FIG. 1A, FIG. 1B and FIG. 1C is SEQ ID NO:3. In SEQ ID NO:3, the nucleotides at positions 193, 195 and 196 may be changed in order to encode either Ser or Thr; and either Tyr or His, as above.

FIG. 2B-1, FIG. 2B-2 and FIG. 2B-3. Construction of pTR-UF general purpose vector.

FIG. 3. FACS analysis of 293 cells transfected with the $pTR_{BS}$-UF series of recombinant plasmids. 293 cells (6-well dish) were transfected with a total of 2.8 μg of DNA, consisting of different ratios of gfp-containing plasmid and sonicated salmon sperm carrier DNA, using the conventional calcium phosphate transfection protocol. Cells were harvested 36 hrs posttransfection and analyzed on the flow cytometer. Cells scored as positive were plotted on the graph as a function of the amount of gfp-carrying plasmid transfected. Clear bars correspond to the $pTR_{BS}$-UF, shaded bars to the $PTR_{BS}$-UF1, and black bars to the $pTR_{BS}$-UF2.

FIG. 4A, cells under phase contrast, light field; FIG. 4B, same field, epifluorescence.

FIG. 5A and FIG. 5C, G418-resistant colonies under phase contrast, light field; FIG. 5B and FIG. 5D, same fields as in FIG. 5A and FIG. 5C, epifluorescence.

FIG. 6A, the FACS histogramn plot of the parental 293 cell line; FIG. 6B, 293 cells transduced with rAAV-$GFP_J$; FIG. 6C, rAAV-$GFP_H1$; and FIG. 6D, rAAV-$GFP_H2$. In each case 20,000 cells were sorted. The uncorrected frequency of cells scored positive for each cell population was uninfected 293 cells: 0.05%; $GFP_J$: 0.05%; $GFP_H1$: 1.67%, $GFP_H2$: 9.6%.

FIG. 9A, differential interference contrast image of retina from an infected eye near the region shown on FIG. 9B. The darkly pigmented layer of cells near the top of the retina shown is the RPE layer in a slightly oblique section. The photoreceptor cell layer and other neuroretinal layers can be seen below the RPE. FIG. 9B, RPE layer from an rAAV-$GFP_H2$ inoculated eye near the injection site viewed under short wavelength excitation and fluorescein emission optics by confocal microscopy. FIG. 9C, fluorescence of the RPE layer from the same eye as in FIG. 9B at a site distal to the injection site. FIG. 9D, fluorescence of the RPE layer from the uninjected eye of the same animal as in FIG. 9A, FIG. 9B and FIG. 9C.

DETAILED DESCRIPTION OF THE PREFERRED EMBODIMENTS

Figures 1, 2A:
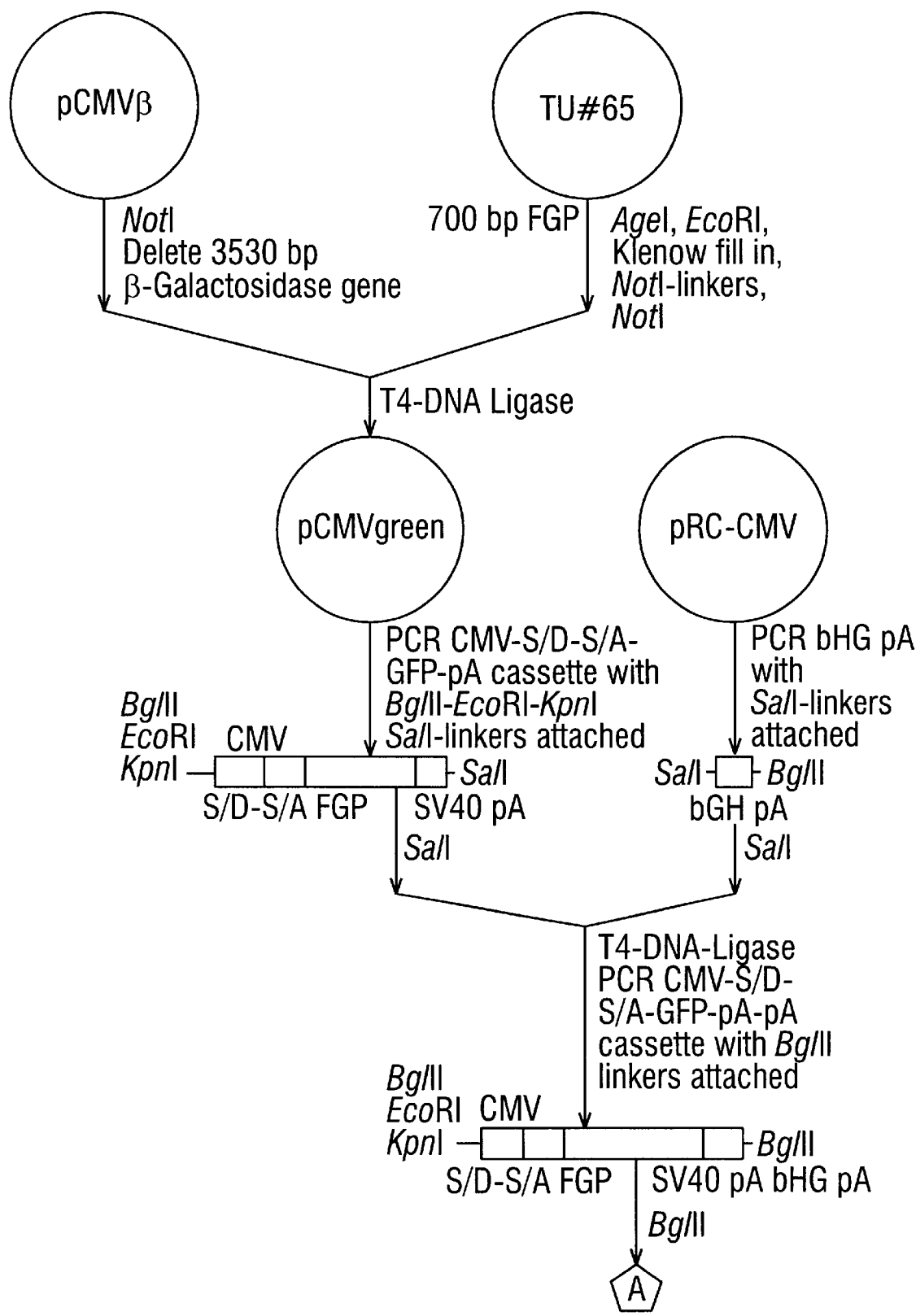
FIG. 2A-1 and FIG. 2A-2. Restriction maps of the AAV and Ad vector plasmids. Only those restriction sites relevant for the construction of the rAAV plasmids are shown. The sizes of removable elements and reporter gene cassettes are shown in base pairs. The genealogy of the genes and transcription elements is as follows: TR is the PstI-BglII-fragment (145 bp+oligo (dG).oligo (dC), 160 bp total) from dl3-94 (McLaughlin et al., 1988); $P_{cmv}$ is the CMV immediate/early promoter/enhancer; SD/SA are the SV40 late viral protein gene 16s/19s splice donor and acceptor signals; gfp is the *A. victoria* green fluorescent protein cDNA in $pTR_{BS}$-UF, or the chemically synthesized humanized wt $gfp_h$cDNA in $pTR_{BS}$-UF 1, or the Thr65 $gfp_h$ in $pTR_{BS}$-UF2, or the His66 $gfp_h$ in $PTR_{BS}$-UFB; $pA_1$ is the SV40 polyadenylation signal from the SV40 genome; $PO_{enh}$ is a tandem repeat of the enhancer from the polyoma virus mutant PYF441; $P_{TK}$ is the TK promoter of HSV; $neo^r$ is the neomycin resistance gene from Tn5; $pA_2$ is the bovine growth hormone polyadenylation signal from pRc/CMV (Invitrogen); IRES is the internal ribosomal entry site of Poliovirus type 1 from pSBC-1 (Dirks et al., 1993).

The jellyfish green fluorescent protein (GFP) has been proposed as a promising candidate for use as a reporter gene. However, a significant limitation of the gfp gene is that it does not result in adequate expression in mammalian cell systems. Indeed, the inventors' initial attempts to express the jellyfish GFP reporter gene delivered into human cell by a recombinant adeno-associated virus (AAV) were unsuccessful.

The present inventors hypothesized that an important reason for the low expression of GFP was the poor translation efficiency of the mRNA in the human cell environment, which is characterized by a set of isoacceptor tRNAs that are different than those used in the jellyfish. In solving the expression problem, this invention thus provides synthetic versions of jellyfish green fluorescent protein ($gfp_h$) cDNA that are adapted for high level expression in mammalian cells, especially those of human origin. According to this invention, base substitutions are made in gfp codons in order to change the codon usage within the gfp10 coding sequence so that it is more appropriate for expression in mammalian cells. Also provided are expression plasmids, and a series of versatile recombinant AAV and Ad vectors for delivery and expression of genes in mammalian and human cells.

In certain preferred aspects, the invention concerns a particular synthetic version of the A. victoria green fluorescent protein cDNA that is adapted for high level expression in mammalian and human cells. In this exemplary construct, a total of 92 base substitutions were made in 88 codons in order to change the codon usage within the gfp10 coding sequence and dramatically improve expression in mammalian cells.

For fluorescence microscopy, the inventors increased the sensitivity of the GFP reporter gene system approximately 22 fold for one humanized construct and at least 45 fold for a second humanized construct. In FACS analyses with humanized gene constructs, one construct was at least 32-fold more detectable than the original jellyfish gene, and the other construct was 190-fold more detectable than the original jellyfish gene. When humanized GFP is stably integrated as part of the gfp-neo cassette of the rAAV provirus in G418-resistant cell lines, a considerable portion of the cells express a visually detectable GFP.

According to previously published data, rAAV integrates as a tandem repeat with the number of genome copies per cell ranging from 1 to 10 (Cheung et al., 1980; Laughlin et al., 1986; McLaughlin et al., 1988; Samulski et al., 1989). Therefore, the range of 1 to 10 copies of humanized GFP per cell under the control of a strong promoter, as described herein, can be detected. For certain GFP mutants, this number could be as low as one.

As an example of versatile vectors for use with the humanized GFP, rAAV vectors are provided. The design of the pTR$_{BS}$-UF (User-Friendly) series of vectors (FIG. 2A-1 and FIG. 2A-2) provides convenience and flexibility in the construction of rAAV vectors. To use the maximum cloning capacity of 5 Kbp the whole reporter gene cassette can be deleted by digestion with BglII, thus leaving the two terminal repeats of AAV which are the only sequences required for replication and packaging of AAV DNA.

The PTR$_{BS}$-UF series contains two reporter gene cassettes, GFP and neo, each with its own promoter and polyadenylation signal. These two transcription units can be independently deleted (KpnI-NotI digest for GFP and SalI digest for neo), which increases the cloning space for the gene of interest. Even if used as is, the vector can accommodate another transcription unit of up to 1.6 Kbp.

Furthermore, the efficiency of a particular promoter in any given cell type or tissue could also be tested by substituting it for the CMV promoter upstream of the gfp gene after digesting the vector DNA with KpnI and XbaI. The design of the pTR$_{BS}$-UF3 vector also allows for the coordinate expression of the reporter gfp gene and the gene of interest from the same promoter by the use of an IRES element.

In addition, the inventors describe the construction of an Ad shuttle vector, carrying the humanized GFP reporter gene under the control of the IRES element. 293 cells infected with recombinant Ad displayed typical CPE and bright green fluorescence. Expression of the GFP allowed for quick and easy selection of true recombinant Ad clones, discriminating them from false plaques.

The humanized GFP can also be incorporated into other viral and non-viral vector and expression systems. Using the humanized genes and vectors of the present invention, efficient transduction and expression of gfp gene sequences in mammalian and human cell lines is possible. This is exemplified by gene expression in vivo within neurosensory cells of guinea pig eye, shown herein. The humanized gfp genes have many uses, such as in cell sorting by fluorescence-activated cell sorting (FACS), and in human gene therapy.

Indeed, the system described herein is shown to mediate efficient transduction and expression of genes in cells of mammalian origin to a level sensitive enough to allow detection by simple FACS sorting. Selection of transduced cells with drugs, such as G418, or manipulation of cells for the visualization of enzymatic activities such as β-galactosidase, is thus eliminated. Since AAV and Ad, by way of example, have a very broad host range, the described vectors will be useful in many gene delivery technologies, including human gene therapy.

Green Fluorescent Protein (GFP) Genes

Green fluorescent protein genes and functional proteins are believed to be present in a variety of organisms, as shown in Table 1. A gfp gene from any of the bioluminescent cnidaria and ctenophora that express such genes can be used as the starting point for preparing a humanized gfp gene in accordance with the present invention.

TABLE 1

Bioluminescent Cnidaria and Ctenophora Exhibiting Green Fluorescent Protein (GFP)

| Phylum/Class | Genus | Reference |
| --- | --- | --- |
| Cnidaria, Hydrozoa | Aequorea | Morin and Hastings, 1971 |
| | Obelia | Morin and Hastings, 1971 |
| | Phiallidium | Morin and Hastings, 1971 |
| | Mitrocoma | Prasher, 1995 |
| | *Campanularia | Morin and Hastings, 1971 |
| | *Clytia | Morin and Hastings, 1971 |
| | *Lovenella | Morin and Hastings, 1971 |
| | *Diphyes | Morin and Hastings, 1971 |
| Cnidaria, Anthozoa | Renilla | Wampler et al., 1973 |
| | Ptilosarcus | Wampler et al., 1973 |
| | Stylatula | Wampler et al., 1973 |
| | Acanthoptilum | Wampler et al., 1973 |

*Existence of GFP deduced from in vivo green fluorescence

It is currently preferred that the gfp gene sequence from A. victoria be used as the template for creating a humanized gfp gene, as this is readily available.

Although biologically functional equivalents of gfp gene sequences are naturally encompassed by the present invention, it should be noted that attempts to truncate the gene have shown that only one residue can be sacrificed from the amino terminus and less than 10 or 15 from the carboxyl terminus before fluorescence is lost (Dopf and Horiagon, 1995). Therefore, substantially truncated gfp genes are not contemplated to be particularly useful. However, one use for such proteins may lie in high level GFP production in mammalian cells for subsequent use in antibody generation.

Green Fluorescent Proteins

Aequorea GFP is a protein of 238 amino acid residues. Its biggest absorbance peak is at 395 nm with a smaller peak at 475 nm. The amplitudes of these peaks (i.e. extinction coefficients) have been estimated as 21–30 and 7–15 mM$^{-1}$ cm$_{-1}$, respectively (Morise et al., 1974). Excitation at 395 nm yields an emission maximum at 508 nm. The quantum yield, or probability of re-emitting a photon once the molecule has been excited, is 0.72–0.85 (Morise et al, 1974), and the excited state lifetime is 3.25 ns (Perozzo et al., 1988).

The GFPs are unusually stable proteins, so their spectral properties are relatively unaffected in denaturing solutions. The purified protein also resists most proteases for many hours (Ward, 1981, 1982; Ward and Bokman, 1982; Cutler and Ward, 1993). However, on denaturation, GFP will lose its fluorescence (Ward et al., 1980). In neutral aqueous buffer solutions, the temperature at which half the fluorescence is lost was found to be 78° C. for Aequorea GFP (Ward, 1981). While the Aequorea GFP can be denatured with total loss of fluorescence using treatments of 6M guanidine-HCl (2 min at 92° C.), acidification of pH 2 or alkalinization to pH 13, it is possible to renature GFP and recover fluorescence (Ward and Bokman, 1982). There appears to be a thiol requirement for this renaturation (Surpin and Ward, 1989).

There is no absolute requirement for another Aequorea factor to form the GFP chromophore, p-hydroxy zylideneimidazolinone, which is formed by cyclization of Ser65, Tyr66 and Gly67 and 1,2-dehydrogenation of the tyrosine. The mechanism of this unique post-translational modification is a constraint on the speed with which GFP can report changes in gene expression.

Denatured protein or isolated peptides containing the chromophore absorb light but are practically nonfluorescent (Ward et al., 1980), presumably because the naked chromophore is neither rigid nor protected from jostling by solvent molecules. Chromophore formation must, of course, remain functional in any useful GFP mutant or fusion.

In yeast and HeLa cells, GFP expressed at 37° C. is many times less fluorescent than that expressed at 15° C. Heat acts mainly by causing improper maturation rather than by decreasing expression levels or the brightness of properly matured GFP (Lim et al., 1995).

Wild-type Aequorea GFP excited with fluorescein filters is about an order of magnitude less bright than the same number of molecules of free fluorescein. Switching the excitation to 395 nm does not help because such wavelengths cause rapid photoisomerization and also excite more background autofluorescence.

GFP Mutants and Variants

GFP originally cloned from *A. victoria* has several non-optimal properties including low brightness, as described above, a significant delay between protein synthesis and fluorescence development and complex photoisomerization. However, GFP could be re-engineered with the aim of providing second generation compounds in which these deficiencies are lessened or overcome and in which the excitation and emission wavelengths are shifted, creating different colors and new applications.

Most mutations in GFP result in a partial or complete loss of fluorescence without significant change in relative absorption or emission peaks. These mutations probably cause misfolding of the protein, failure of chromophore formation, or quenching of the fluorescence by insufficient shielding. Attempts to truncate the gene have shown that only one residue can be sacrificed from the amino terminus and less than 10 or 15 from the carboxyl terminus before fluorescence is lost (Dopf and Horiagon, 1995). The intolerance of GFP to major truncation is perhaps not too surprising, because the protein scaffold must both synthesize the chromophore and rigidly shield it from the surrounding water.

Amino acid replacements in the GFP polypeptide have already been reported to yield proteins with different spectral properties. A subset of mutations affect the relative ratio of absorption peaks, at 395 and 475 nn, presumably promoting or hindering deprotonation of the chromophore. Examples are T203I (Thr203→Ile) and E222G (Glu222→Gly), which simplify the spectra to single absorption peaks at either 395 or 475 nm, respectively (Ehrig et al., 1995). The mutation I167T (Ile167→Thr) inverts the wild-type ratio of the two peaks without eliminating either completely (Heim et al., 1994).

A second subset of mutations produce essentially new excitation and emission spectra with significantly altered characteristics. Examples of this type of mutation are found within the chromophore region itself.

(a) Tyr66 Variants

The GFP from Aequorea and that of the sea pansy *Renilla reniformis* share the same chromophore, yet Aequorea GFP has two absorbance peaks at 395 and 475 nm, whereas Renilla GFP has only a single absorbance peak at 498 nm, with ≈5.5-fold greater monomer extinction coefficient than the major 395-nm peak of the Aequorea protein (Ward, 1981). For many practical applications, the spectrum of Renilla GFP would be preferable to that of Aequorea because wavelength discrimination between different fluorophores and detection of resonance energy transfer are easier when the component spectra are tall and narrow rather than low and broad.

Furthermore, the longer wavelength excitation peak (475 nm) of Aequorea GFP is almost ideal for fluorescein filter sets and is resistant to photobleaching but has lower amplitude than the shorter wavelength peak at 395 nm, which is more susceptible to photobleaching (Chalfie et al., 1994). For the foregoing reasons, conversion of the Aequorea GFP excitation spectrum to a single peak, preferably at longer wavelengths, is desirable.

Such a conversion was achieved by Heim et. al. (1994), who described GFP mutagenesis and screening in which GFP variants with altered spectra were isolated. Replacement of the central tyrosine (Y66) by other aromatic amino acids (Trp, His or Phe) shift the excitation and emission spectra to progressively shorter wavelengths.

Heim et. al. (1994) performed random mutagenesis of the gfp cDNA using hydroxylamine treatment (Sikorski and Boeke, 1991) and by increasing the error rate of the PCR™ with 0.1 mM $MnCl_2$, 50 µM dATP, and 200 µM of dGTP, dCTP, and dTTp (Muhlrad et al., 1992). Colonies on agar were visually screened for different emission colors and ratios of brightness when excited at 475 vs. 395 nm, supplied by a xenon lamp and grating monochromator for which the output beam was expanded to illuminate an entire culture dish.

A mutant was isolated by Heim et. al. (1994) that was excitable by UV light and fluoresced bright blue in contrast to the green of wild-type protein. The excitation and emission maxima were hypsochromically shifted by 14 and 60 nm, respectively, from those of wild-type GFP. The mutated DNA of the critical protein contained a Tyr66→His change in the center of the chromophore. The fluorescence spectra of Tyr66His are not sensitive to pH changes until the protein is on the verge of denaturation, which provides additional evidence that the chromophore is inaccessible to solvent.

Further site-directed mutagenesis of tyrosine to tryptophan and phenylalanine was carried out (Heim et. al., 1994). Tryptophan gave excitation and emission wavelengths intermediate between tyrosine and histidine but was only weakly fluorescent, perhaps due to inefficiency of folding or chromophore formation, whereas phenylalanine gave no detectable fluorescence.

Although the Tyr66→His mutant is less fluorescent than wild-type GFP, presumably because the alternative amino acids fit less well into the central cavity, it is of course an important variant. The availability of several forms of GFP with different excitation and emission maxima facilitates two-color assessment of differential gene expression, developmental fate and protein trafficking, as discussed below.

(b) Ser65 Variants

The desire to create GFP variants with spectra much closer to that of Renilla also motivated the studies of Heim et. al. (1995). Serine 65 of the amino-acid sequence of Aequorea GFP becomes part of the ºp-hydroxybenzylideneimidazolinone chromophore. To test the hypothesis that Ser 65 undergoes additional dehydration to form a vinyl side chain, Heim et. al. (1995) mutated that residue to Ala, Leu, Cys or Thr. If a vinyl group were formed by elimination of $H_2O$ or $H_2S$, Ser and Cys should give identical spectra very different from Ala and Leu in which elimination is impossible.

Heim et. al. (1995) produced four mutants showing single excitation peaks, located at 470–490 nm, whose amplitudes were four to sixfold greater than that of wild-type GFP for equal numbers of molecules. These results exclude vinyl formation. The Ser65→Thr mutant was selected for further characterization as it had the longest wavelengths of excitation and emission (490 and 510 nm), which closely resembled those reported for Renilla GFP (498 and 508 nm).

The crucial post-translational oxidation to produce the fluorophore from the nascent polypeptide chain proceeded about fourfold more rapidly in S65T than in the wild-type protein (Heim et. al., 1995). This acceleration ameliorates a potentially significant limitation in using GFP as a reporter protein for rapid gene inductions.

Mutations of Ser 65 to Arg, Asn, Asp, Phe, and Trp gave fluorescence intensities well below that of wild type.

In summary, the advantageous properties of the Ser65Thr GFP variant (Heim et al., 1995) include: about sixfold greater brightness than wild-type when each is excited at its longest-wavelength peak; fourfold faster oxidation to the final fluorescent species than wild-type; and no photoisomerization and only very slow photobleaching. Preliminary findings indicate that Ser65Thr photobleaches at about ⅐ the rate of fluorescein at 488 nm irradiation in air-saturated buffer at pH 7.1. As the extinction coefficient of Ser65Thr is about ⅘ that of fluorescein under these conditions, the quantum efficiency of photobleaching of Ser65Thr may be calculated to be about ¼ that of fluorescein.

These advantages make Ser65Thr more attractive than wild-type GFP for most applications except those in which long-wave UV excitation or photo-isomerization is essential. It will particularly provide greater sensitivity using commonly available fluorescein isothiocyanate (FITC) filter sets (450–490 nm excitation).

(c) Other Red-Shifted Mutants

Delagrave et al. (1995) have also performed extensive random mutagenesis of GFP residues 64–69 and isolated six mutants whose spectra are qualitatively similar to the Ser65 mutants described above. Four of them have the same substitutions (Leu, Cys or Ala) at position 65 as listed above.

The methods used by Delagrave et al. (1995) for the construction of spectrally shifted GFP mutants have previously been employed to produce a variety of spectrally diverse bacteriochlorophyll-binding proteins using optimized combinatorial mutagenesis and Digital Imaging Spectroscopy (DIS) (Goldman and Youvan, 1992; Delagrave and Youvan, 1993).

DIS enables simultaneous screening of thousands of colonies directly on petri dishes by acquiring spatially resolved spectral information (Youvan et al, 1995; Youvan, 1994). Images of petri dishes, illuminated at different wavelengths, are captured by a charge-coupled device (CCD) camera and further processed by software establishing radiometric calibration. Using optimized combinatorial mutagenesis and DIS, further GFP mutants can be isolated.

In the combinatorial library screening of Delagrave et al. (1995), the region of GFP targeted for mutagenesis was the 6 amino acid sequence between Ple64 and Glu69 (Phe Ser Tyr Gly Val Gln; SEQ ID NO:4) which includes the chromophore itself. A mutagenic oligonucleotide was designed to favor the incorporation of an aromatic amino acid at position 66 and to fully randomize the other five codons. The sequence of the oligonucleotide employed for mutagenesis was obtained using the CyberDope computer program.

The resulting library of approximately $3 \times 10^5$ mutant GFP genes was expressed in B121 (DE3). Thousands of colonies on petri dishes were screened by fluorescence using DIS (Delagrave et al., 1995). The spectrally shifted mutants were initially identified by the green fluorescence observed when excited with 490 nm light, which disappears when excited at 410 nm. In contrast, wild-type GFP fluorescence is much brighter with 410 mn illumination. DIS revealed that approximately one in $10^4$ colonies expressed a functional fluorescent protein.

Delagrave et al. (1995) picked and sequenced several red-shifted GFP (RSGFP) clones. Tyr66 and gly67 appeared to be conserved while the other four positions were less stringent; $ser^{65}$ was not necessary for the observed phenotype. RSGFPs are easily distinguished from wild-type GFP because their excitation maxima are red-shifted by about 100 nm, from 390 nm in wild-type Aequorea GFP to 490 nm in RSGFP. One particular clone is RSGFP4, which has the chromophore sequence Met Gly Tyr Gly Val Leu (SEQ ID NO:5). The emission of RSGFP4 is nearly identical to that of wild-type GFP, but the excitation spectra are very different.

Delagrave et al. (1995) reported that this sequence information is amenable to further manipulation by Exponential Ensemble Mutagenesis (EEM) and Recursive Ensemble Mutagenesis (REM) strategies (Delagrave and Youvan, 1993; Delagrave et al., 1993), potentially to produce a 'rainbow' of multispectral fluorescent proteins. It is expected that by constructing new combinatorial libraries optimized by REM or EEM, the frequency of functional mutants will be high enough to allow the isolation of rare clones with significant emission shifts.

Humanized gfp Genes

Although the properties of wild-type GFP are improved in mutants, such as described above, wild-type GFP lacks one stage of amplification built into a true enzymatic reporter system in which each protein molecule can generate thousands of chromophore or fluorophore molecules. Because each GFP represents one fluorophore, relatively high levels of GFP expression, as much as $10^6$ molecules per cell (Rizzuto et al., 1995) may be necessary to give bright signals.

The foregoing emphasizes the importance of the present invention, the focus of which is to provide for increased GFP expression in mammalian and human cells. Each of the mutants described above, or indeed any desired mutant or a panel of mutants, can also be prepared in a humanized background as provided by the present invention. This is because the humanizing aspects of the invention change the DNA sequence independently of the protein sequence.

Previous attempts to express GFP in mammalian cells have used the Kozak consensus (Adams et. al. 1995). A so-modified GFP gene has been inserted into a mammalian expression vector and used in CHO-K1 cells (Adams et. al.

1995). Pines (1995) has also reported transient GFP expression COS-7, HeLa and NIH 3T3 cells; and Rizzuto et al. (1995) have reported expression of GFP in mitochondria of intact cells. However, these studies are believed to reflect relatively low level expression and, furthermore, are believed to be in. contrast to the negative results obtained by many of those working in the art. These few positive results are believed to be a function of the high copy number of gfp genes introduced into the cell.

The approach taken by the present inventors is in contrast to the Adams et. al. (1995) method, and addresses the poor translation efficiency of GFP mRNA in the human cell environment by using cDNAs that contain base substitutions in order to change the codon usage so that it is more appropriate for expression in mammalian cells. Using such humanized constructs results in green fluorescence in cells that have a low copy number of humanized gfp genes, e.g., in the range of less than 10, and even about 1 or 2 when using certain humanized gfp mutant genes.

The correlation between the abundance of tRNAs and the occurrence of the respective codons in protein-expressing genes has been described for *E. coli*, yeast and other organisms (Bennetzen and Hall (1982); Grantham et al (1980); Grantham et al. (1981); Ikemura (1981a; 1981b; 1982); Wada et al. (1990)). However, until codon changes are actually made in any given gene, their effects on translation efficiency and overall expression levels cannot be established. This is similar to the situation involving the Kozak sequence, which is not believed to have been particularly helpful in increasing expression of gfp in mammalian cells despite expectations. Now that the present inventors have shown that humanization is effective for gfp gene expression, the usefulness of the GFP technology has been significantly enhanced.

In order to humanize jellyfish gfp in accordance with the present invention, the inventors first conducted a detailed analysis of the codons in the gfp gene. Table 2 shows the results of a comparison between jellyfish gfp codons and codons commonly used in human genes (Wada et. al., 1990). This enabled the inventors to identify important differences between gfp and general human gene sequences and to identify changes that should be made.

An exemplary humanized sequence in accordance with the present invention is represented by SEQ ID NO:3. However, it will be understood that the humanized sequences of the present invention are by no means limited to the representative sequence of SEQ ID NO:3. Rather, in light of the following instructions, one of skill in the art will readily be able to prepare a number of different humanized gfp sequences.

Although any changes that replace a rarely used jellyfish codon with a codon that is more frequently used in human genes are considered to be useful changes, certain codon changes will naturally be preferred over others. In this regard, the inventors have identified a number of gfp codons that are rarely or almost never used in human genes. As discussed below, such codons are the first candidates that should be changed in producing a humanized gene in accordance with the present invention.

In making general humanizing changes, codons to be humanized can be identified by those of skill in the art from studying the information presented herein in Tables 2 and in Table 3 and 4. For example, in utilizing the information in Table 2, one would compare the frequency of the jellyfish codon against the frequency of those codons commonly used in human genes, and make any appropriate changes. By way of an example only, consider the amino acid leucine; the codon CUU is used eleven times in the gfp gene, but this codon corresponds to only the fourth preferred codon in human genes. The leucine codon UUA also features prominently in the jellyfish gene, and this codon is the last choice for use in the human genome. Changing the Leucine codons would thus make an appropriate starting point for preparing a humanized gene.

Further changes that can be made following an analysis of Table 2 are to change the arginine codons of AGA, which is only a fourth choice in the human genome, to a more preferable codon such as CGC or AGG; changing Serine codons such as UCG or UCA to more preferred codons such as UCC and AGC; optimizing threonine codons to ACC; avoiding the use of the proline codon GCC; changing the alanine codon GCA to the most preferred human codon CGG; avoiding the use of the predominant glycine codons GGA and GGU and replacing these with those preferred in human genes, GGC and GGG; changing the frequently occurring valine codons GUU and GUA, and instead using the codon GUG, which is clearly favored in the human genome; and avoiding the isoleucine codon AUA and changing this to the preferred codon AUC.

In the amino acids for which there is only a choice of two codons, the inventors noticed that the wild type gfp gene usually employs the least preferred codon as compared to the human genome. Therefore, appropriate changes would be made in the following codons AAA for lysine; CAA for glutamine; CAU for histidine; GAA for Glutamine; GAU for Asparagine; and UUU for Phenylalanine; and replacing these with AAG, CAG, CAC, GAG, GAC, and UUC, respectively.

Additional changes can also be made from considering the information in Table 3 and Table 4. These tables provide important information regarding codon preference in a format that is easily used. Table 3 provides a list of the codons that are preferred for use in the humanized gfp constructs of the invention. Table 4 is simply the same information that incorporates U (uridine) rather than T (thymine), for ready cross-reference with FIG. 1A, FIG. 1B and FIG. 1C.

TABLE 3

Preferred DNA Codons for Human Use

| Amino Acids | | | Codons Preferred in Human Genes | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | <u>CTA</u> | <u>TTA</u> |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | <u>TCG</u> |
| Threonine | Thr | T | ACC | ACA | ACT | ACG | | |
| Valine | Val | V | GTG | GTC | GTT | <u>GTA</u> | | |
| Tryptophan | Trp | W | TGG | | | | | |
| Tyrosine | Tyr | Y | TAC | TAT | | | | |

The codons at the left represent those most preferred for use in human genes, with human usage decreasing towards the right.
Double underlined codons represent those which are almost never used in human genes.

TABLE 4

Preferred RNA Codons for Human Use

| Amino Acids | | | Codons Preferred in Human Genes | | | | | |
|---|---|---|---|---|---|---|---|---|
| Alanine | Ala | A | GCC | GCU | GCA | GCG | | |
| Cysteine | Cys | C | UGC | UGU | | | | |
| Aspartic acid | Asp | D | GAC | GAU | | | | |
| Glutamic acid | Glu | E | GAG | GAA | | | | |
| Phenylalanine | Phe | F | UUC | UUU | | | | |
| Glycine | Gly | G | GGC | GGG | GGA | GGU | | |
| Histidine | His | H | CAC | CAU | | | | |
| Isoleucine | Ile | I | AUC | AUU | AUA | | | |
| Lysine | Lys | K | AAG | AAA | | | | |
| Leucine | Leu | L | CUG | CUC | UUG | CUU | <u>CUA</u> | <u>UUA</u> |
| Methionine | Met | M | AUG | | | | | |
| Asparagine | Asn | N | AAC | AAU | | | | |
| Proline | Pro | P | CCC | CCU | CCA | CCG | | |
| Glutamine | Gln | Q | CAG | CAA | | | | |
| Arginine | Arg | R | CGC | AGG | CGG | AGA | CGA | CGU |
| Serine | Ser | S | AGC | UCC | UCU | AGU | UCA | <u>UCG</u> |
| Threonine | Thr | T | ACC | ACA | ACU | ACG | | |
| Valine | Val | V | GUG | GUC | GUU | <u>GUA</u> | | |
| Tryptophan | Trp | W | UGG | | | | | |
| Tyrosine | Tyr | Y | UAC | UAU | | | | |

The codons at the left represent those most preferred for use in human genes, with human usage decreasing towards the right.
Double underlined codons represent those which are almost never used in human genes.

From studying the information in Table 3 and Table 4, one of skill in the art would readily discern that the jellyfish gfp codons CTA, TTA, TCG and TCA (or CUA, UUA, UCG or GUA) should be changed to a more preferred codon. As a general guideline, those codons listed in columns 5 and 6 generally represent codons that one would prefer to change in creating a humanized gene, the codons listed in column 4 should also often be changed in creating a humanized gene; the codons listed in column 3 may or may not be changed, depending on the number of changes that one wishes to make in total and on the particular amino acid that is to be encoded. Those codons listed in columns 1 and 2, when occurring in the wildtype gfp sequence, will generally be appropriate and should not need changing, unless there is only a choice of two codons available. However, replacing a codon from column 2 with a codon from column 1 is certainly a useful option, particularly where there is only a choice of two codons. Given this information, it will now be understood that, when introducing changes into the gfp sequence, one would generally desire to introduce a codon of column 1 wherever possible.

In light of the foregoing discussion, it will be clear that the exemplary sequence of SEQ ID NO:3 is only one of the many operable species that are encompassed by the present invention. In SEQ. ID NO:3, 88 codons contain one or more base substitutions. 88 codons from a sequence that encodes 328 amino acids represents a change of about 37%. However, it is contemplated that changing about 10% of the codons would produce a useful increase in expression levels and such gene sequences therefore fall within the scope of the present invention. Changing about 15%, 20%, 25% or 30% of the codons within the jellyfish gfp sequence is also considered to be useful and the humanized genes of this invention encompass those gene sequences that fall within the aforementioned ranges.

In certain embodiments, depending on the nature of the codon changes introduced, it may not be necessary to even make a 10% change in the codon usage of the gfp gene. For example, if each of the ten least favored codons were to be changed and replaced with those most preferred for use in human genes, it is contemplated that the resultant sequence may achieve reasonable expression in human and mammalian cells. Changing ten codons from within 328 represents a percentage change of about 4%. Therefore, so-called "4% humanized genes" also fall within the scope of the present invention given the following provision - that when making only a limited number of changes, one would generally wish to change the ten codons located at codon positions 18, 53, 93, 125, 150, 178, 195, 208, 236 and 224 of the gfp gene sequence. When making these key changes along with a number of other changes, it is contemplated that changing at least about 7, 8 or 9 of these codons will be sufficient to result in a humanized gene with improved expression. As described above, leucine would preferably be encoded by CTG, CTC or TTG; valine would preferably be encoded by GTG; and serine would preferably be encoded by AGC.

Although gfp gene sequences in which about 4-5, about 10, about 20 or about 30-35% of the codons have been changed will generally be preferred, there is no reason that further changes should not be made if so desired. Humanized gene sequences in accordance with the present invention may therefore be sequences that contain humanized codons at about 40%, 50%, 60%, 70% or even about 80–90% of the codon positions within the full length codon region. In reviewing SEQ ID NO:3, with a view to introducing still further humanizing changes, a number of positions are identifiable in which further optimizing changes could be introduced. These include, for example, those codons found at codon positions 6, 9, 14, 17, 19, 21, 23, 26, 27, 31, 33, 34, 35, 36, 40, 45, 50, 51, 62, 71, 83, 99, 101, 102, 111, 115, 116, 128, 130, 132, 133, 134, 136, 142, 157, 171, 173, 174, 181, 183, 186, 209, 210, 213, 223 and 230 of SEQ. ID NO:3.

Uses of Green Fluorescence Proteins

The potential of GFP as a reporter molecule stems from properties such as ready detection, it can be detected on irradiation using standard long-wave UV light sources; the possibility of real-time detection in vivo; the fact that the introduction of a substrate is not required; and its relatively small size (26.9 kD) and monomeric nature, which make protein fusions manageable.

The humanized GFP of the present invention renders several of these methods practical rather than speculative. Humanized gfp genes can therefore be used to identify transformed cells, e.g., by fluorescence-activated cell sorting (FACS) or fluorescence microscopy; to measure gene expression in vitro and in vivo; to label specific cells in multicellular organisms, e.g., to study cell lineages; to label and locate fusion proteins; and to study intracellular trafficking and the like.

Standard biological applications of GFP should not be overlooked. For example, its use as a molecular weight marker on protein gels and Western blots, in calibration of fluorometers and FACS machines and in microinjection into cells and tissues.

In methods to produce fluorescent molecular weight markers, a humanized gfp gene sequence is generally fused to one or more DNA sequences that encode proteins having defined amino acid sequences and the fusion proteins are expressed from an expression vector. Expression results in the production of fluorescent proteins of defined molecular weight or weights that may be used as markers (following calculation of the size of the complete amino acid).

Preferably, purified fluorescent proteins would be subjected to size-fractionation, such as by using a gel. A determination of the molecular weight of an unknown protein is then made by compiling a calibration curve from the fluorescent standards and reading the unknown molecular weight from the curve.

(a) Different colored GFPs

As mentioned, amino acid replacements in humanized GFP that produce different color forms permit simultaneous use of multiple reporter genes. Different colored humanized GFPs can be used simply to identify multiple cell populations in a mixed cell culture or to track multiple cell types, enabling differences in cell movement or migration to be visualized in real time without the need to add additional agents or fix or kill the cells.

Other options include tracking and determining the ultimate location of multiple proteins within a single cell, tissue or organism; differential promoter analysis in which gene expression from two different promoters is determined in the same cell, tissue or organism; and FACS sorting of mixed cell populations.

In tracking proteins within a cell, the humanized GFP variants would be used in a analogous manner to fluorescein and rhodamine and would tag interacting proteins or subunits whose association could then be monitored dynamically in intact cells by fluorescence resonance energy transfer (Adams et al., 1991; 1993).

The techniques that could be used with spectrally separable humanized GFP derivatives are exemplified by confocal microscopy, flow cytometry, and fluorescence activated cell sorting (FACS) using modular flow, dual excitation techniques.

(b) Identification of Transfected Cells

The many ways in which humanized gfp may be used can be divided into certain broad areas. First, to simply identify cells. In these methods, humanized gfp is used alone to express GFP in a cell. One use for this method would be in pre-labeling isolated cells or a population of similar cells prior to exposing the cells to an environment in which different cell types are present. Detection of GFP in only the original cells allows the location of such cells to be determined and compared with the total population.

A second group of methods concerns the identification of cells that have been transfected with exogenous DNA of interest. Identifying cells transfected with exogenous DNA is required in many in vitro embodiments and, also, in in vivo gene therapy.

A first example of this general group is where a humanized gfp sequence is fused to a DNA sequence encoding a selected protein in order to directly label the encoded protein with GFP. Expressing such a humanized GFP fusion protein in a cell results in the production of fluorescently-tagged proteins that can be readily detected. This is useful in simply confirming that a protein is being produced by a chosen host cell. It also allows the location of the selected protein to be determined, whether this represents a natural location or whether the protein has been targeted to an organelle by the hand of man.

Cells that have been transfected with exogenous DNA can also be identified without creating a fusion protein. Here, the method relies on the identification of cells that have received a plasmid or vector that comprises at least two transcriptional or translational units. A first unit will encode and direct expression of the desired protein, while the second unit will encode and direct expression of humanized GFP. Co-expression of GFP from the second transcriptional or translational unit ensures that cells containing the vector are detected and differentiated from cells that do not contain the vector.

(c) Analysis of Promoters

The humanized genes of this invention also provide another dimension to the analysis of promoters in mammalian cells. As gfp can now be expressed in mammalian and human cells and readily detected, a range of promoters can be tested for their suitability for use with a given gene, cell, or system. This applies to in vitro uses, such as in identifying a suitable promoter for use in recombinant expression and high level protein production, and also in in vivo uses, such as in pre-clinical testing or in gene therapy in human subjects.

In practical terms, to analyze a promoter one would first establish a control cell or system. In the control, a positive result can be established by using a known and effective promoter, such as the CMV promoter preferred in certain aspects of the studies described herein. To test a candidate promoter, another cell or system will be established in which all conditions are the same except for there being different promoters in the expression vector or genetic construct. After running the assay for the same period of time and under the same conditions as in the control, the ultimate GFP expression levels would be determined. This allows a comparison of the strength or suitability of the candidate promoter with the standard promoter to be made. In using a GFP expression system that is routinely employed in a given laboratory, the positive control may even be dispensed with in certain studies of a test promoter.

Promoters that can be tested in this manner also include candidate tissue-specific promoters and candidate-inducible promoters. Testing of tissue-specific promoters allows preferred or optimal promoters for use with a given cell to be identified and distinguished from a range of possible promoters. Again, this will be useful both in vitro and in vivo. Optimizing the combination of a given promoter and a given cell type in recombinant expression and protein production can often be necessary to ensure that the highest possible levels are achieved.

It is even contemplated that these aspects of the invention could be used to analyze a candidate promoter for use in protein production employing a secretory cell. In these embodiments, the GFP expressed from the promoter would most likely be secreted from the cell into the extra cellular environment where it would then be detected.

The testing and ultimate use of inducible promoters forms another aspect of this invention. In recombinant expression for the purposes of protein production, it may be desired to induce expression at a particular stage of the cell culture or cell cycle. In analyzing the distribution of a given protein within a cell or a given system, it is also useful to use a promoter that is only switched on under certain conditions, such as in the presence of certain cytokines or hormones.

The use of humanized gfp genes with inducible promoters also extends to an analysis of the promoter itself. An example here is in the analysis of a particular promoter from a group of promoters, such as promoters associated with heat shock proteins, that are known to be expressed in various organisms throughout evolution. In this way, a promoter operable in, for example, yeast, can be taken and expressed in a mammalian cell system in order to determine whether it is operable in mammalian cells and, therefore, to determine whether mammalian cells likely include a homolog of the yeast promoter.

The use of tissue-specific promoters and inducible promoters is particularly powerful in in vivo embodiments. When used in the context of expressing a therapeutic gene in an animal, the use of such a promoter will allow expression only in a given tissue or tissues, at a given site and/or under defined conditions. This is a significant advantage which allows gene expression to be confined to a particular target organ, tissue or area, and will limit gene expression throughout the rest of the body. Achieving tissue-specific expression is particularly important in certain gene therapy applications, such as in the expression of a cytotoxic agent, as is often employed in the treatment of cancer. In expressing other therapeutic genes with a beneficial affect, tissue-specific expression is, of course, also preferred in that it optimizes the affect of the treatment.

Appropriate tissue-specific and inducible promoters will be known to those of skill in the art. By way of example only, one may mention the liver fatty acid binding (FAB) protein gene promoter, specific for colon epithelial cells; the insulin gene promoter, specific for pancreatic cells; the transphyretin, α1-antitrypsin, plasminogen activator inhibitor type 1 (PAI-1), apolipoprotein AI and LDL receptor gene promoters, each directing specific or preferential expression in liver cells. Promoters active in brain tissues include the myelin basic protein (MBP) gene promoter, specific for oligodendrocytes; the glial fibrillary acidic protein (GFAP) gene promoter, specific for glial cells; and the neural-specific enolase (NSE) promoter that is specific for nerve cells.

Inducible promoters for in vivo uses will preferably include those responsive to biologically compatible agents, preferably those that are usually encountered in defined animal tissues. An example is the human PAI-1 promoter, which is inducible by tumor necrosis factor. Further suitable examples cytochrome P450 gene promoters, inducible by various toxins and other agents; heat shock protein genes, inducible by various stresses; hormone-inducible genes, such as the estrogen gene promoter, and such like.

Promoters that are inducible by ionizing radiation may also be used in certain embodiments, particularly in gene therapy of cancer, where gene expression is induced locally in the cancer cells by exposure to ionizing radiation such as UV or x-rays. Appropriate promoters that are inducible by ionizing radiation include egr-1, fos and jun.

(d) Screening Protocols

A further development of using promoters along with the humanized gfp of the present invention is its use in screening protocols. In these embodiments, which are generally conducted in vitro, a genetically engineered cell is used to identify the presence of a particular compound or agent in a composition.

In the screening embodiments, the humanized gfp gene will be positioned downstream of a promoter that is known to be inducible by the agent that one wishes to identify. Expression of gfp in the cells will normally be silent, and will be switched on by exposing the cell to a composition that contains the selected agent. In using a promoter that is responsive to, for example, a heavy metal, a toxin, a hormone, a cytokine or other defined molecule, the presence of a heavy metal, toxin, hormone, cytokine or such like can readily be determined.

From the foregoing list, it will be appreciated that the screening aspects of this invention fall into two basic groups, which may be conveniently termed 'the biological' and 'the chemical'.

In the biological assays, cells including a humanized gfp gene under the control of a promoter that is inducible by a biological effector molecule may be used to detect the presence of such molecules in various kinds of biological samples, including blood, plasma, semen, urine, saliva. and the like. Those effector molecules that are detectable in this way include molecules such as hormones, cytokines, neurotransmitters and the like. Of course, as used throughout this application, it will be understood that the term "promoter" is being used to refer to any regulatory element. Particular examples here are the use of the sterol regulatory element, in conjunction with humanized gfp, to detect sterols in a given composition; and the similar use of the serum response element, which is induced by UV, EGF, PDGF and TPA.

In the so-called chemical assays, cells including a humanized gfp gene under the control of a promoter that is inducible by a chemical agent are used to detect the presence of the chemical agent in various compositions. These assays may be used to detect toxins or contaminants in fluids such as drinking water, and the like. The types of agents that may be detected in this way include heavy metals, toxins and various other pollutants and undesirable chemicals.

It will, of course, be realized that any of the screening assays may be used in the context of detecting agents that inhibit, suppress or otherwise downregulate gene expression from a given promoter. Such negative effects will be detectable by falling levels of and decreased fluorescence that results when gene expression is "switching off" in response to the presence of an inhibitory agent.

(e) GFP in FACS Analyses

Many conventional FACS methods require the use of fluorescent dyes conjugated to purified antibodies. Proteins tagged with a fluorescent label would be preferred over antibodies in FACS applications because cells do not have to be incubated with the fluorescent-tagged reagent and because there is no background due to nonspecific binding of an antibody conjugate. GFP is particularly suitable for use in FACS as fluorescence is stable and species-independent and does not require any substrates or cofactors.

As with other expression embodiments, a desired protein may be directly labeled with GFP by preparing and expressing a GFP fusion protein in a cell. GFP could also be co-expressed from a second transcriptional or translational unit within the expression vector that expresses desired protein, as described above. Cells expressing the GFP-tagged protein or cells co-expressing GFP would then be detected and sorted by FACS analysis. FACS analysis may be used as the end means to monitor gene expression and promoter activity when using GFP as the reporter gene.

Red-shifted GFPs are particularly suitable for use with FACS (although GFP itself can also be used). The argon ion laser used in most FACS machines emits at 488 nm, so excitation of red-shifted GFP variants (e.g., excitation peak approximately 490 nm) is more efficient than excitation of wild type GFP. The successful use of GFP with FACS techniques is shown herein.

GFP Fusion Proteins

Humanized gfp genes can be used as one portion of a fusion protein, allowing the location of the protein to be identified. Fusions of GFP with an 'exogenous' protein should preserve both the fluorescence of GFP and functions of the host protein, such as physiological functions and/or targeting functions.

Both the amino and carboxyl termini of GFP may be fused to virtually any desired protein to create an identifiable GFP-fusion. Both N- and C-terminal protein fusions prepared using the wild type gene have been reported (Wang and Hazelrigg, 1994). Fusion of proteins to the carboxyl terminus of GFP might be enhanced by linker sequences.

(a) Subcellular Localization

Localization studies have been previously carried out by subcellular fractionation and by imrnunofluorescence. However, these techniques can give only a 'snapshot' of the position of the protein at one instant in the cell cycle. In addition, artefacts can be introduced when cells are fixed for immunofluorescence. Using GFP to visualize proteins in living cells, which enables proteins to be followed throughout the cell. cycle in an individual cell, is thus an important technique.

Humanized GFP can be used to analyze intracellular protein traffic in mammalian and human cells under a variety of conditions in real time. Artefacts resulting from fixing cells are avoided. In these applications, humanized GFP is fused to a known protein in order to examine its sub-cellular location under different natural conditions.

Pines (1995) described the use of wild type GFP as a tag to create GFP-cyclin chimeras that were expressed in mammalian tissue-culture cells by transient transfection. In preliminary studies, GFP and both N- and C-terminal GFP-cyclin chimeras were detected in living cells, and the fluorescence was followed in such cells for several hours.

Pines (1995) used the cytomegalovirus early promoter to drive GFP expression in transiently transfected cells and expressed GFP in COS-7, HeLa and NIH 3T3 cells. In all cases there was a lag period (>15 h) before fluorescence was detected, although chimeras were detected by immunofluorescence after 12 h. This may be due to the requirement for GFP to autoxidize, which takes around 4 h in bacteria (Heim et al., 1994). In contrast to these studies in mammalian cells, the present invention has the distinct advantage that GFP fluorescence was detectable is about 6 hours.

In the studies of Pines (1995) and others, GFP has not interfered with the natural subcellular localization of proteins. Pines (1995) showed that GFP alone is distributed throughout the cell, both in the nucleus and the cytoplasm. When tagged to cyclin A, it was found to be primarily nuclear, and when tagged to cyclin B, it was found to be cytoplasmic, associating with microtubules or the vesicle compartment depending on the B-type cyclin (Pines, 1995).

Humanized GFP may be used to tag virtually any protein and to follow the location of the protein under different conditions. For example, in following a given protein through meiosis, mitosis, apoptosis or other cellular processes. The location of a given protein can also be determined in response to a number of external stimuli. Such stimuli include different physical conditions, such as increasing or decreasing temperature, and also different chemical environments. By the term "chemical environment", it is meant both natural environments that may be encountered, such as compositions with different levels of salt or serum growth factors and the like, and also compositions to which an effector molecule has been added.

Compositions with effector molecules are used in order to provoke a response in a given cell. The humanized gfp of the invention can be used in assays in which the response of a cell to a given effector or agonist is determined. By using such methods, the location of a given protein in response to a hormone, cytokine, neurotransmitter or other agent can be determined. It is well known that the location of proteins vary in response to varying external stimuli, and that proteins move between internal compartments, such as, e.g., the outer membrane, cytosol, endoplasmic reticulum and nuclear compartments.

(b) GFP-driven targeting

Another use of GFP-fusion proteins is in detecting a targeted protein in a particular locale after the protein has been adapted for transport into a particular cellular compartment despite the natural destination of the protein. To achieve this, a targeting sequence, such as a nuclear or mitochondrial targeting sequence, is fused to the desired protein along with the GFP sequence. This is in contrast to the methods described immediately above, where the natural location of a protein is determined using GFP.

The nucleus contains many proteins that help mediate its unique functions. These proteins are imported from the cytosol where they are made. They must pass through both the outer and inner nuclear membranes to reach the inside of the nucleus (the nuclear lumen). This transport process is selective: many proteins made in the cytosol are excluded from the nucleus. Many nuclear proteins interact with receptor proteins located on the pore margin that actively transport the proteins into the nucleus while enlarging the pore channel.

The selectivity of nuclear transport resides in nuclear import signals, which are present only in nuclear proteins. Nuclear import signals have been precisely defined in some nuclear proteins using genetic engineering techniques. The signal, which can be located anywhere in the protein, consists of a short peptide (typically from four to eight amino acid residues) that is rich in the positively charged amino acids lysine and arginine and usually contains proline. For example, the T-antigen nuclear import signal is Pro Pro Lys Lys Lys Arg Lys Val (SEQ ID NO:6).

Humanized GFP may be used to confirm that a selected protein has been imported into the nucleus following expression of a construct in which the protein in question is fused to GFP and a nuclear targeting sequence. This may be used as part of in vitro studies in basic science or even as part of in vivo therapy, e.g., in directing agents to the nucleus of cancer cells, and the like.

Adding a nuclear localization signal to a humanized gfp gene may also be used in order to enhance the fluorescence intensity of the expressed protein by confining the protein to the much smaller space of the nucleus. This is described herein in Example VII in the context of blue GFP mutants.

As a nuclear protein molecule needs to be repeatedly imported, e.g., after mitosis, its nuclear import signal peptide is not cleaved off after transport into the nucleus. In contrast, once a protein molecule has been imported by any of the other membrane-bounded organelles, it is passed on from generation to generation within that compartment and need never be translocated again. Therefore, the signal peptide on these molecules is often removed following protein translocation.

Mitochondria are double-membrane-bounded organelles that specialize in the synthesis of ATP-by electron transport and oxidative phosphorylation. Most of their proteins are encoded by the cell nucleus and imported from the cytosol. Moreover, each imported protein must reach the particular subcompartment in which it functions. For mitochondria there are four subcompartments: the matrix space; the inner membrane; the intermembrane space; and the outer membrane that face the cytosol. Each of these subcompartments contains a distinct set of proteins.

The study of mitochondrial biogenesis has been facilitated by the use of yeasts, into which hybrid genes encoding fusion proteins (produced by recombinant DNA techniques) can be introduced efficiently. Proteins imported into the mitochondrial matrix are usually taken up from the cytosol within a minute or two of their release from free polyribosomes.

Imported proteins almost always have a signal peptide (20–80 residues long) at their amino terminus. After being imported, the signal peptide is rapidly removed by a specific protease (a signal peptidase) in the mitochondrial matrix and then probably is degraded to amino acids in the matrix. The signal peptide can be remarkably simple. Molecular genetic experiments in which the signal peptide is progressively reduced in length have shown that, for one mitochondrial protein, only 12 amino acids at the amino terminus are needed to signal mitochondrial import. These 12 residues can be attached to any cytoplasmic protein and will direct the protein into the mitochondrial matrix.

Physical studies of fill-length signal peptides suggest that they can form amphipathic α-helical structures in which positively charged residues all line up on side of the helix while uncharged hydrophobic residues line up toward the opposite side. An example of a mitochondrial import sequence is Met Leu Ser Leu Arg Gln Ser Ile Arg Phe Phe Lys Pro Ala Thr Arg Thr Leu (SEQ ID NO:7).

The transport of several precursor proteins to the mitochondrial intermembrane space begins with their initial transfer into the matrix. Here, a very hydrophobic amino acid sequence is strategically placed after the aminoterminal signal peptide that initiates import. Once the amino-terminal signal is cleaved by the matrix protease, the hydrophobic sequence functions as a signal peptide to reinsert the protein into the inner membrane. This transfer from the matrix presumably occurs by a mechanism similar to that used for protein import into the ER membrane, and it is also the mechanism used to insert proteins that are encoded in the mitochondrion into the inner membrane. The transport of proteins from the cytosol to the mitochondrial inner membrane also requires a hydrophobic signal peptide.

The use of GFP and a mitochondrial targeting sequence to visualize mitochondrial movement in living cells has been reported by Rizzuto et al. (1995). In contrast to dyes such as rhodamine, using GFP revealed morphological changes induced in mitochondria by drugs that collapse the organelle membrane potential.

In these studies, Rizzuto et al. (1995) used a DNA fragment encoding the amino-terminal 31 amino acids of the precursor of sub-unit VIII of cytochrome c oxidase, which form a mitochondrial targeting sequence, as part of the fusion protein-encoding sequences. A chimeric cDNA was created to encode, from the amino to the carboxyl termini: a mitochondrial pre-sequence and 6 amino acids of the mature cytochrome c oxidase protein; a few linker amino acids; and GFP. This construct expressed GFP which was imported into the mitochondria.

The use of humanized GFP will be an improvement in the type of studies described by Rizzuto et al. (1995), in which one simply desires to label the mitochondria as a whole. Humanized GFP may also be used to confirm that a selected protein has been imported into the mitochondria following expression of a construct in which a desired protein is fused to GFP and a mitochondrial targeting sequence. Here, the mitochondrial targeting sequence souls be positioned at the N-terminal of the fusion protein (at the 3' end of the encoding nucleic acid).

Gene Therapy Applications

Successful gene therapy generally requires the integration of a gene able to correct the genetic disorder into the host genome, where it would co-exist and replicate with the host DNA and be expressed at a level to compensate for the defective gene. Ideally, the disease would be cured by one or a few treatments, with no serious side effects. There have been several approaches to gene therapy proposed to date, each of which may benefit from combination with the humanized gfp of the present invention.

One approach is to transfect DNA containing the gene of interest into cells, e.g., by permeabilizing the cell membrane either chemically or physically. This approach is generally limited to cells that can be temporarily removed from the body and can tolerate the cytotoxicity of the treatment (i.e. lymphocytes). Calcium phosphate precipitation (Graham and Van Der Eb, 1973; Rippe et al, 1990), DEAE-dextran (Gopal, 1985), electroporation (Tur-Kaspa et al., 1986; Potter et al., 1984) and direct microinjection are examples of such methods.

Liposomes or protein conjugates formed with certain lipids and amphophilic peptides can be used for in vivo and in vitro transfection (Stewart et al., 1992; Torchilin et al., 1992; Zhu et al., 1993; Ledley et al., 1987; Nicolau et al., 1983; Nicolau and Sene, 1982) and DNA coupled to a polylysine-glycoprotein carrier complex may also be used.

The efficiency of gene integration in this manner is generally very low. It is estimated that the gene of interest integrates into the genome of only one cell in 1,000 to 100,000. In the absence of integration, expression of the transfected gene is limited to several days in proliferating cells or several weeks in non proliferating cells due to the degradation of the non-integrated DNAs. This invention may be used to readily identify cells that express the desired transfected gene for longer times.

Jiao et al. (1993) describe the success of particle bombardment-mediated gene transfer protocols for transferring and expressing genes in brain tissues, suggesting that this can be employed as an effective method for gene transfer into such tissues.

Plasmids may be used to directly transfer humanized gfp genetic material into a cell (Wolfe et al., 1990). DNA segments themselves can therefore be used as delivery agents. The technology for using DNA segments has recently been developed and is generally termed "DNA Vaccination" (Cohen, 1993). It is now known that cells can take up naked DNA and express encoded proteins.

The utilization of this technology, and variations thereof, such as those described by Ulmer et al. (1993); Tang et al. (1992), Cox et al. (1993), Fynan et al. (1993), Wang et al. (1993) and Whitton et al. (1993), each incorporated herein by reference, may be used to deliver DNA to target cells. Parenteral, mucosal and gene-gun inoculations (Fynan et al., 1993) may be used.

Another approach that may be used capitalizes on the natural ability of viruses to enter cells, bringing their own genetic material with them. Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

A variety of retroviral vectors may be used, e.g., herpes simplex virus U.S. Pat. No. 5,288,641, incorporated herein by reference), cytomegalovirus, and the like, as described by Miller (Miller, 1992). A herpes simplex-thymidine kinase (HS-tK) gene has been delivered to brain tumors using a retroviral vector system, where it successfully induced susceptibility to the antiviral agent ganciclovir (Culver, et al., 1992).

Gene delivery using second generation retroviral vectors has also been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new binding specificity.

Delivery systems such as described above may be used in connection with the present invention. In the context of retroviral treatment, the invention would be used both in the pre-clinical development phase and, also, to monitor gene expression following administration in vivo.

Further methods use other viruses, such as vaccinia virus (Ridgeway, 1988; Baichwal and Sugden, 1986; Coupar et al., 1988); defective hepatitis B viruses (Horwich et al., 1990; Chang et al., 1991); adenovirus and adeno-associated virus (AAV; Muzyczka, 1992; see below), which are engineered to serve as vectors for gene transfer. Although some viruses that can accept foreign genetic material are limited in the number of nucleotides they can accommodate and in the range of cells they infect, these viruses have been demonstrated to successfully effect gene expression. Adenoviruses do not integrate their genetic material into the host genome and therefore do not require host replication for gene expression, making them suitable for rapid, efficient, heterologous gene expression. Adenoviruses and AAV (U.S. Pat. No. 5,139,941, incorporated herein. by reference) are described herein below. Again, the invention would be used in pre-clinical development and during treatment.

The present discoveries may be utilized in conjunction with certain techniques that are well-known in the biological arts and that are further described in the following sections.

Biological Functional Equivalents

As mentioned earlier, modification and changes may be made in the structure of GFP and still obtain a molecule having like or otherwise desirable characteristics. For example, certain amino acids may be substituted for other amino acids in a protein structure without appreciable loss of function. It is thus contemplated that various changes may be made in the sequence of humanized gfp proteins, by virtue of changing the underlying DNA, without appreciable loss of their biological utility or activity.

It is also well understood by the skilled artisan that inherent in the definition of a biologically functional equivalent protein is the concept that there is a limit to the number of changes that may be made within a defined portion of the molecule and still result in a molecule with an acceptable level of equivalent biological activity. For example, it has already been explained that substantially truncated gfp genes are not biologically finctional equivalents.

However, in the context of the present invention, it will also be appreciated that so long as a mutation or change does not result in a GFP protein that has complete loss of fluorescence, the resultant protein will be considered a biologically functional equivalent for the purposes of the invention. Indeed, amino acid replacements that yield proteins with different spectral properties fall within the scope of the invention. This includes mutations within and outside the chromophore region.

Site-Specific Mutagenesis

Site-specific mutagenesis may be used to prepare further variants of humanized gfp genes. Site-specific mutagenesis is a technique useful in the preparation of individual peptides, or biologically finctional equivalent proteins or peptides, through specific mutagenesis of the underlying DNA. The technique further provides a ready ability to prepare and test sequence variants by introducing one or more nucleotide sequence changes into the DNA.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique of site-specific mutagenesis is generally well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes gfp or humanized gfp. An oligonucleotide primer bearing the desired mutated sequence is prepared, generally synthetically, for example by the method of Crea et al. (1978). This primer is then annealed with the single-stranded vector, and subjected to DNA polymerizing enzymes such as $E.\ coli$ polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as $E.\ coli$ cells, and clones are selected which include recombinant vectors bearing the mutated sequence arrangement.

Suitable techniques are also described in U.S. Pat. No. 4,888,286, incorporated herein by reference.

The preparation of sequence variants of the selected humanized gfp gene using site-directed mutagenesis is provided as a means of producing potentially useful GFP species and is not meant to be limiting as there are other ways in which sequence variants of GFP may be obtained. For example, recombinant vectors encoding the desired humanized gfp gene may be treated with mutagenic agents to obtain sequence variants (see, e.g., a method described by Eichenlaub, 1979) for the mutagenesis of plasmid DNA using hydroxylamine.

Although the foregoing methods are suitable for use in mutagenesis, the use of the polymerase chain reaction (PCR™) is generally now preferred. This technology offers a quick and efficient method for introducing desired mutations into a given DNA sequence. The following text particularly describes the use of PCR™ to introduce point mutations into a sequence, as may be used to change the amino acid encoded by the given sequence. Adaptations of this method are also suitable for introducing restriction enzyme sites into a DNA molecule.

In this method, synthetic oligonucleotides are designed to incorporate a point mutation at one end of an amplified segment. Following PCR™, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR™. The 5' end of the oligonucleotides should then be phosphorylated.

The template DNA should be amplified by PCR™, using the oligonucleotide primers that contain the desired point mutations. The concentration of $MgCl_2$ in the amplification buffer will generally be about 15 mM. Generally about 20–25 cycles of PCR™ should be carried out as follows: denaturation, 35 sec. at 95° C; hybridization, 2 min. at 50° C.; and extension, 2 min. at 72° C. The PCR™ will generally include a last cycle extension of about 10 min. at 72° C. After the final extension step, about 5 units of Klenow fragments should be added to the reaction mixture and incubated for a further 15 min. at about 30° C. The exonuclease activity of the Klenow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subclone the fragments and to check the point mutation, one would subdlone the two amplified fragments into an appropriately digested vector by blunt-end ligation. This would be used to transform *E. coli*, from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR™ steps. In this procedure, the two fragments encompassing the mutation are annealed with each other and extended by mutually primed synthesis. This fragment is then amplified by a second PCR™ step, thereby avoiding the blunt-end ligation required in the above protocol. In this method, the preparation of the template DNA, the generation of the oligonucleotide primers and the first PCR™ amplification are performed as described above. In this process, however, the chosen oligonucleotides should be homologous to the template DNA for a stretch of between about 15 and about 20 bases and must also overlap with each other by about 10 bases or more.

In the second PCR™ amplification, one would use each amplified fragment and each flanking sequence primer and carry PCR™ for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art, and are further described in various publications, such as *Current Protocols in Molecular Biology*, 1995, incorporated herein by reference.

Expression Plasmids and Vectors

A wide variety of recombinant plasmids and vectors may be engineered to expresses a humanized gfp genes and so used to deliver GFP to a cell.

As used herein, the term "expression vector" includes any type of genetic construct containing a nucleic acid sequence of a humanized gfp gene in which the nucleic acid sequence is capable of being transcribed in a mammalian or human cell. The expression vectors of the invention should also direct translation into GFP protein, as provided by the invention itself. In addition to the humanized gfp sequence, expression vectors will generally include restriction enzyme cleavage sites and the other initial, terminal and intermediate DNA sequences that are usually employed in vectors to facilitate their construction and use.

Expression vectors for use in mammalian cells ordinarily include an origin of replication (as necessary) and a promoter located in front of the gene to be expressed. A polyadenylation site and transcriptional terminator sequences are preferably included. Ribosome binding sites and RNA splice sites may also be included. An example is the SV40 late gene 16S/19S splice donor/splice acceptor signal.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient. Promoters are discussed below.

Specific initiation signals may also be required for efficient translation. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency. of expression may be enhanced by the inclusion of appropriate transcription elements and transcription terminators (Bittner et al., 1987).

In mammalian expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination. The nature of the polyadenylation signal is not believed to be crucial to the successful practice of the invention, and any such sequence may be employed. SV40, bovine growth hormone gene and signals are convenient and known to function well.

For long-term, high-yield production of recombinant proteins, stable expression is often preferred. Here, rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. The combined use of humanized gfp sequences and selectable markers is therefore also contemplated.

In stable expression, following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk-, hgprt- or aprt- cells, respectively. Also, antimetabolite resistance can be used as the basis of selection for dhfr, that confers resistance to methotrexate (Wigler et al., 1980; O'Hare et al., 1981); gpt, that confers resistance to mycophenolic acid (Mulligan et al., 1981); neo, that confers resistance to the aminoglycoside G-418 (Colberre-Garapin et al., 1981); and hygro, that confers resistance to hygromycin (Santerre et al., 1984).

It is also contemplated that preferred vectors will include an origin of replication functional in bacteria and a typical antibiotic resistance gene, allowing propagation and selection, respectively, in transformed bacterial cells.

In preferred vectors, multiple cloning sites (MCSs) will also be provided at the ends of the GFP coding sequence to facilitate the creation of GFP fusion proteins. The MCS should be present in three different reading frames allowing in-frame fusions to be generated with a convenient restriction site in the gene of interest.

Coordinate expression of different genes from the same promoter in a recombinant vector may be achieved by using an IRES element, such as the internal ribosomal entry site of Poliovirus type 1 from pSBC-1 (Dirks et al., 1993), as described below.

Promoters

Expression vectors comprises protein-encoding nucleic acid segments under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein.

A "promoter" refers to a DNA sequence recognized by the synthetic machinery of a cell, or introduced synthetic machinery, required to initiate the specific transcription of a gene. As used herein, the promoter should be operable in mammalian and human cells. The phrases "operable" and "exerting transcriptional control" mean that the promoter is in the correct location and orientation in relation to the humanized gfp nucleic acid to control RNA polymerase initiation and expression of the humanized gene.

The promoter used to express the humanized GFP is not critical to the present invention. In the examples given, the human cytomegalovirus (CMV) immediate early gene promoter has been used (Thomsen et. al., 1984), which results in the constitutive, high-level expression of the foreign gene. However, the use of other viral or mammalian cellular promoters which are well-known in the art is also suitable to achieve expression of the humanized gfp gene.

A number of viral based expression systems may be utilized, for example, commonly used promoters are derived from polyoma, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, as may the Rous sarcoma virus (RSV) long terminal repeat (LTR).

By employing a promoter with well-known properties, the level and pattern of expression of humanized GFP can be optimized. For example, selection of a promoter which is active specifically in certain cell types will permit tissue-specific expression. Such promoters include those such as the liver fatty acid binding (FAB) protein gene promoter, specific for colon epithelial cells; the insulin gene promoter, specific for pancreatic cells; the transphyretin, α1-antitrypsin, plasminogen activator inhibitor type 1 (PAI-1), apolipoprotein AI and LDL receptor gene promoters, each directing specific or preferential expression in liver cells. Promoters active in brain tissues include the myelin basic protein (MBP) gene promoter, specific for oligodendrocytes; the glial fibrillary acidic protein (GFAP) gene promoter, specific for glial cells; and the neural-specific enolase (NSE) promoter that is specific for nerve cells.

Furthermore, selection of a promoter that is regulated in response to specific chemical or physiological signals can permit inducible expression of the humanized gfp gene. Examples of suitable inducible promoters include the PAI-1, cytochrome P450 gene promoters, heat shock protein genes and hormone inducible gene promoters, and the fos and jun promoters inducible by ionizing radiation.

As mentioned above, inducible promoters are usefull in vivo, e.g., in gene therapy, and in vitro, in screening assays. In screening for the presence of a particular compound within a composition, useful groups of inducible promoters are those activated by heavy metals (Freedman et al., 1993); cytochrome P450 gene promoters, activated by a range of toxic compounds;, heat shock protein gene promoters (Stringhani et al., 1992; Welch, 1993), such as the hsp70 promoter, which are stimulated by various stresses to name a few examples.

IRES

Internal ribosome binding sites (IRES) elements are used to create multigenic or polycistronic messages. IRES elements are able to bypass the ribosome scanning mechanism of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). Any of the foregoing may be used in a humanized gfp vector in accordance with the present invention.

IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. In this manner, multiple genes, one of which will be a humanized gfp gene, can be efficiently expressed using a single promoter/ enhancer to transcribe a single message.

Any heterologous open reading frame can be linked to IRES elements. In the present context, this means any selected protein that one desires to express and any second reporter gene (or selectable marker gene). Even the expression of multiple proteins could be achieved, with concurrent monitoring through GFP production.

AAV Vectors

Adeno-associated virus(AAV) is an attractive vector system for human gene therapy because it is non-pathogenic for humans, it has a high frequency of integration, and it can infect nondividing cells, thus making it useful for delivery of genes into mammalian cells both in tissue culture and in whole animals (Muzyczka, 1992). Recent studies have demonstrated AAV to be a potentially good vector for gene delivery (LaFace, et al. m 1988; Zhou, et al., 1993; Flotte, et al., 1993; Walsh, et al., 1994). Recombinant AAV vectors have been used successfilly for in vitro and in vivo transduction of marker genes (Kaplitt, et al., 1994; Lebkowski, et al., 1988; Samulski, et al., 1989; Shelling and Smith, 1994; Yoder, et al., 1994; Zhou, et al., 1994; Hermonat and Muzyczka, 1984; Tratschin, et al., 1985; McLaughlin, et al., 1988) and genes involved in human diseases (Flotte, et al., 1992; Luo, et al., 1994; Ohi, et al., 1990; Walsh, et al., 1992; Wei, et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued: from the chromosome or from a recombinant plasmid, and a normal productive infection is established (Samulski, et al., 1983; McLaughlin, et al., 1988; Berns, 1990, Kotin, et al, 1990; Muzyczka, 1992). AAV has a broad host range for infectivity (Tratschin, et al., 1984; Laughlin, et al., 1986; Lebkowski, et al., 1988; McLaughlin, et al., 1988).

Typically, recombinant AAV (rAAV) virus is made by cotransfecting a plasmid containing the gene of interest flanked by the two AAV terminal repeats (see FIG. 2B-1, FIG. 2B-2 and FIG. 2B-3 for example, and McLaughlin etal, 1988; Samulski et al., 1989) and an expression plasmid containing the wild type AAV coding sequences without the terminal repeats, for example pIM45 (McCarty et al., 1991). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

rAAV vectors are described in U.S. Pat. Nos. 5,139,941 and 4,797,368, each incorporated herein by reference.

Adenovirus Vectors

Adenovirus vectors, and preferably replication defective vectors, may be used in the context of the present invention. For example, as achieved through the deletion of the viral early region 1 (E1A) region such that the virus is competent to replicate only in cells, such as human 293 cells, which express adenovirus early region 1 genes from their cellular genome. This is important because the virus will therefore not kill normal cells that do not express early gene products. Techniques for preparing replication defective adenoviruses are well known in the art, as exemplified by Ghosh-Choudhury and Graham (1987); McGrory et. al. (1988); and Gluzman et. al. (1982). Rosenfeld et. al. (1991; 1992) and Stratford-Perricaudet et. al. (1990; 1992) also describe uses of adenovirus.

Other than the requirement that the adenovirus vector be replication defective, the nature of the adenovirus vector is not believed to be crucial. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, it has historically been used for most constructions employing adenovirus as a vector, and it is non-oncogenic.

In that the vectors for use in these aspects are replication defective, they will typically not have an adenovirus E1 region. Thus, it will be most convenient to introduce the humanized gfp gene at the position from which the E1 coding sequences have been removed. However, the position of insertion of the humanized gene within the adenovirus sequences is not critical. The humanized transcriptional unit may also be inserted in lieu of the deleted E3 region in E3 replacement vectors as described previously by Karlsson et. al. (1986).

Expression Kits

Expression kits comprising humanized gfp genes form another aspect of the invention. Such kits will generally contain, in suitable container means, a formulation of a humanized gfp gene or a vector capable of expressing a humanized gfp gene. The gene or vector may be provided in a pharmaceutically acceptable formulation.

When the components of the kit are provided in one or more liquid solutions, the liquid solution is an aqueous solution, with a sterile aqueous solution being particularly preferred. The humanized gfp gene or vector may also be formulated into a syringeable composition. In which case, the container means may itself be a syringe, pipette, eye dropper, or other such like apparatus, from which the formulation may be applied to a cell, or to an area of the body, or injected into an animal, or applied to and mixed with other components of a kit.

However, the components of the kit may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the humanized gfp gene or vector may be placed, preferably, suitably allocated. A second humanized gfp gene or vector construct may also be provided, wherein the kit will also generally contain a second vial or other container into which this is be placed. The kits may also comprise a second/third container means for containing a sterile, pharmaceutically acceptable buffer or other diluent.

The kits of the present invention will also typically include a means for containing the vials in close confinement for commercial sale, such as, e.g., injection or blow-molded plastic containers into which the desired vials are retained.

Irrespective of the number or type of containers, the kits of the invention may also comprise, or be packaged with, one or more further molecular biological reagents, such as restriction enzymes.

Recombinant Expression

Desired clones may be incorporated into an expression system with humanized gfp for recombinant expression. It is believed that virtually any eukaryotic expression system may be employed in this manner. Transformation of host cells with DNA segments encoding a selected protein and humanized gfp will provide a convenient means of monitoring expression. Both cDNA and genomic sequences are suitable for eukaryotic expression, as the host cell will generally process the genomic transcripts to yield functional mRNA for translation into protein.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the possibility of employing genomic versions of particular genes is not excluded.

As noted above, it is proposed that different proteins may be co-expressed and monitored in the same cell using different colored humanized GFPs. This may be achieved by co-transfecting the cell with two distinct recombinant vectors, each bearing a copy of the humanized gfp linked to a particular protein-encoding DNA. Alternatively, a single recombinant vector may be constructed to include both such coding regions which could then be expressed in cells transfected with the single vector.

Recombinant Host Cells The terms "engineered" and "recombinant" cells are intended to refer to a cell into which an exogenous DNA segment or gene that includes a humanized gfp gene sequence has been introduced. Therefore, engineered cells are distinguishable from naturally occurring cells which do not contain a recombinantly introduced exogenous DNA segment or gene. Engineered cells are thus cells having a gene or genes introduced through the hand of man.

Established cell lines that grow continuously in culture form one group of cells that may be used in connection with the present invention. Examples of such mammalian host cell lines that are particularly contemplated for use are VERO cells, HeLa cells, Chinese hamster ovary (CHO) cell lines, COS cells, such as COS-7, W138, BHK, HepG2, 3T3, RIN, MDCK, A549, PC12, K562 and 293 cells.

Primary cell lines are also contemplated for use with this invention. Primary cell lines are those cells that have been removed from an animal or human subject and are capable of surviving in culture for a limited period of time. Such cells are often manipulated, e.g., to introduce a beneficial gene, and then re-introduced into the animal from which they were originally obtained. This technique is often termed ex vivo gene therapy.

Primary cells of all vertebrate species are considered for use with the humanized gfp genes disclosed herein, whether or not they are returned to the body of an animal. These include. by way of example only, bone marrow cells, nerve cells, lung epithelial cells and hepatocytes.

Humanized gfp-containing cells within the body that have been previously engineered to express, secrete or otherwise deliver therapeutic or desired agents to an animal or human subject are also encompassed within the cells of the invention, whether or not they were originally derived from the animal. Cells that were not so-obtained from the ultimate host animal may be cells from an immunologically compatible animal, cells that have been immunologically modified or disabled, cells that are protected within a semi-permeable device in the host animal and even largely unmodified cells that are intended to have a temporary life span within the host animal.

Of course, it will be understood that as the present invention is well suited for use in more direct gene therapy methods, any target cell of the body can contain a humanized gfp gene as described in this invention. All such cells are considered to fall within the description of a "recombinant host cell", as used herein. This includes any cell within an animal or human subject that comprises one or more copies of a humanized gfp gene or vector, irrespective of the manner in which the cell acquires the gene, e.g., by transfection, infection and the like. Diseased cells, deficient cells and healthy cells are all encompassed within the invention in this manner.

Cloning other gfp Genes

It is also contemplated that gfp genes from other organisms may be cloned. These may have improved or otherwise desirable spectral properties and may be then be humanized in accordance with the present invention.

Cloning a DNA molecule encoding a GFP-like protein from another organism would simply require screening a DNA library to obtain a specific DNA molecule and purify it to render it distinct from other portions of DNA. The first step in such cloning procedures is the screening of an appropriate DNA library. The screening procedure may be an expression screening protocol, e.g., employing antibodies directed against the GFP protein, or activity assays based upon fluorescence.

Alternatively, screening may be based on the hybridization of oligonucleotide probes, designed from a consideration of portions of the known gfp DNA sequences. The operation of such screening protocols are well known to those of skill in the art and are described in detail in the scientific literature, for example, in Sambrook et al. (1989), incorporated herein by reference.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example I

Low Expression of Jellyfish GFP in 293 Cells

This example describes attempts to use recombinant AAV (rAAV) that expresses a jellyfish gfp10 reporter gene in transfection and expression in 293 cells.

Generation of AAV vectors and rAAV expressing wild type gfp

Adeno-associated virus (AAV) is now widely used as a vector to deliver genes into different cell types. There are many advantages of using AAV including the apparent absence of pathogenicity, high viability of virion, site-specific integration, long-term expression of the delivered gene and relative independence of infectivity from host chromosome replication and cell cycling.

One disadvantage of AAV is a limiting packaging size of the viral DNA, which can not exceed 5,000 nucleotides. Most AAV vectors currently available carry one or another reporter genes, namely E. coli β-galactosidase and neomycin phosphotransferase. Both of these reporter genes are quite bulky and occupy too much of the limited space of the AAV genome. Detection protocols for these gene products are clumsy and cumbersome.

Figures 2, 2A:
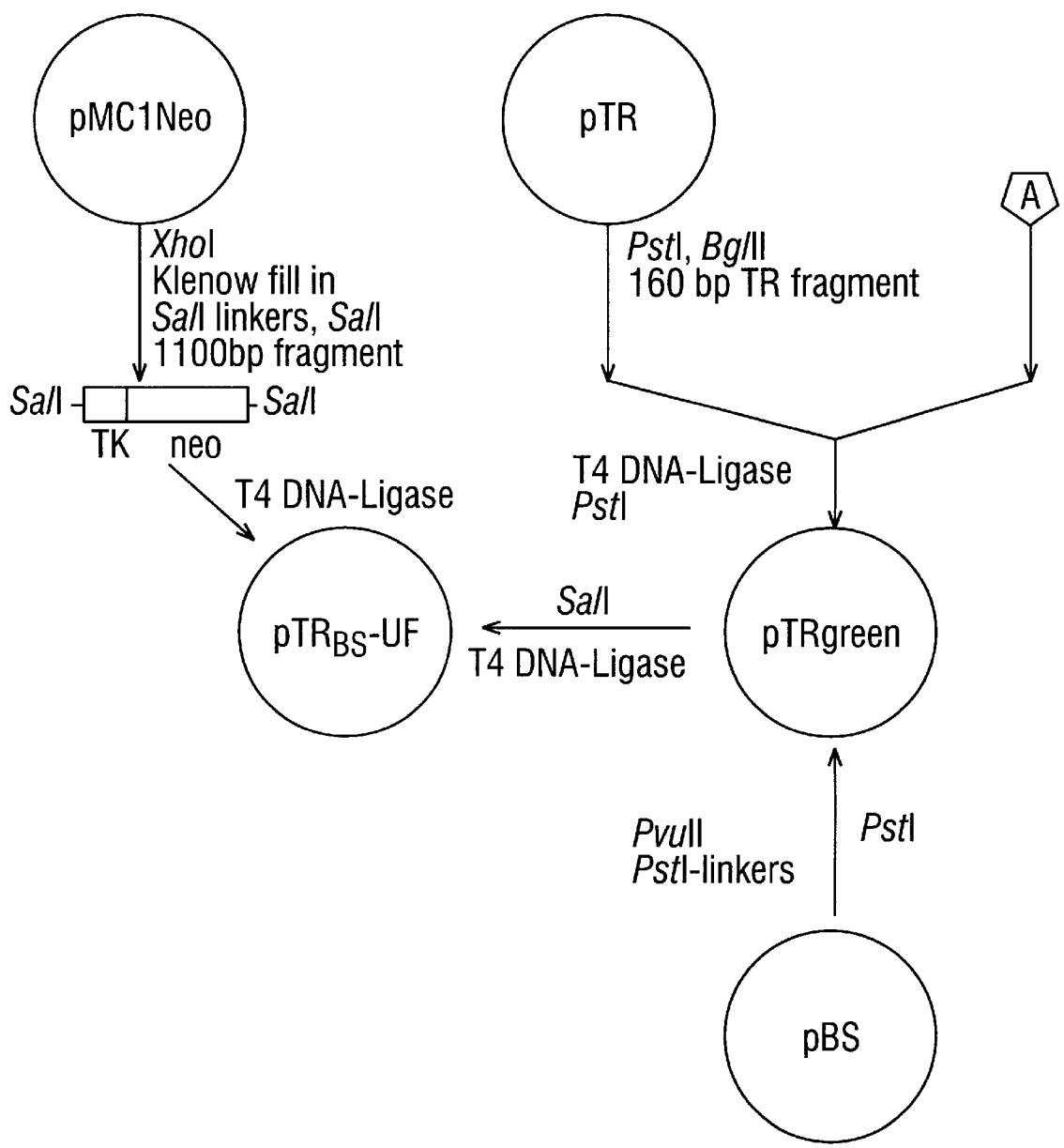
Figures 1, 2B:
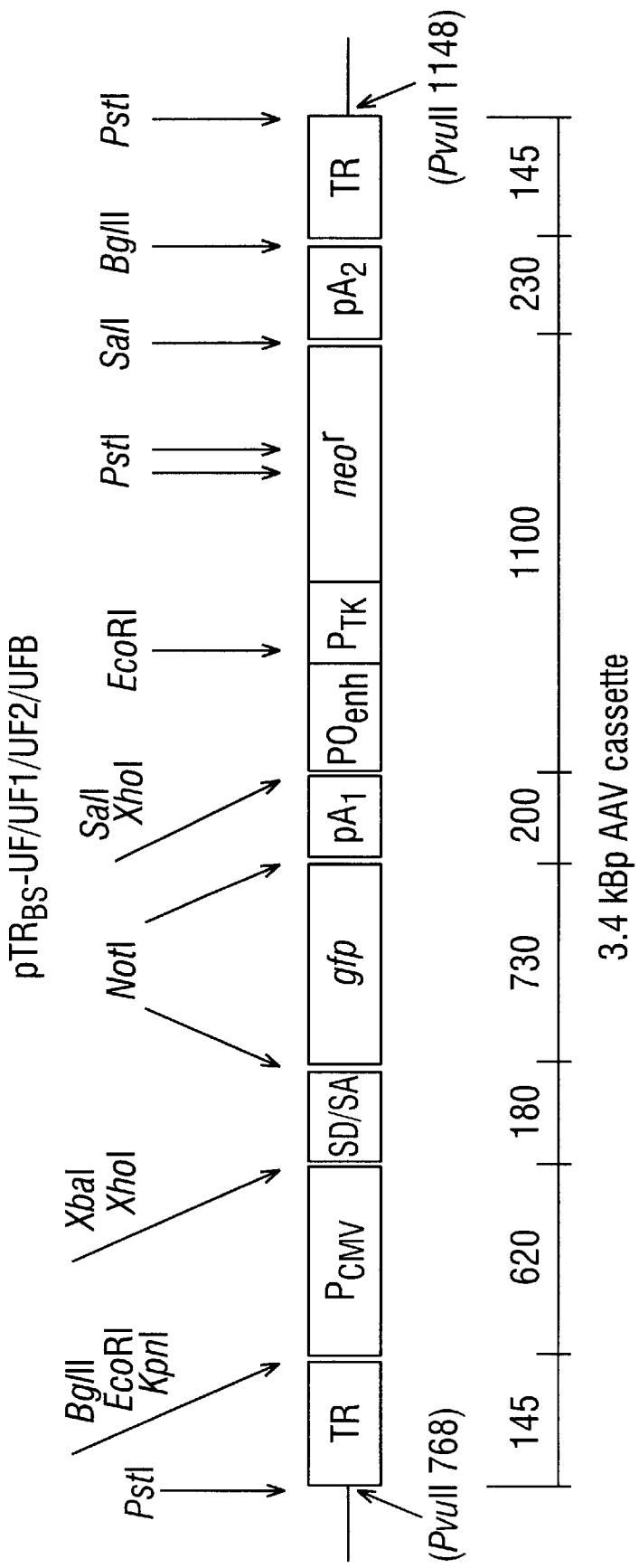
Figures 2, 2B:
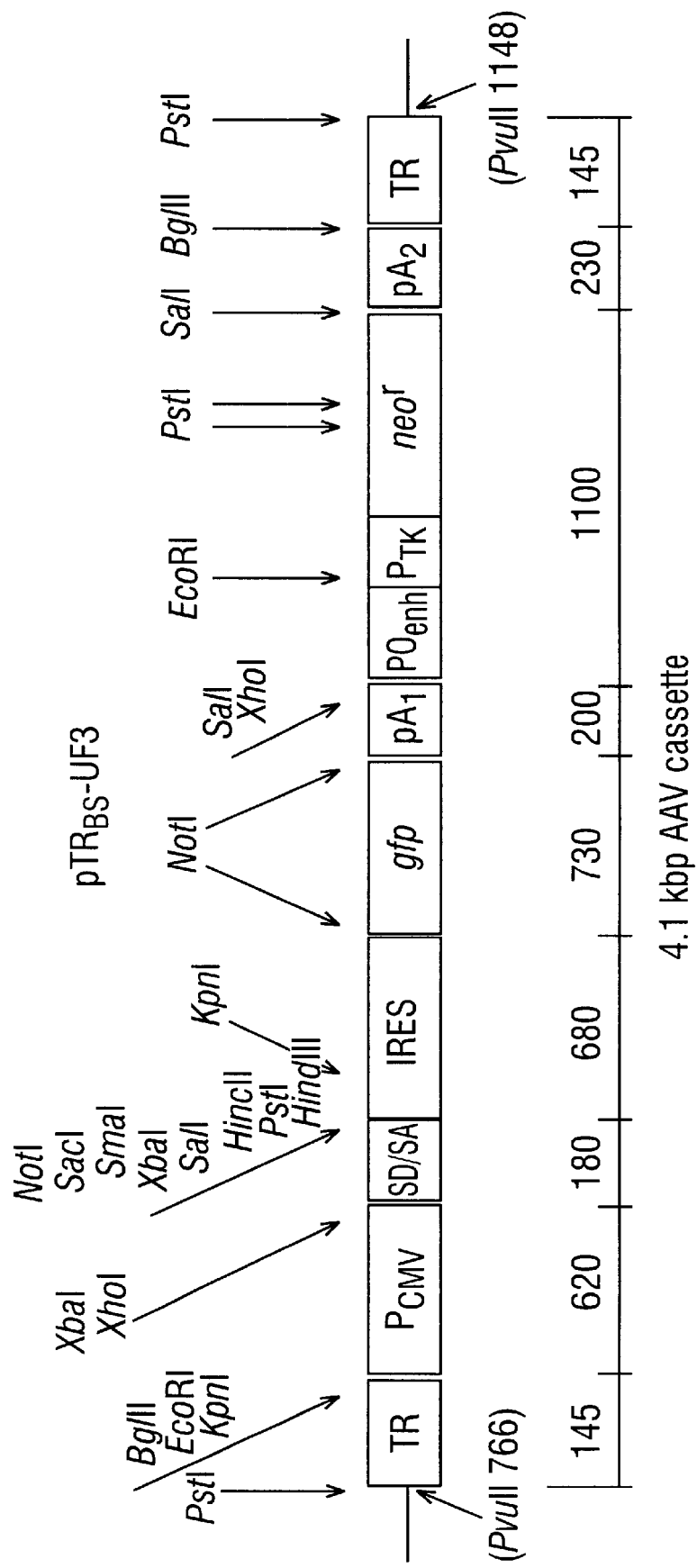

This section describes the construction of a recombinant AAV vector plasmid, $PTR_{BS}$-UF (FIG. 2A-1 and FIG. 2A-2), which carried both the jellyfish gfp10 gene and neoR gene. The plasmid TU#65 (Ward et al., 1994) was used as the source of the gfp10 coding sequence and the gene was placed under the control of the immediate early CMV promoter. A schematic diagram of vector generation is shown in FIG. 2A-1 and FIG 2A-2.

Briefly, the gfp10 sequence was subcloned into the NotI site of pCMVβ (Clontech) after digesting the parent plasmid TU#65 (Chalfie et. al., 1994) with AgeI and EcoRI, filling in the ends with Klenow fragment and adding NotI-linkers. The resulting plasmid, designated pCMV green was then used as a template to amplify in a PCR reaction the transcription cassette containing the CMV promoter, the SV40 intron, the gfp10 cDNA and the SV40 polyadenylation signal.

The upstream PCR primer complementary to the CMV promoter, also included an overhang that contained the BglII, EcoRI, and KpnI sites. The downstream PCR primer, complementary to the polyadenylation signal, included a SalI site overhang. The polyadenylation signal of the bovine growth hormone (bGH) gene was amplified in another PCR reaction using the plasmid pRc/CMV (Invitrogen) as the template. The upstream primer in this reaction contained a SalI site sequence overhang and the downstream primer contained a BglII site.

After purification of the PCR products on a 1% agarose gel, the respective fragments were digested with SalI and ligated to each other via the exposed SalI ends. The ligation product was gel purified and digested with BglII. The 160 bp BglII-PstI fragment, containing the AAV terminal repeat, was isolated by gel purification from the plasmid pTRBR(+) (Ryan et al., 1995). This fragment had been subcloned into pTR$_{BR}$(+) from the previously described plasmid dl3-94 (McLaughlin et al., 1988). It was then ligated to both ends of the BglII-digested cassette, containing the CMV promoter, SV40 intron, gfp10 cDNA, SV40 poly(A) and bPH poly(A).

The ligation product was then cut with PstI and subcloned into plasmid pBS(+) (Stratagene), which had been modified by converting the PvuII sites at 766 and 1148 into PstI sites by adding PstI-linkers and deleting the internal 382 bp fragment, containing the polylinker region. The resulting plasmid was designated pTRgreen.

The neo-resistance gene cassette, driven by the HSV thymidine kinase gene promoter and the enhancer from polyoma virus was obtained from the plasmid pMC1neo (Stratagene) by cutting the plasmid with XhoI, filling in the end with Klenow, adding SalI-linkers, and by digesting with SalI. The DNA fragment containing the neo cassette was gel purified and subcloned into the SalI site of pTRgreen, digested with SalI. The resulting construct, pTR$_{BS}$-UF is shown in FIG. 2A-1 and FIG. 2A-2.

To generate recombinant AAV (rAAV) virus, 293 cells were co-transfected with PTR$_{BS}$-UF and the helper plasmid pIM45, carrying the wt AAV genome without terminal repeats (McCarty et al., 1991). The same cells were also infected with adenovirus at a multiplicity of infection (m.o.i.) of 10.

Recombinant AAV was harvested after 60 h by freezing and thawing cells three times, heat-inactivating Ad for 30 min. at 56° C., spinning down cell debris and purifying the virus through a CsCl gradient (1.40 g/ml) formed in a SW41 rotor for 48 hrs at 200,000 g. The gradient was fractionated and the density was determined by refractometry. Fractions with densities between 1.38 and 1.4 g/cm$^3$ were pooled and dialyzed against DMEM media for 4 h. The AAV titer was determined by the infectious center assay (McLaughlin et. al., 1988).

Low level expression of wild type gfp

Figures 2, 2B, 3:
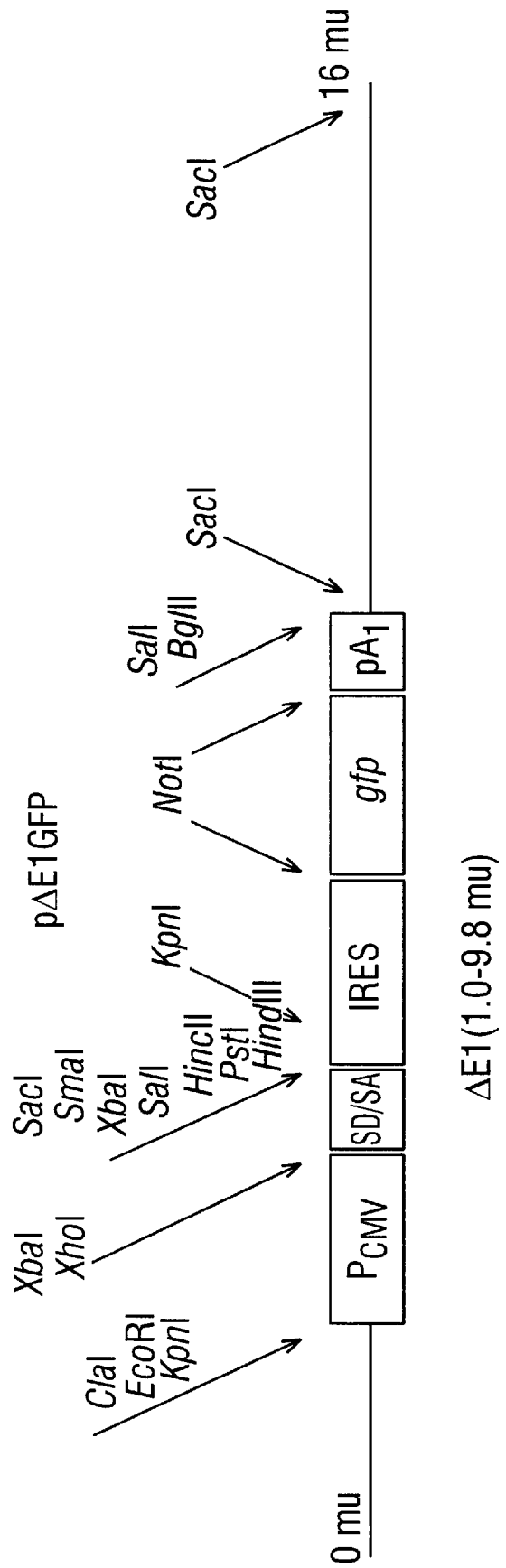
Figure 3:
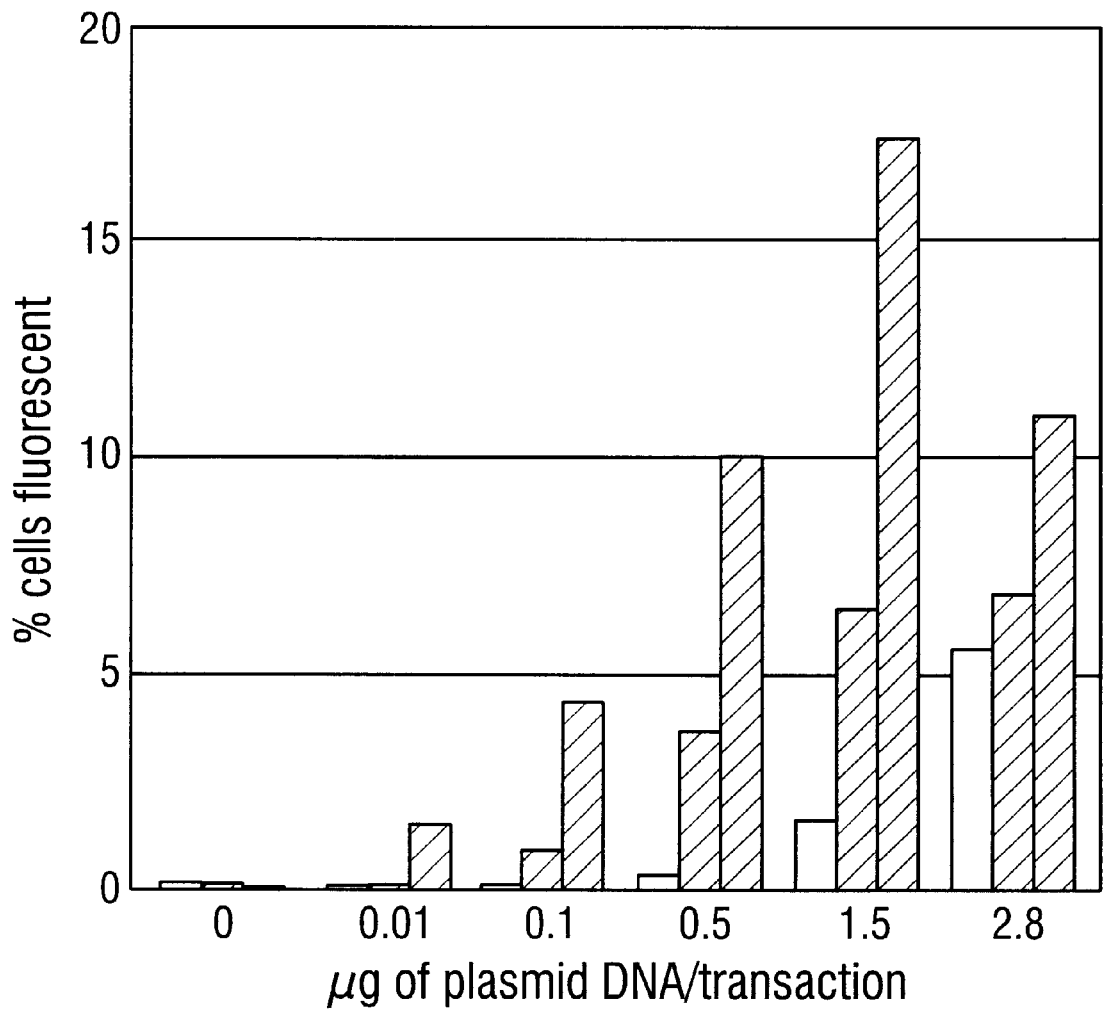

When PTR$_{BS}$-UF plasmid DNA was transfected into 293 cells, the average number of cells expressing GFP was usually less than 5% (FIG. 3). Furthermore, 293 cells infected with the recombinant AAV, carrying the same GFP expression cassette, were repeatedly scored as GFP-negative. The only difference between these two studies was apparently the number of GFP cDNAs delivered into each cell. During the transfection, hundreds or even thousands of plasmid copies are being delivered, whereas infection under conditions of low m.o.i. (less than 1) delivers only a single copy of a gene.

The inventors thus found that the gfp10 cDNA, as originally described by Chalfie et al. (1994), was a poor reporter when expressed in primate and human cells. Clearly, new techniques were required by which the expression of gpf10 in mammalian and human cells could be enhanced.

Example II
Attempts to Increase GFP Expression in Human Cells

The present example describes various methods that could be used in an attempt to increase the expression of gpf10 in mammalian and human cells.

There are several potential ways to boost the amount of desired gene product which is under control of a given promoter. One such method is to try to increase the stability of mRNA by introducing an intron sequence which directs the pre-mRNA into the processing/splicing pathway through the protein/RNA interactions and transport.

The GFP expression cassette of the present inventors' contained the sequence of the SV40 late gene 16S/19S splice donor/splice acceptor signal (FIG. 1B). This sequence is often employed in the literature, but its effects can be variable and gene-specific. The inventors thus reasoned that this technique alone would not significantly increase GFP expression in human cells.

It is also conceivable to increase the stability of an alien protein by fusing it to another protein or polypeptide domain. In this regard, vectors allowing fusion of the jellyfish sequence to a second coding region are available. However, the inventors did not believe that this would adequately substitute for the defects of the gfp sequence.

Another possible way to increase the protein yield is to maximize the translation efficiency by introducing sequences that facilitate initiation of translation of eukaryotic MRNA. One such sequence, immediately preceding the AUG initiator codon, is the Kozak consensus sequence (GCC)GCCA/GCC<u>ATG</u> (SEQ ID NO:8; Kozak, 1987)). Additionally, an optimally positioned stem-loop hairpin structure, located about 14 nucleotides downstream of the AUG codon, could be used (Kozak, 1990).

However, studies are known in which a Kozak sequence placed upstream of gfp10 did not significantly change the expression efficiency. Therefore, despite the general usefulness of the Kozak sequence, and the specific suggestions of the prior art to use the Kozak sequence in conjunction with gfp (see, e.g., PCT application WO 95/07463), introduction of the Kozak sequence upstream of gfp10 does not appear to have been particularly successful.

The inventors reasoned that any increase in initiation that may be afforded by the Kozak sequence would not yield a significant increase in gfp10 expression as translation would still be limited. This drawback was thought to severely limit the usefulness of the Kozak sequence alone, although it was considered that benefits may result upon combination of the Kozak sequence with another method directed to addressing the translation efficiency problem.

Example III
Design of Humanized GFP

In light of the failure of the foregoing well-used techniques to improve GFP expression in mammalian cells, the inventors hypothesized that one of the important reasons for the low expression of GFP in such cells was the poor translation efficiency of the mRNA in the cell environment. The present example describes the design of a humanized GFP for use in obtaining increased GFP expression in mammalian and human cells.

Low expression of proteins can result from a poor translation efficiency of an mRNA species in certain cells. For example, the human cell environment is characterized by a particular set of isoacceptor tRNAs, which are different in other species. Indeed, it is generally known that the choice of synonymous codons in both prokaryotic and eukaryotic genes is strongly biased. Also, there exist clear similarities in codon usage among different genes of the same or taxonomically related organisms, regardless of the functions of the genes or the dissimilarities among the genes (even among those encoding cognate proteins) of taxonomically distant organisms (Grantham et al., 1991; Ikemura, 1980; Ikemura et al., 1981).

The differences in codon-choice patterns between the organisms have been attributed to differences in the actual populations of isoacceptor tRNAs and to differences in modified nucleotides at the anticodon wobble position (Ikemura et al., 1981; Ikemura et al., 1982). The synonymous codon choices do not affect the nature of the protein synthesized but may relate to the expressivity of the gene (Bennetzen and Hall, 1982; Ikemura et al., 1981; Ikemura et al., 1981; Ikemura et al., 1982). The extent of the correlation between codon usage and tRNA content has been found to relate to the production levels of individual genes.

Therefore, the present inventors investigated the codon usage frequencies of the jellyfish gfp10 and compared it to the average mean of those summed for 1490 human genes (Wada et al., 1990). An analysis of the sequence of gfp10 cDNA showed that the codon usage frequencies of this jellyfish gene are quite different from those prevalent in the human genome. For example, Leu amino acid residues at the positions 18, 53, 125, 178, 195 and 236; Ser at position 208; and Val at positions 93, 150 and 224 of the jellyfish GFP (SEQ ID NO:2) are encoded by triplets which are almost never used in human genes (codons in SEQ ID NO:1). The rest of the amino acids also display a bias different from human, though not as dramatic.

Therefore, as the inventors reasoned that the mRNA coding for the jellyfish GFP is translated with low efficiency in a human cell system, yielding insufficient amounts of the protein for visual detection of fluorescence, the inventors designed a synthetic version of the jellyfish gfp10. In this synthetic, or humanized, version of gfp10, codons preferentially used in the human genome were inserted to replace those rare or less frequently used codons present in the original gfp10.

Example IV
Construction of Humanized GFP Gene and Vectors

This example describes the production of a humanized GFP for use in increased expression in mammalian and human cells, using the results of the analyses described in Example III.

A total of 92 base substitutions were made in 88 codons without changing the amino acid sequence (FIG. 1A, FIG. 1B and FIG. 1C). In addition, the sequence immediately preceding the start codon for the GFP protein in pTR$_{BS}$-UF1 was modified to produce a Kozak consensus sequence. Also, codon 80 was reverted back to a wild type glutamine residue (Prasher et al., 1992), as compared to arginine, as described by Chalfie et al. (1994). This construct, termed pTR$_{BS}$-UF1, was prepared as follows.

The gfp cDNA was synthesized by assembling mutually priming synthetic oligonucleotides (see FIG. 1A, FIG. 1B and FIG. 1C). The gfp10 gene was divided into 8 segments of approximately equal length and 4 pairs of oligonucleotides were synthesized, each pair consisting of two overlapping oligos with a short stretch of overlap (FIG. 3, underlined), one coding for the sense strand, the other for the antisense. After annealing and extension with Sequenase, pairs 1 and 2 were digested with EaeI, whereas pairs 3 and 4 were digested with BamHI. The digested products were then ligated in two separate reactions: oligos 1 to 2 and oligos 3 to 4. Ligation products of the desired length were purified on a 5% polyacrylamide gel under nondenaturing conditions. Both DNA fragments were then digested with EcoRII and ligated to each other.

The final product was amplified in a PCR™ reaction, using a pair of oligonucleotides, partially complementary to the humanized gfp cDNA (see below, bold type letters) and containing the restriction sites NotI, XbaI and HindIII (see below, underlined) for cloning. The sequence of the upstream primer, which included a Kozak consensus sequence (Kozak, 1987) and that of the downstream primer, respectively, are shown:

5'-TGC<u>TCTAGA</u>GCGGCCGCCGCCACCATGAGCAAGGGCGAGGAACTG-3'
(SEQ ID NO:9);
5'-CGG<u>AAGCTT</u>GCGGCCGCTCACTTGTACAGCTCGTCCAT-3' (SEQ ID NO:10).

After digestion of the PCR product with XbaI and HindIII the DNA fragment was cloned into pBS(+) (Stratagene) and sequenced. Several independent clones were isolated and sequenced. These clones had mutations in the coding sequence which presumably occurred either during PCR amplification or were present in the oligonucleotides. Portions of these clones were then spliced together to produce the final gfp$_h$ gene that contained a wild type amino acid sequence. The resulting constructs was designated pBS-GFP$_H$1 and contained the coding sequence for wild type GFP.

To construct pTR$_{BS}$-UF1, the inventors substituted the NotI fragment of pBS-GFP$_H$1 (wild type) for the NotI fragment of PTR$_{BS}$-UF (FIG. 2A-1 and FIG. 2A-2).

To generate recombinant AAV (rAAV) virus, 293 cells were co-transfected with PTR$_{BS}$-UF1 and the helper plasmid pIM45, carrying the wt AAV genome without terminal repeats (McCarty et al., 1991). The same cells were also infected with adenovirus at a multiplicity of infection (m.o.i.) of 10.

Recombinant AAV was harvested after 60 h by freezing and thawing cells three times, heat-inactivating Ad for 30 min. at 56° C., spinning down cell debris and purifying the virus through a CsCl gradient (1.40 g/ml) formed in a SW41 rotor for 48 his at 200,000 g. The gradient was fractionated and the density was determined by refractometry. Fractions with densities between 1.38 and 1.4 g/cm$^3$ were pooled and dialyzed against DMEM media for 4 h. The AAV titer was determined by the infectious center assay (McLaughlin et. al., 1988).

Example V
Construction of Humanized GFP Variants and rAAV Vectors

This example describes the production of a further humanized GFP sequences encoding GFP protein variants with different properties to the wild type protein. The variants also have increased expression in mammalian and human cells.

Two mutants were constructed in the pBS-GFP$_h$ background by site-directed PCR™ mutagenesis. A first humanized mutant mirrors the protein sequence reported by Heim et al. (1995) who described a Ser65 to Thr65 substitution that increased the fluorescence yield in the context of the original jellyfish codon sequence. Reasoning that this mutation might be even more effective in the context of the humanized pTR$_{BS}$-UF1 sequence, the inventors reproduced this point mutation in the PTR$_{BS}$-UF1 background to produce plasmid pTR$_{BS}$-UF2.

As a further step in providing enhanced fluorescence, an additional mutation was effected to produce an "enhanced" green version of hGFP. In addition to the Ser65 to Thr65 substitution, Leu was substituted for Phe64. The enhanced hGFP thus was substituted with Leu64 in place of Phe64 where TTC encoding Phe was converted to CTG and also where Ser65, encoded by TCT was converted to Thr encoded by ACC.

Another point mutation, Tyr66 to His66, which resulted in blue fluorescence (Heim et al., 1994) also was built into the humanized background of pTR$_{BS}$-UF1 to produce the vector pTR$_{BS}$-UFB.

An "enhanced" blue version was created by further converting Tyr145 to Phe145 in addition to the Tyr66 to His66 mutation. The base conversions were TAT to TTC and TAT to CAT respectively.

The modified versions of hGFP have a wide range of applications, particularly in the use of enhanced versions of the different colours. Mutated GFP and BFP (blue fluorescent protein) have different excitation and emission spectra with no overlap, thereby allowing independent detection. Dual tagging permits rapid and specific identification of cells that express either of two or more fluorescently labeled proteins. Such methods are applicable to drug screening, for example, or analysis of agents that affect a target gene placed under the control of a constitutive promoter. Applications may also include study of gene expression under various stimuli or as affected by inhibitors.

To create the mutants, PCR™ reactions were performed, using pBS-GFP1 as a template and a pair of oligos, as defined below:

To construct pTR$_{BS}$-UF2 or pTR$_{BS}$-UFB, the inventors substituted the NotI fragment of pBS-GFP$_H$2 (Thr$_{65}$) or PBS-GFP$_H$B (His$_{66}$), respectively, for the NotI fragment of PTR$_{BS}$-UF (FIG. 2A-1 and FIG. 2A-2). Any DNA fragment that had undergone PCR amplification was sequenced to confirm the identity of the original sequence.

To construct pTR$_{BS}$-UF3 the EcoRI site of the plasmid pSBC-1 (Dirks et al., 1993) was converted into a NotI site after digestion with EcoRI, filling in the 5'-overhang with Klenow polymerase and ligation of NotI linkers. The 680 bp NotI fragment, consisting of a polylinker and the internal ribosome entry site (IRES) element of poliovirus type 1 was then subcloned into one of the NotI sites of pTR$_{BS}$-UF2 (FIG. 2A-1 and FIG. 2A-2).

To generate recombinant AAV (rAAV) virus, 293 cells were transfected with pTR$_{BS}$-UF2 or pTR$_{BS}$-UF3, and co-transfected with the helper plasmid pIM45, carrying the wt AAV genome without terminal repeats (McCarty et al., 1991). The same cells were also infected with adenovirus at a multiplicity of infection (m.o.i.) of 10.

Recombinant AAV was harvested after 60 h by freezing and thawing cells three times, heat-inactivating Ad for 30 min. at 56° C., spinning down cell debris and purifying the virus through a CsCl gradient (1.40 g/ml) formed in a SW41 rotor for 48 hrs at 200,000 g. The gradient was fractionated and the density was determined by refractometry. Fractions with densities between 1.38 and 1.4 g/cm$^3$ were pooled and dialyzed against DMEM media for 4 h. The AAV titer was determined by the infectious center assay (McLaughlin et. al., 1988).

Recombinant AAV vector plasmids pTR-UF2, as well as pTR-UFB which is the progenitor of plasmid pTR-UF1 and pTR-UF5, are described in previous examples.

Construction of recombinant AAV vector plasmid pTR-UF1 containing humanized GFP gene that encodes a wild-type GFP protein is described in Examples I–V.

Construction of recombinant AAV vector plasmid pTR-UF2 containing the humanized GFP gene that encodes a GFP protein variant with different proerties from the wild-type GFP protein is described in this example. The, humanized GFP gene contained in plasmid pTR-UF2 has a point mutation, Ser65 to Thr65.

Example VI
Increased Expression of Humanized GFP

The present example describes the increased expression of GFP that resulted from expressing the humanized GFP in 293 cells.

To compare the expression efficiency of the humanized gfp constructs with the original jellyfish sequence the inven-

```
For GFP2:
#1: upstream primer; as described in Example IV;
#2: 5'-GCTTCATATGGTCTGGGTATCTGGAAAAGCACTGCACGCCATACCAGAAGGTAG-3'   (SEQ ID NO:11);

For GFPB:
#1: upstream primer; as described in Example IV;
#2: 5'-GCTTCATATGGTCTGGGTATCTGGAAAAGCACTGCACGCCATGAGAGAAGGTAG-3'   (SEQ ID NO:12)
```

To make the mutants, the PCR™ product was digested with NdeI and XbaI and substituted for the respective fragment of pBS-GFP1. The sequence was confirmed by sequencing the NotI-fragment, containing the mutant GFP cDNA, which was substituted for the NotI-fragment in pTR-UF 1.

Although it is not believed to affect expression, in the mutants of humanized GFP, the inventors have again reverted codon 80 back to a wild type glutamine residue (Prasher et al., 1992), as compared to arginine, as described by Chalfie et al. (1994).

tors transfected 293 cells with pTR$_{BS}$-UF, pTR$_{BS}$-UF1, or pTR$_{BS}$-UF2 plasmid DNA at various DNA concentrations. The transfected cells were then analyzed by FACS 36 hr after transfection (FIG. 3).

To monitor fluorescence, 293 cells were infected with CsCl-purified rAAV-GFP$_H$2 at an M.O.I. of 10. At 36 hrs postinfection, the cells were photographed in a fluorescence microscope using a CHROMA Filter Cube #41014 GFP-HQ (excitation at 450+/−25 nm). Alternatively, after infection at an M.O.I. of 1 and selection with G418 for two weeks, three independent observers scored the number of green fluorescent cells within the G418 colonies by fluorescent microscopy. The mean of the frequencies obtained by the three observers was calculated. At least 11,500 cells in 150 separate colonies were scored for each viral preparation, rAAV-GFP$_J$, rAAV-GFP$_H$1 and rAAV-GFP$_H$2.

Results from these studies revealed that pTR$_{BS}$-UF1 carrying the humanized gfp sequence consistently produced 5–10 times higher number of cells scored as positive for green fluorescence than the jellyfish sequence. The point mutation in pTR$_{BS}$-UF2 increased the number of fluorescent cells by an additional 5–10 fold over pTR$_{BS}$-UF1.

At relatively low plasmid DNA concentrations, the difference between pTR$_{BS}$-UF2 and PTR$_{BS}$-UF was greater than 70 fold. At higher concentrations of transfected plasmid DNA, the difference in the number of cells expressing GFP was reduced. This result was consistent with the idea that the inability to translate the jellyfish gfp sequence could be overcome in part by increasing the gene copy number.

Figure 4A:
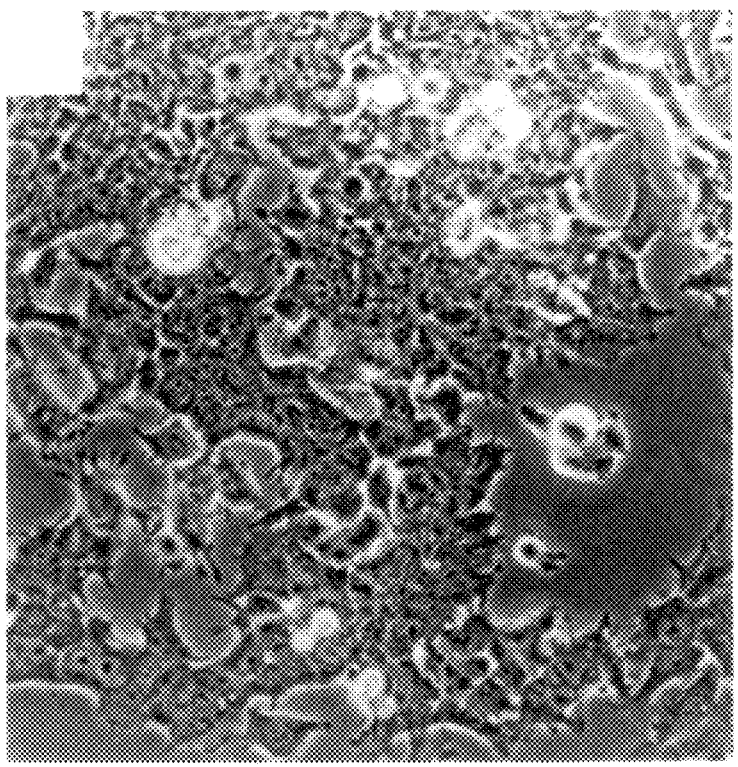
FIG. 4A and FIG. 4B. Expression of rAAV-$GFP_H2$ in 293 cells. 293 cells were infected with CsCl-purified rAAV-$GFP_H2$ at an M.O.I. of 10. 36 hrs postinfection cells were photographed in a fluorescence microscope using a CHROMA Filter Cube #41014 GFP-HQ (excitation at 450+/−25 nm).
Figure 4B:
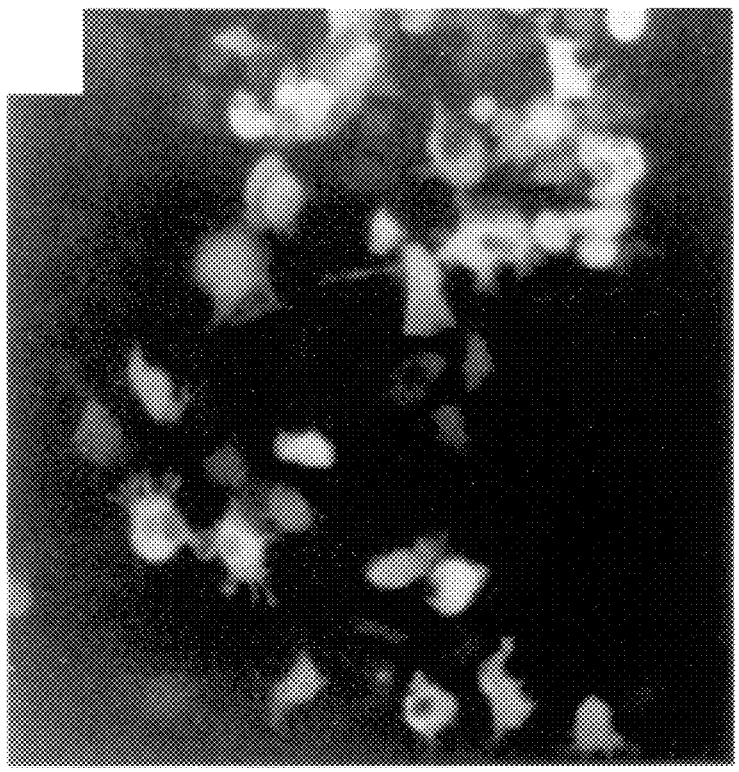
Figure 5A:
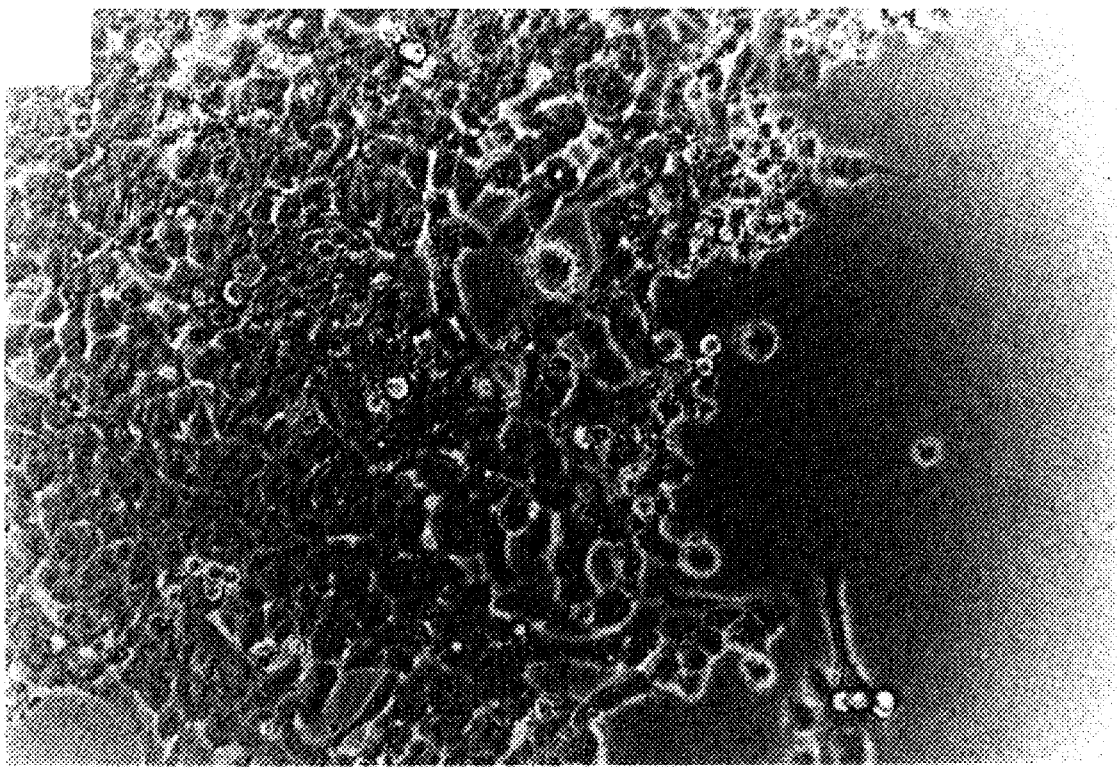
FIG. 5A, FIG. 5B, FIG. 5C and FIG. 5D. Fluorescence of G418-resistant clones containing rAAV-$GFP_H2$ provirus. 293 cells were infected with CsCl-purified rAAV-$GFP_H2$ at an M.O.I. of 1. 48 hrs postinfection cells were split and plated at a low (less than 10%) confluency. 18 hrs later G418 was added at a final concentration of 200 mg/ml. The media was changed every 4 days and G418 resistant colonies were photographed after 14 days of selection.
Figure 5B:
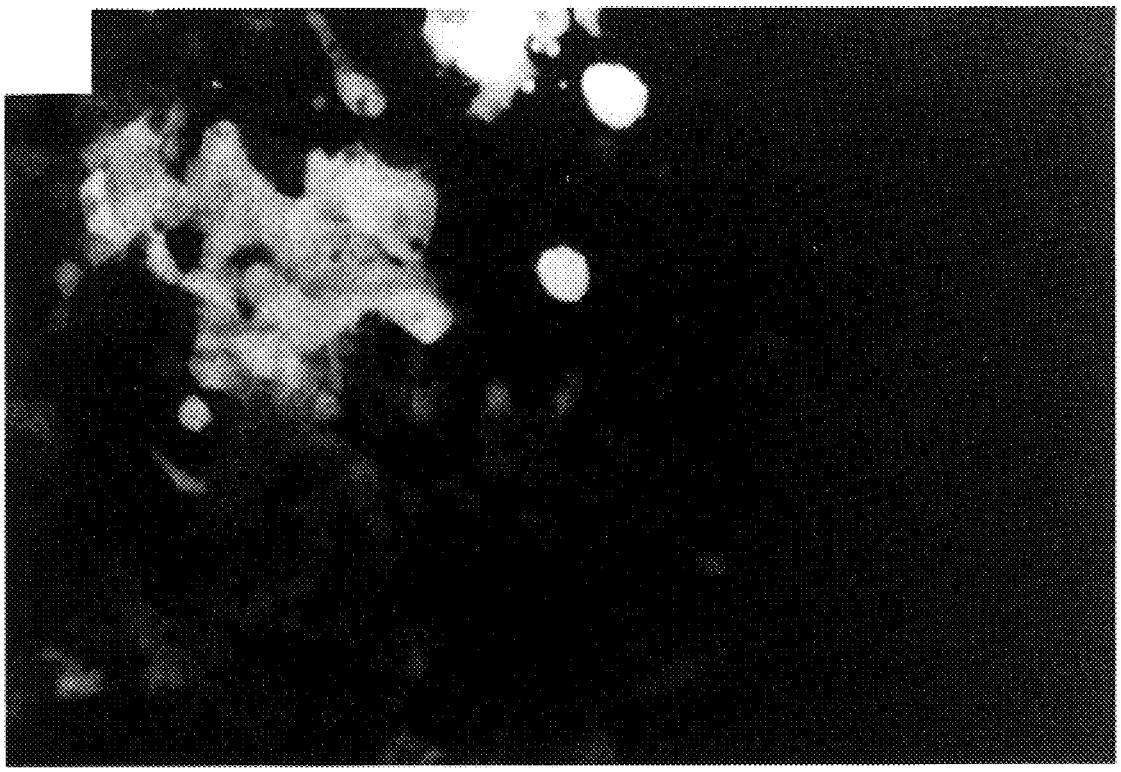
Figure 5C:
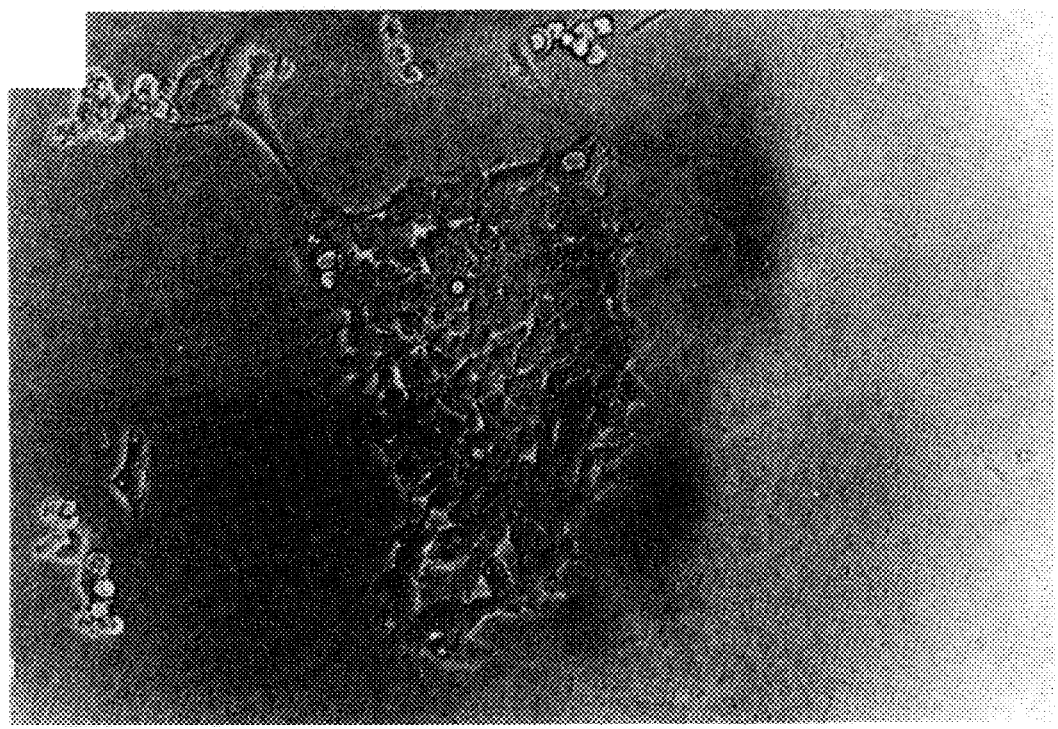
Figure 5D:
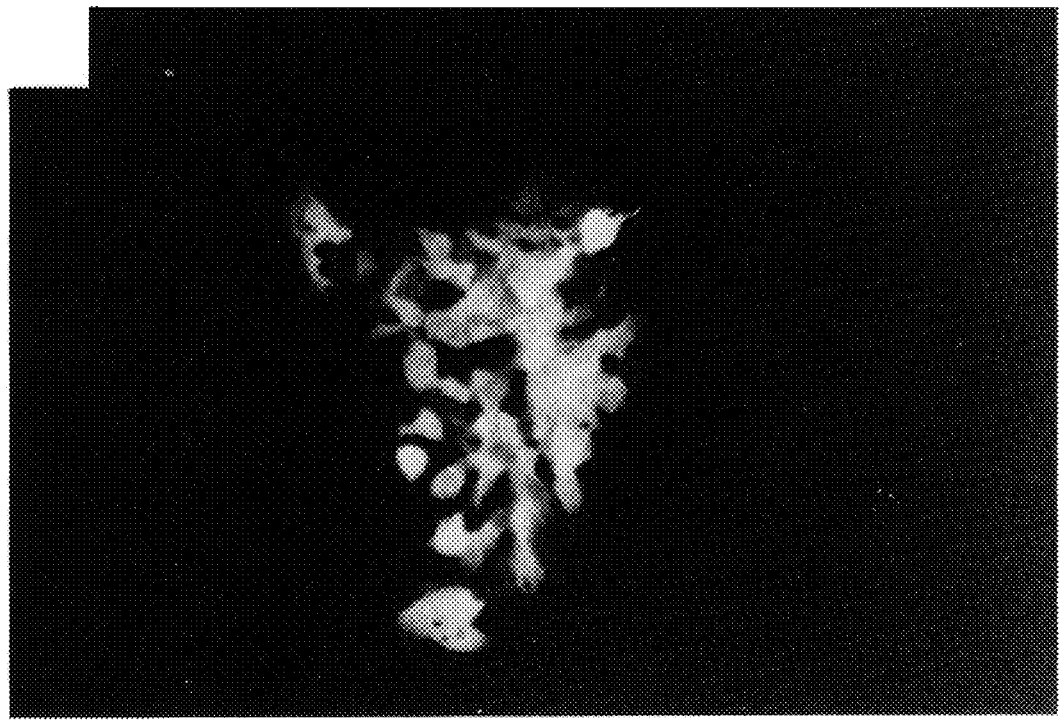
Figure 6B:
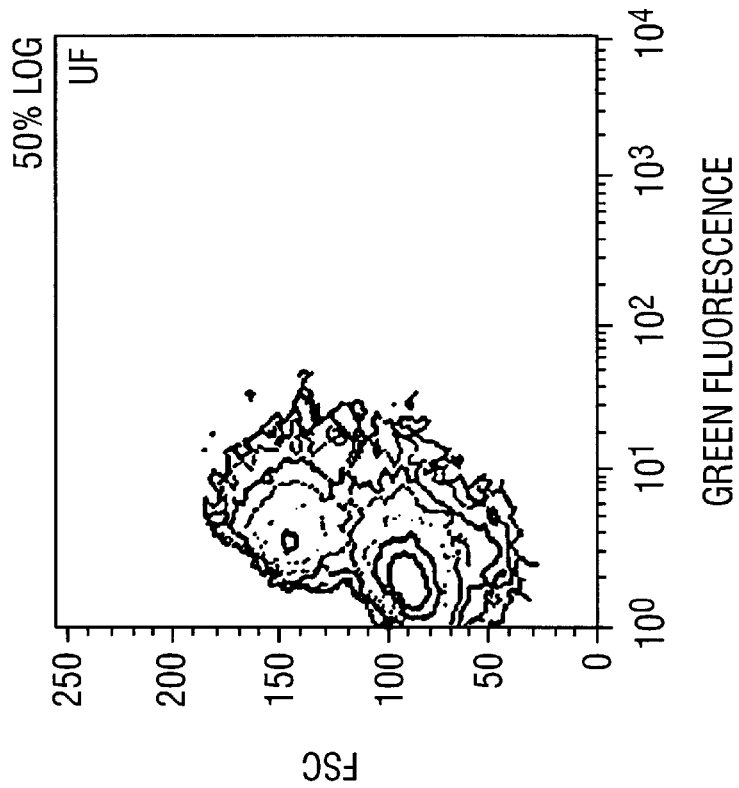
FIG. 6A, FIG. 6B, FIG. 6C and FIG. 6D. FACS analysis of 293 cells, stably transduced with rAAV-$GFP_J$, rAAV-$GFP_H1$, or rAAV-$GFP_H2$ and selected for 2 weeks with G418.
Figure 6A:
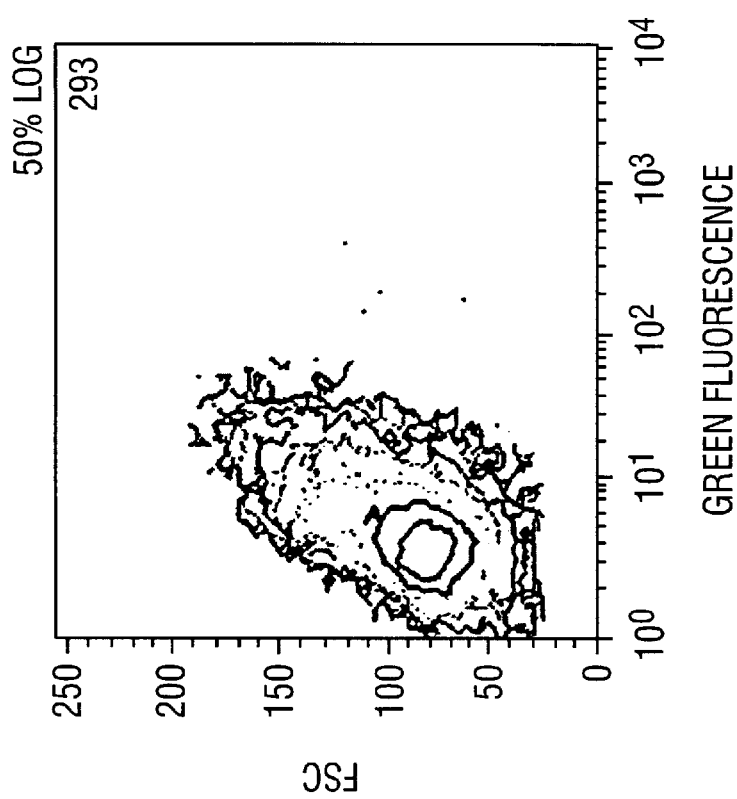
Figure 6D:
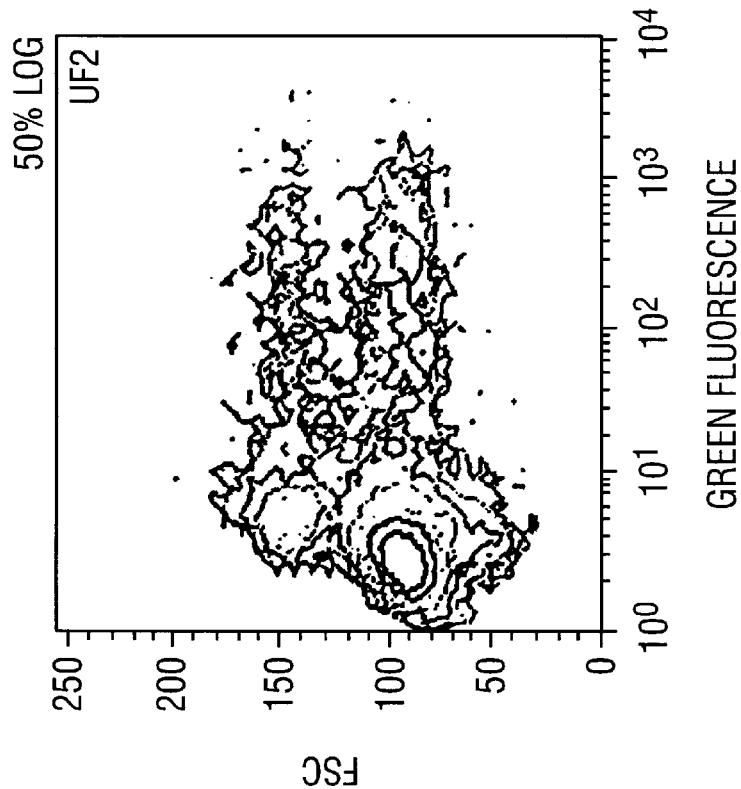
Figure 6C:
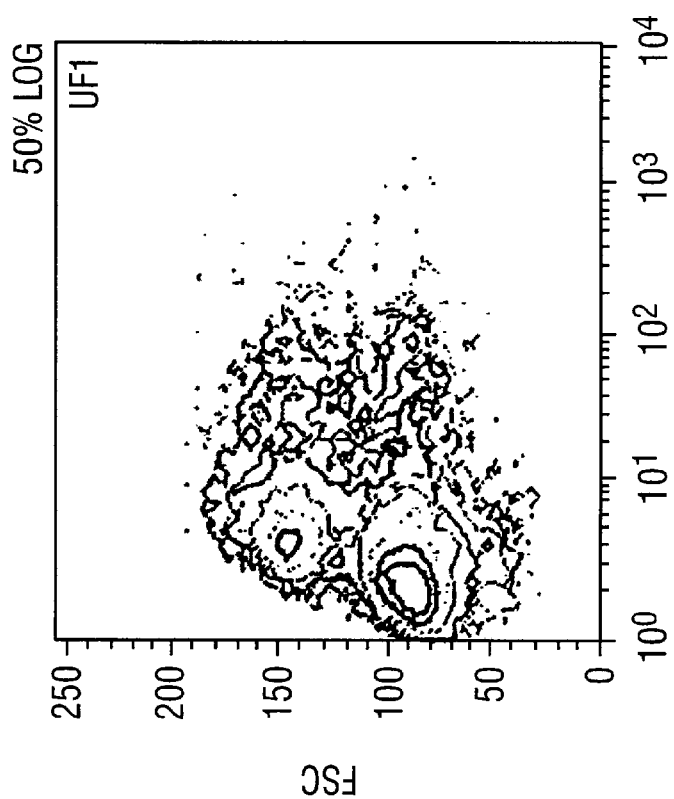

To determine whether the modified gfp cDNA was sufficient now to detect the marker gene at low gene copy number, the inventors isolated recombinant AAV viruses by packaging and using the three gfp constructs (UF, UF1, and UF2) and used them to transduce the gfp marker into 293 cells by virus infection. While there was almost no detectable GFP expression from a virus carrying the gfp10 cDNA (rAAV-GFP$_J$), cells infected with a virus carrying the humanized gfp$_h$ gene (rAAV-GFP$_H$1, or rAAV-GFP$_H$2) were readily detected either visually (FIG. 4A and FIG. 4B), or by FACS analysis. FACS analysis was conducted by harvesting transfected 293 cells and analyzing on a flow cytometer (Becton-Dickinson) equipped for FITC detection at an excitation wavelength of 488 nm. At high M.O.I. (approximately 20) the ratio of infected cells, scored by FACS as fluorescent-positive, reached 70% for rAAV-GFP$_H$2.

To determine more accurately the relative efficiency of the different gfp constructs, 293 cells infected at low multiplicity (MOI of 1) with rAAV-GFP$_J$, rAAV-GFP$_H$1 or rAAV-GFP$_H$2 were first selected for the expression of the second reporter gene, neoR. G418 resistant colonies that have been transduced by an AAV-neoR recombinant virus have been shown by the inventors and others (Cheung et al., 1980; Laughlin et al., 1986; McLaughlin et al., 1988; Samulski et al., 1989) to contain an average of 2–3 copies of the recombinant viral genome integrated into host DNA.

293 cells were stably transduced with rAAV-GFP virus and selected for G418-resistance (200 mg/ml) for two weeks. Resistant colonies were trypsinized, pooled (at least 1000 colonies each for rAAV-GFP$_J$, rAAV-GFP$_H$1 and rAAV-$_{gfph}$2), resuspended in OPTI-MEM media and analyzed by FACS as above.

Uninfected 293 cells have zero green fluorescent cells. After 2 weeks of selection approximately 11% of the UF1 transduced cells and 23% of the UF2 transduced cells that were G418-resistant were also found to express GFP, as judged by fluorescence microscopy. The visual pattern of GFP expression was patchy, with the number of green cells per colony ranging from 1% to about 100% (FIG. 5A, FIG. 5B, FIG. 5C and FIG. 5D). In contrast, only 0.5% of the G418-resistant cells containing the jellyfish GFP-coding rAAV-GFP$_J$ provirus were fluorescent.

Thus, optimization of the codon usage within the gfp gene increased the level of detection at low copy number by approximately 22 fold, and the Ser$_{65}$Thr substitution increased the level of detection by an additional two fold for a total of 45 fold.

Analysis of the G418 resistant cells by FACS, which may be inherently more sensitive to the level of expression, revealed similar differences in the level of detection between GFP$_J$, GFP$_H$1 and GFP$_H$2 (FIG. 6A, FIG. 6B, FIG. 6C and FIG. 6D). In these studies, 0.05% of uninfected 293 cells were scored as exhibiting green fluorescence (i.e., background autofluorescence). No difference in the number of fluorescent cells was detected between GFP$_J$ and the uninfected parental 293 cells.

In contrast to GFP$_J$, approximately 1.6% of the GFP$_H$1 and 10% of the GFP$_H$2 cells were scored positive for green fluorescence. Since no positive cells were detected with GFP$_J$, it was difficult to judge accurately the difference in the frequency of detection between GFP$_J$ and GFP$_H$2. However, conservative estimates of the frequency of detecting a green fluorescent cell in the humanized populations were at least 32-fold (GFP$_H$1) and 190-fold (GFP$_H$2) higher than the background frequency found for GFP$_J$ and uninfected parental 293 cells (FIG. 6A, FIG. 6B, FIG. 6C and FIG. 6D).

Example VII

Expression of Humanized Blue GFP Variant

This example describes expression of a humanized blue GFP mutant, PTR$_{BS}$-UFB, in 293 cells.

To monitor the fluorescence of the blue mutant, 293 cells on a 6 cm plate were cotransfected with PTR$_{BS}$-UF2 and pTR$_{BS}$-UFB plasmids, using Lipofectamine (GIBCO, Life Technologies). The DNA-liposome complex was formed separately for each plasmid and added to the same plate of cells. After 4 days cells were photographed in a fluorescence microscope using a Nikon Filter Cube V-2B.

Figure 7:
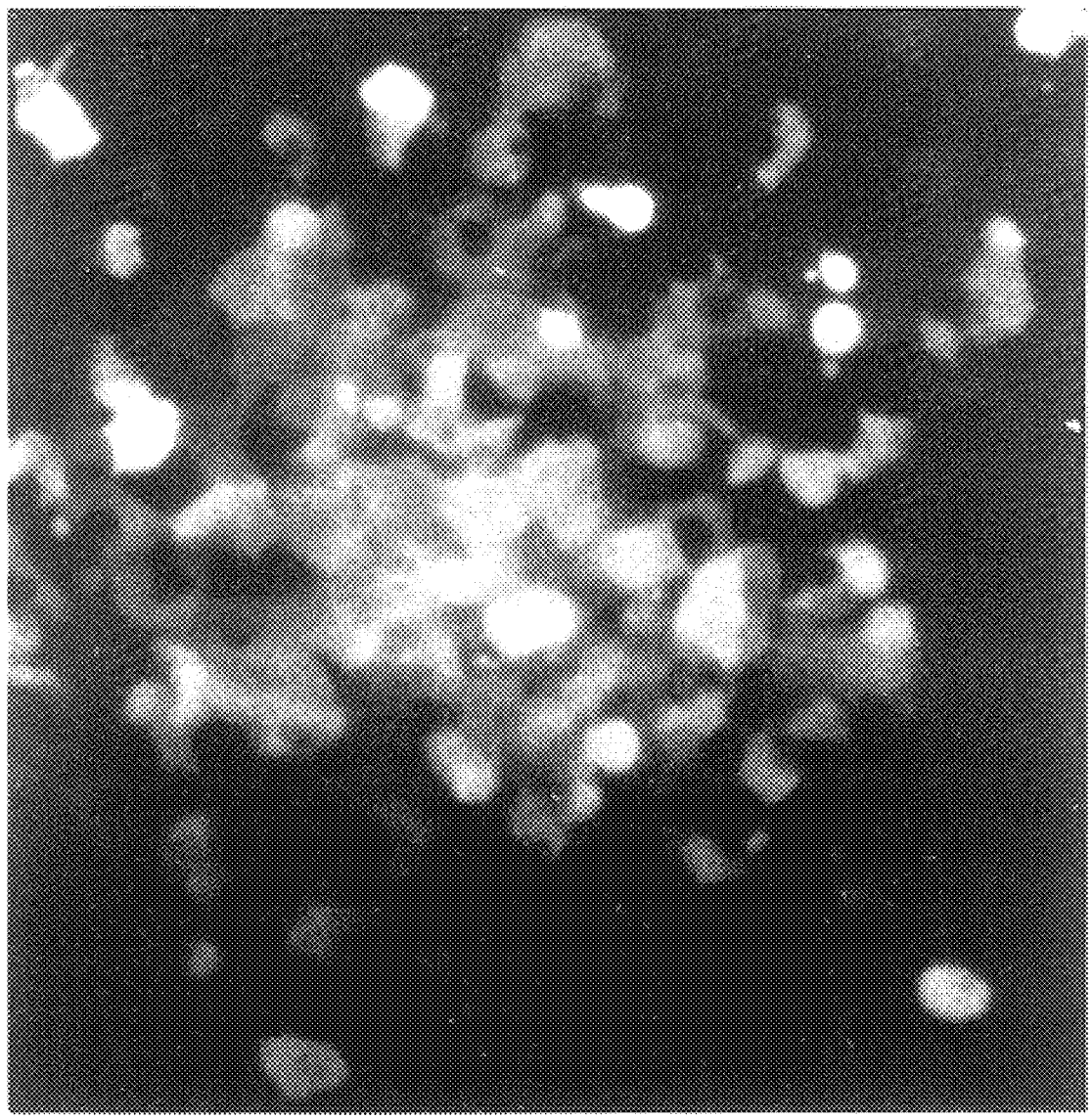
FIG. 7. Fluorescence of the blue His66 mutant of the humanized gfp. 293 cells were co-transfected with $pTR_{BS}$-UF2 and $pTR_{BS}$-UFB and photographed 4 days posttransfection in the fluorescence microscope, using a Nikon Filter Cube V-2B.

As expected, the blue GFP mutant, pTR$_{BS}$-UFB, when reproduced in a humanized background, induced 293 cells to fluoresce in a true blue color. However, the intensity of the fluorescence was considerably reduced compared to GFP$_H$2. For example, FIG. 7 shows 293 cells co-transfected with pTR$_{BS}$-UF2 and pTR$_{BS}$-UFB; and viewed under conditions favoring the blue fluorescence. The inventors also noticed a rather fast (10–15 sec) bleaching of the blue fluorescence, when observing without a neutral density filter, which rarely happened with GFP$_H$2.

It was reasoned that adding a nuclear localization signal within the blue mutant gene to localize the GFP within the much smaller space of the nucleus would enhance the fluorescence intensity, in an analogous manner to the mitochondrial targetting of Rizzuto et al. (1995). To create the GFPB-nuclear localization mutant, the following primers were made:

```
#1: 5'-TGCTCTAGAGCGGCCGCCGCCACCATGGTGCCCAAGAAGAAGAGGAAGGTGATGAGCAAGGGCGAG-3';    (SEQ ID NO:13);

#2: primer #2 as for the GFPB PCR ™, as described earlier.
```

Figure 11:
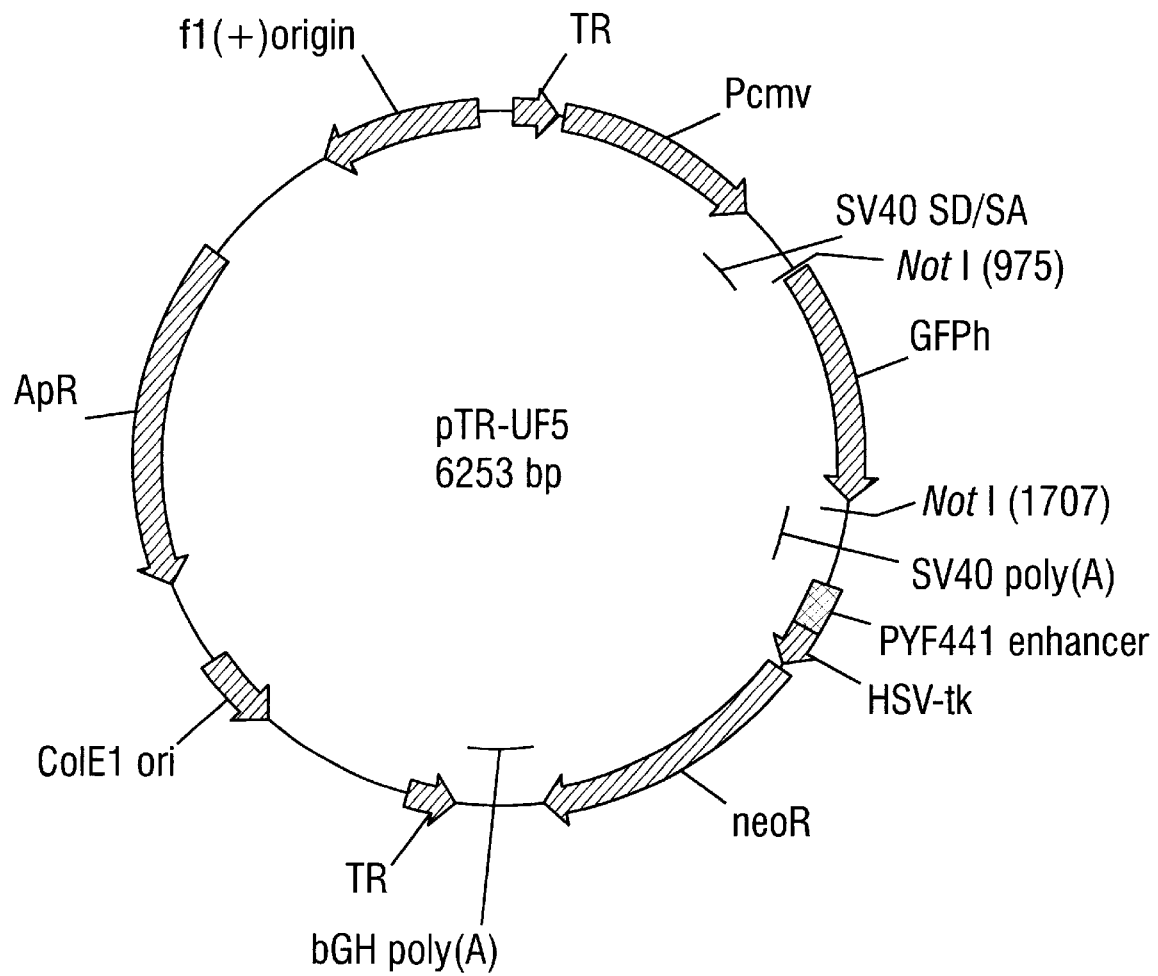
FIG. 11. Construction of pTR-UF5 vector. This is a rAAV vector identical to pTR-UF2 except that the humanized DNA has the point mutation Phe64 to Leu65.
Figure 12:
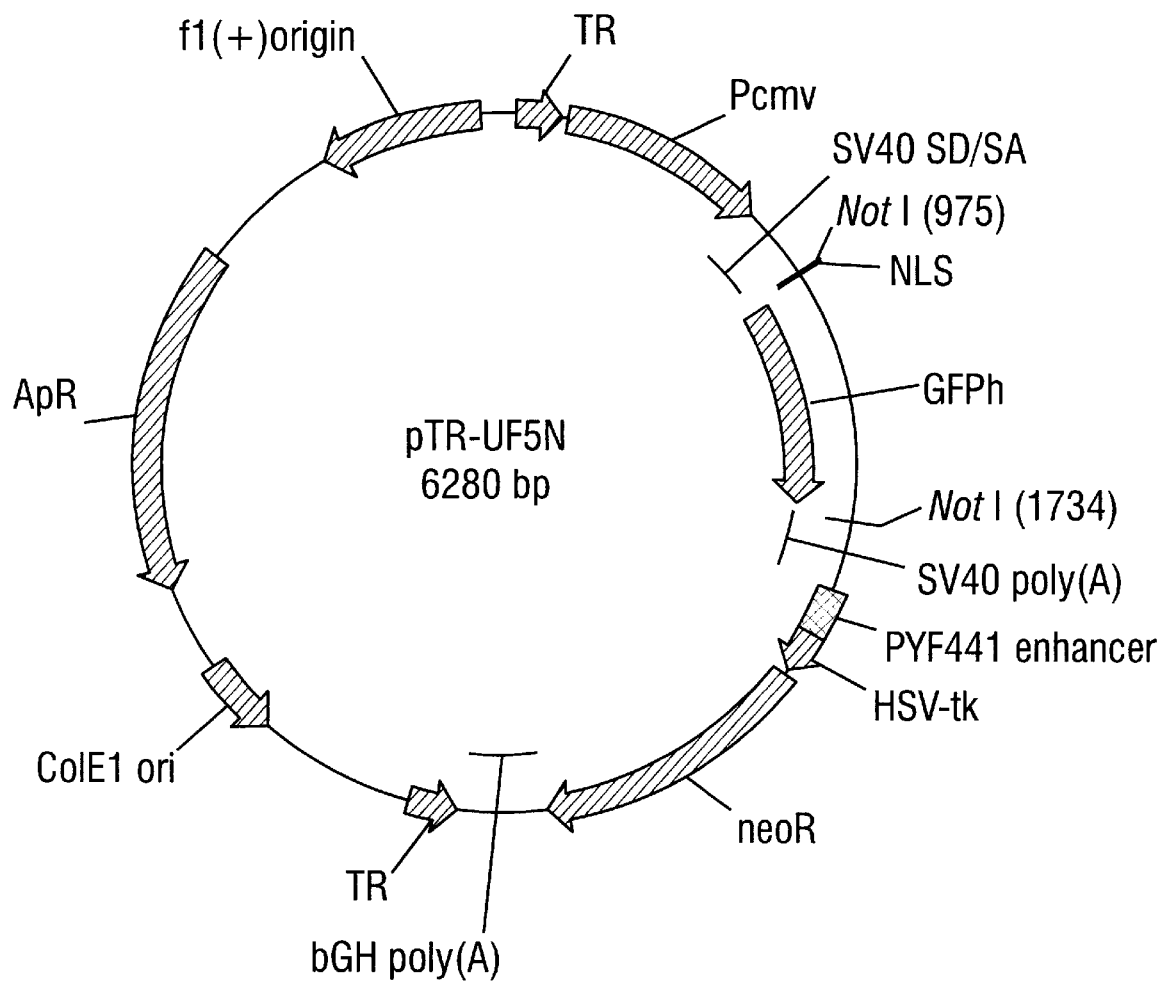
FIG. 12. Construction of pTR-UF5N vector. This rAAV vector is identical to pTR-UF5 exception that it contains a nuclear localization signal.
Figure 13:
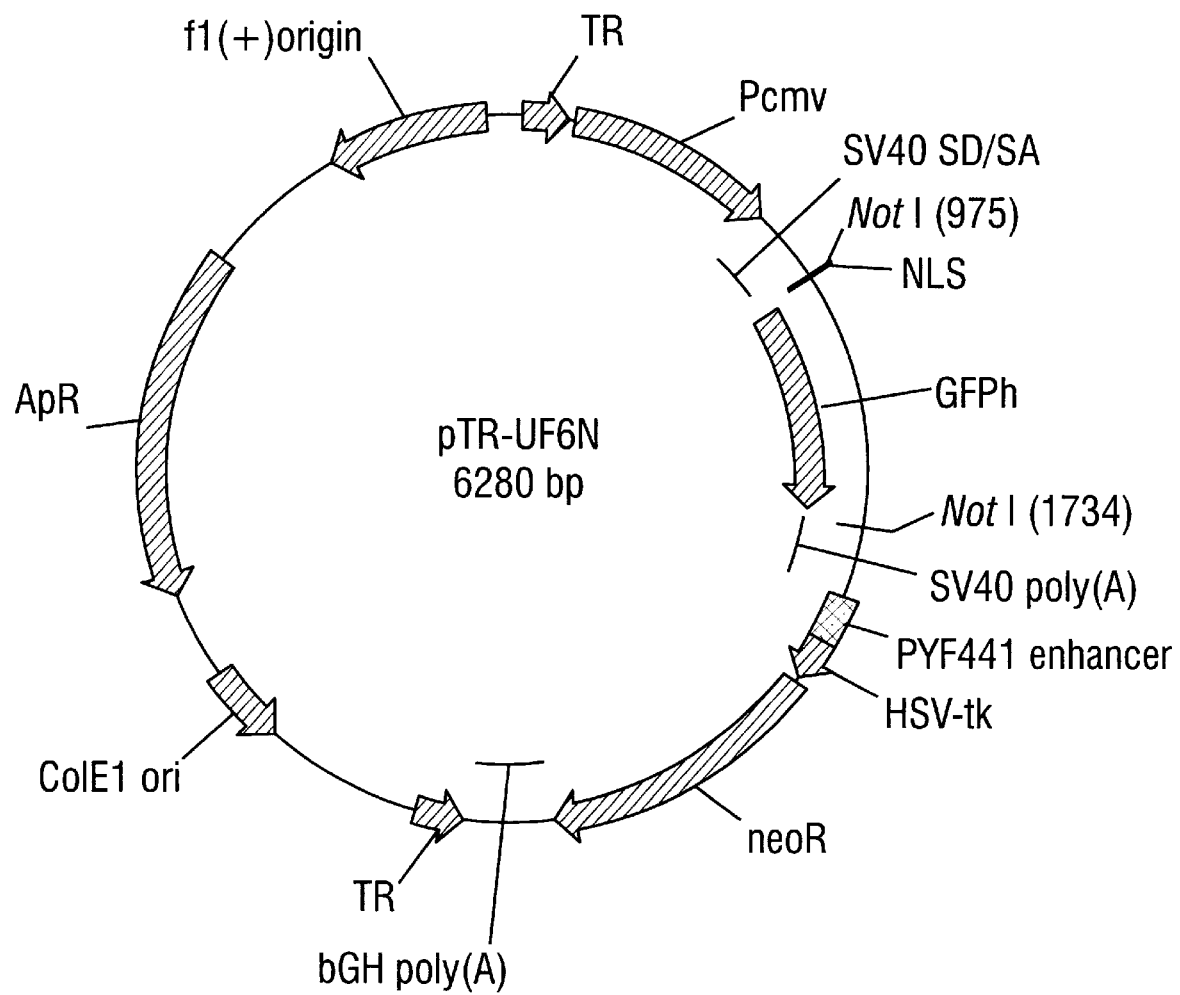
FIG. 13. Construction of pTR-UF 6N vector. This rAAV vector is identical to pTR-UFB except that it contains a nuclear localization signal and a point mutation in the humanized DNA Tyr145 to Phe145.

Recombinant AAV vector plasmid pTR-UF5N was constructed as shown in FIG. 12. This plasmid was prepared as described for pTR-UF2 in Example V except that the humanized GFP gene contains the additional point mutations Phe64 to Leu64 and Ser65 to Thr65 and additionally has the SV40 Large T-antigen nuclear localization signal fused in frame 5' to the GFP gene. Use of the pTR-UF5N vector resulted in increased fluorescence of the GFP compared with pTR-UF5 that did not contain the nuclear localization signal. pTR-UF5 is shown in FIG. 11. pTR-UF5 lacking a nuclear localization signal, has increased GFP fluorescence compared with pTR-UF2.

pTR-UF6 was constructed in a manner similar to that for pTR-UFB except that the humanized GFP DNA contained a point mutation at Tyr145 to Phe145, resulting in enhanced blue fluorescence compared with pTR-UFB. Further adding a nuclear localization signal to pTR-UF6 resulted in pTR-UF6N (FIG. 13); however, this plasmid did not exhibit significantly enhanced blue fluorescence compared with pTR-UF6.

Example VIII
Construction of IRES-GFP Cassette AAV Vector

This example describes the construction of the IRES-GFP cassette AAV vector in which translation of the GFP is controlled by an IRES element from Poliovirus type 1.

Oftentimes, the expression of the transduced gene of interest is hard to follow due to various technical reasons. On these occasions the monitoring of a marker gene delivered by the same vector is of a little help, since it is usually transcribed from a separate promoter. However, coordinate expression of both the reporter gene and the gene under study can be achieved if these genes are placed within one dicistronic transcription unit. The cap-independent translational initiation of the second cistron in this array is mediated by an untranslated RNA sequence which functions as an internal ribosomal entry site (Jackson et al., 1990; Jang et al., 1988; Macejak and Sarnow, 1991).

To incorporate this feature into the inventor's AAV vectors, the inventors constructed the plasmid $pTR_{BS}$-UF3, in which translation of the GFP is controlled by an IRES element from Poliovirus type 1 (Dirks et al., 1993). A restriction site polylinker sequence also was inserted upstream of the IRES element to facilitate the insertion of the gene of interest, and the dicistronic messenger RNA was under the control of the CMV promoter (FIG. 2B-1, FIG. 2B-2, FIG. 2B-3, FIG. 2A-1 and FIG. 2A-2).

The level of IRES-driven GFP expression with the $pTR_{BS}$-UF3 vector, as judged by the fluorescence intensity, was lower than that seen with $pTR_{BS}$-UF2, the parental plasmid, and was comparable to the $pTR_{BS}$-UF1 vector. However, when another open reading frame (human B-chain insulin cDNA) was inserted upstream from the IRES element, the expression of GFP increased and was indistinguishable from the parent vector $pTR_{BS}$-UF2.

Example IX
Construction and Use of Recombinant GFP Adenovirus

The present example describes the construction of a recombinant adenovirus shuttle plasmid and the construction of recombinant adenovirus expressing humanized gfp gene. This exemplifies the use of different vector systems in humanized GFP expression.

To construct the adenovirus shuttle vector pΔE1GFP (FIG. 2B-1, FIG. 2B-2 and FIG. 2B-3) the parent plasmid pTR-UF3 was partially digested with SalI and then digested to completion with BglII. The transcription cassette consisting of the CMV promoter, intron, IRES element, $GFP_H$ cDNA and poly(A) site was isolated from an agarose gel. This fragment was subcloned into pΔE1sp1A (Bett et al., 1994) which had been digested with BamHI and SalI.

To generate recombinant adenovirus the shuttle vector pΔE1GFP (Bett et al., 1994) and the Ad vector pJM17 (McGrory et al., 1988) were cotransfected into 293 cells, using the procedure recommended by the supplier (Microbix Biosystems Inc). Plaques containing recombinant Ad were screened by visual selection under epifluorescence for a group of bright green cells displaying typical cytopathic effect (CPE). The recombinant Ad was designated AdΔE1GFP and propagated using standard techniques.

Figure 8:
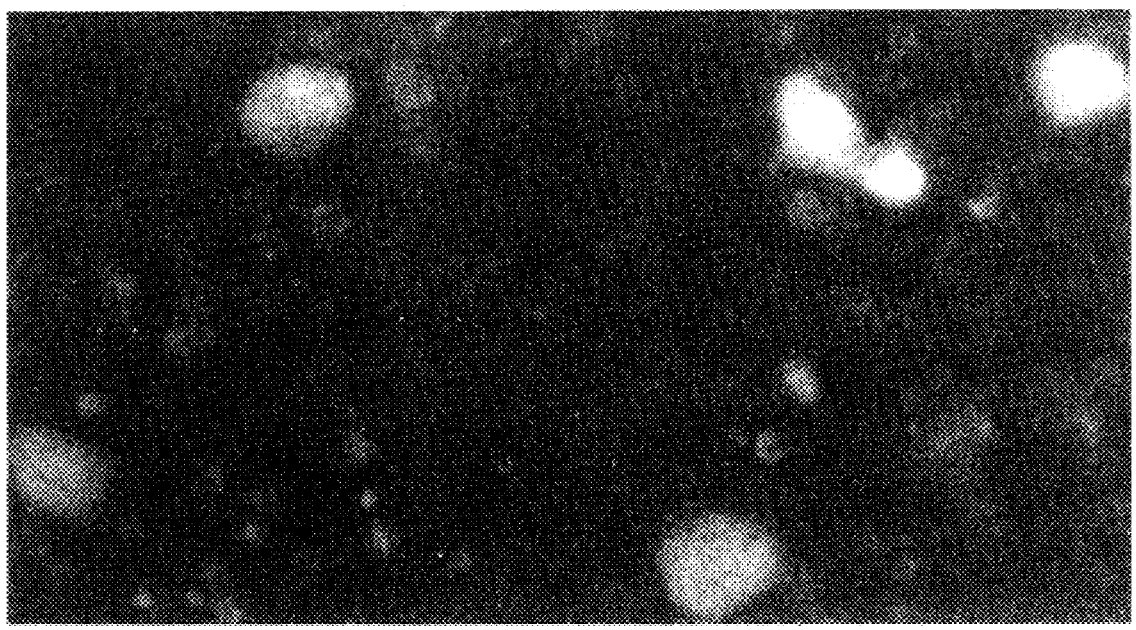
FIG. 8. A single plaque of recombinant AdΔE1GFP as seen in the fluorescent microscope. The plaque was photographed at 40 hrs postinfection.
Figure 9A:
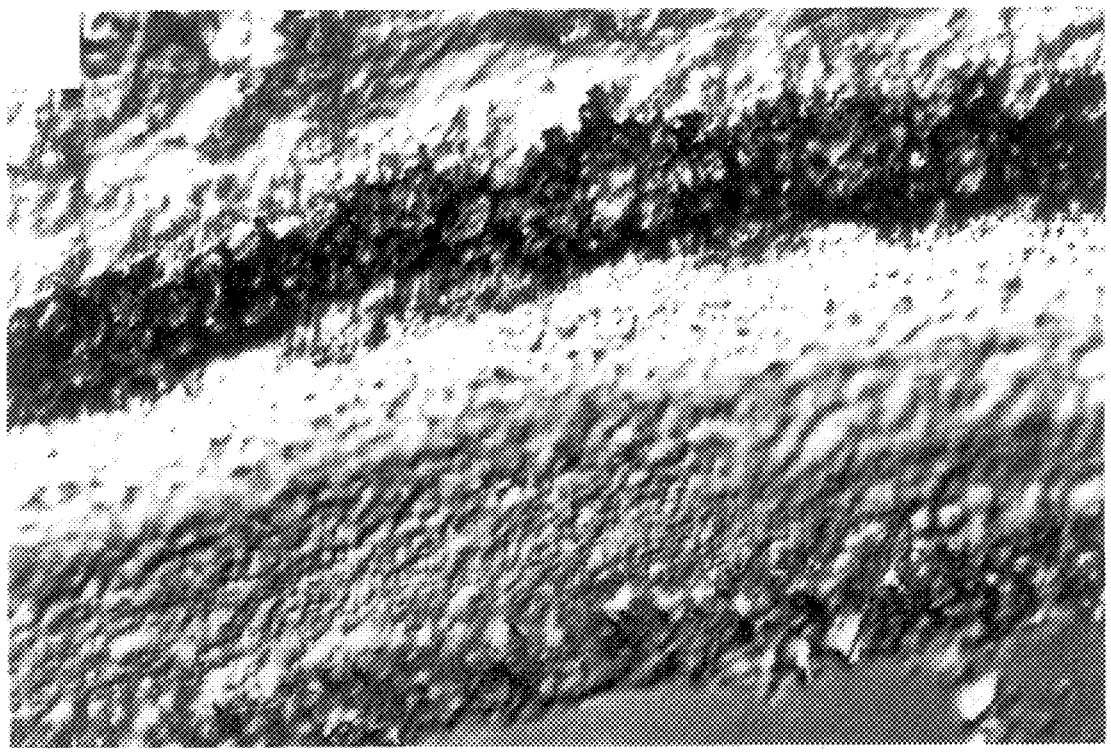
FIG. 9A, FIG. 9B, FIG. 9C and FIG. 9D. GFP fluorescence in a segment of guinea pig RPE infected with rAAV-$GFP_H2$.
Figure 9B:
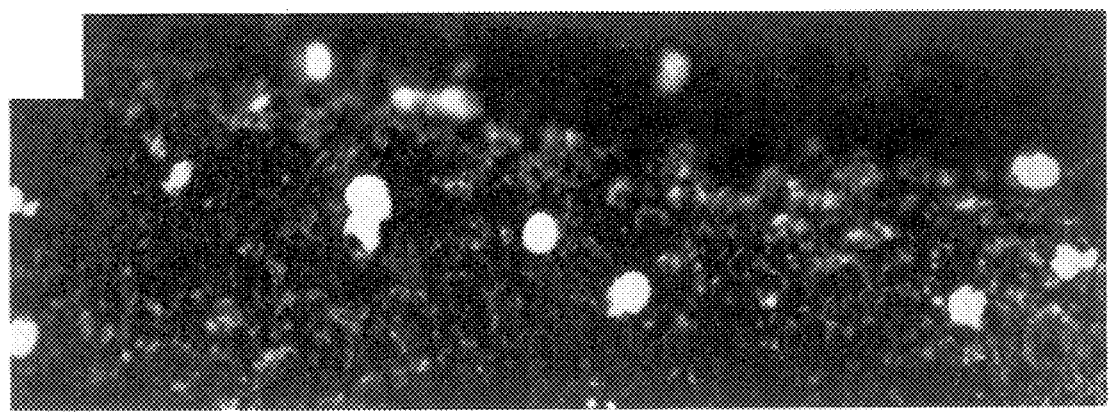
Figure 9C:
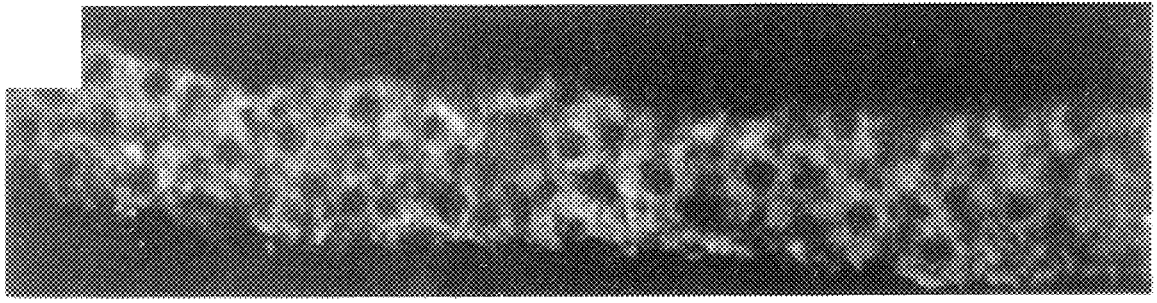
Figure 9D:
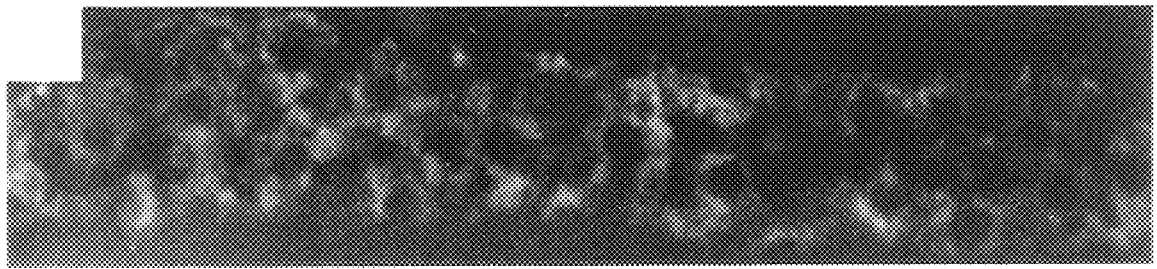

When pΔE1gfp was recombined in vivo with a plasmid containing the remainder of the adenovirus genome, pJM17 (Snyder et al., 1993), a recombinant adenovirus was produced which carried and expressed GFP (FIG. 8). The GFP reporter gene allowed an easy selection of recombinant Ad plaques. When examined by fluorescent microscopy, a true recombinant plaque consisted of a compact group of bright green cells displaying typical adenovirus CPE, whereas a false recombinant plaque contained no green cells. The ratio of true to false plaques was about 1:2, when using the combination of the pΔE1gfp shuttle plasmid and the pJM17 donor plasmid. Thus, use of the GFP selection significantly simplified the screening process.

Example X
Infection of Photoreceptor Cells of Guinea Pig

The present example describes the expression of the humanized, $gfp_h$, cDNA and its use as a reporter gene in differentiated mammalian cells.

rAAV-$GFP_H1$ was used to infect a retina of a guinea pig. Guinea pigs were anesthetized by intramuscular injection of ketamine (35 mg/kg body weight) and xylazine (8 mg/kg) mixture. Each eye was dilated with 2.5% phenylephrine (Neo-Synephrine) and 0.5% tropicamide, and a topical anesthetic (proparacaine HCl) was administered to the cornea. The eye pressure was lowered by paracentesis of the anterior chamber. Then a 30 gauge needle was inserted at the pars plana into the vitreous under visual guidance of an indirect ophthalmoscope and 25 ml of rAAV-$GFP_H2$ ($2.5 \times 10^7$ infectious particles) was delivered. The eyes were examined by ophthalmoscopy for fluorescence and sites of inflammation.

At 28 days postinjection animals were anesthetized and euthanized with an intramuscular injection of ketamine HCl followed by an intraperitoneal pentobarbital sodium overdose. The animals were then perfused using 4% paraformaldehyde in 0.1M PBS. The eyes were dissected out and the lens and cornea were removed. The retina and eye cup were additionally fixed overnight at 4° C. The retina were then infiltrated with 7.5%, 15%, and 30% sucrose and cryosectioned at 20–25 mm thickness. Tissue specimens were visualized using fluorescein excitation/emission filters on a Brorad confocal microscope.

To test the utility of $GFP_H$ cDNA as a reporter gene in an in vivo system, the inventors injected rAAV-$GFP_H2$ virus into the vitreous body of the right eyes of two strain-13 guinea pigs. Tissue sections of the eye revealed weak $GFP_H2$ fluorescence predominantly in cells of the ganglion cell layer (the layer closest to the vitreous injection). In addition, a few horizontal cells exhibited $GFP_H2$ fluorescence. The greatest intensity of $GFP_H2$ was seen in cells of the retinal pigment epithelium (RPE) (FIG. 9A, FIG. 9B, FIG. 9C and FIG. 9D).

With rAAV-$GFP_H2$ every tissue section examined had RPE cells that fluoresced. This preference for CMV promoter driven expression in RPE cells has been previously noted (Bennett et al., 1994; Li et al., 1994). Examination of tissue specimens from the control left eyes revealed no cell specific emission except for autofluorescence within pigment granules of the RPE. The fact that inoculation of AAV into the guinea pig vitreous cavity lead to GFP expression in RPE cells demonstrated that AAV can traverse the neural retina, 100–200 mM thick. This property may be related to the small diameter of AAV particles.

Example XI
pGREENLANTERN™ VECTOR

This example describes the generation of a particularly useful vector, termed pGREENLANTERN™.

To create pCMVSPORT 2.1, the following protocol was used. pSPORT2 (available from Life Technologies Inc., Gaithersburg, Md.) was digested with PvuII and BssHI. The ends were made blunt by the action of Klenow fragment. The large fragment was gel purified.

pSVSPORT (available from Life Technologies Inc., Gaithersburg, Md.) was than digested with EarI and HaeII. The ends were made blunt by the action of T4DNA polymerase. The smaller fragment was gel purified. The two fragments were ligated and the resulting plasmid was called pRAD-TEMP.

pRAD-TEMP was partialed with BamHI and treated with Klenow. The DNA was self ligated and the resulting plasmid had only one BamHI site in the multiple cloning site (MCS). The MCS was changed by cutting the DNA with XbaI and MluI and ligating a new oligo that had the following restriction sites (XbaI-BamHI-XhoI-ApaI-HindII and MluI). This plasmid was called pSVSPORT-B1.

pSVPSORT-B1 was digested with ClaI and StuI, treated with Klenow fragment. The CMV promoter was from pCMVβgal. The promoter was on a SfcI-XbaI fragment that was made blunt with Klenow fragment. The DNAs were ligated and the resulting plasmid was called pCMVSPORT 2.1.

To create pGREENLANTERN, pCMVSPORT 2.1 was utilized. pCMVSPORT 2.1 was digested with NotI and treated with Calf intestinal alkaline phosphatase. The DNA was ligated to the NotI fragment of the humanized UF2. The orientation was confirmed. The vector was called pCMVSPORT-UF2.

Figure 10:
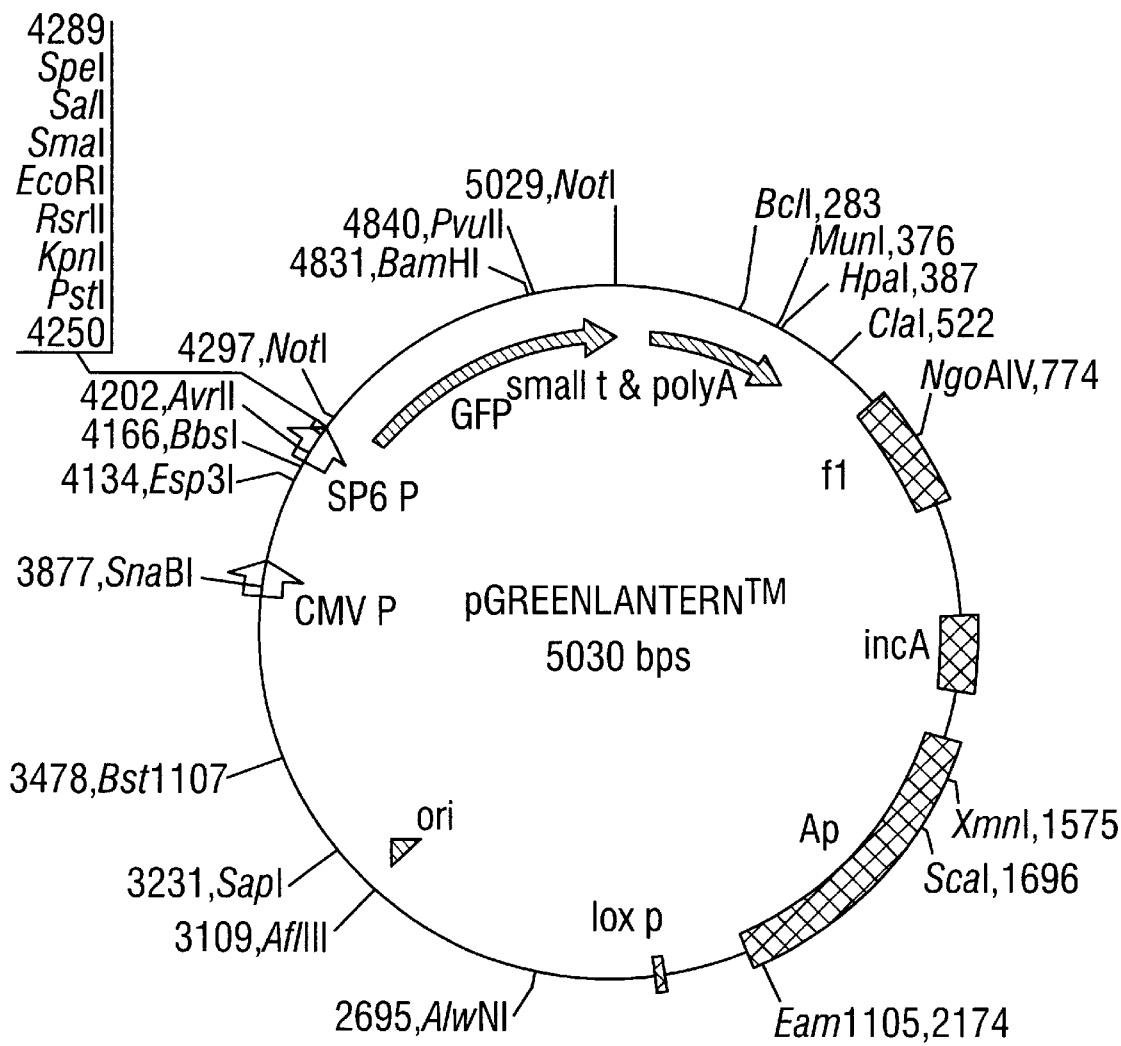
FIG. 10. pGREENLANTERN™ plasmid. GFP represents the humanized GFP of the present invention. Other functional elements and restriction sites are shown.

The T7 DNA polymerase region was deleted by digestion with XbaI-NheI and self ligation of the larger vector fragment. This DNA is the pGREENLANTERN-1 vector (FIG. 10). The complete sequence of pGREENLANTERN-1 is given in SEQ ID NO:14.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adams et al., "Vectors for using green fluorescent protein (gfp) as a reporter of gene expression and protein localization in mammalian cells", *FASEB J.*, 9(6):A1336, Abstract #465, 1995.

Adams et al:, *In: Fluorescent Probes for Biological Activity of Living Cells: A Practical Guide*, ed. Mason, Academic, New York, pp. 133–149, 1993.

Adams et al., *Nature* (London), 349:694–697, 1991.

Adelman et al., *DNA*, 2:183, 1983.

Baichwal et al., "Vectors for gene transfer derived from animal DNA viruses: Transient and stable expression of transferred genes," In: *Gene transfer*, Kucherlapati R, ed., New York: Plenum Press, pp. 117–148, 1986.

Bennett, Wilson, Sun, Forbes, Maguire, "Adenovirus Vector-Mediated in vivo Gene Transfer Into Adult Murine Retina," *Invest. Ophthalmol. Vis. Sci.*, 35:2535–2542, 1994.

Bennetzen and Hall, "Codon Selection in Yeast," *The Journal of Biological Chemistry*, 257(6):3026–3031, March, 1982.

Bett, Haddara, Prevac, Graham, "An Efficient and Flexible System for Construction of Adenovirus Vectors with Insertions or Deletions in Early Regions 1 and 3," *Proc. Natl. Acad. Sci. USA*, 91:8802–8806, 1994.

Bittner et al., *Methods in Enzymol.*, 153:516–544, 1987.

Chalfie, Tu, Euskirchen, Ward, Prasher, "Green Fluorescent Protein as a Marker For Gene Expression," *Science*, 263:802–805, 1994.

Chang et al., "Foreign gene delivery and expreddion in hepatocytes using a hrpatitis B virus vector," *Hepatology*, 14:134A, 1991.

Cheung, Hoggan, Hauswirth, Berns, In: *Integration of the Adeno-Associated Virus Genome Into Cellular DNA in Latently Infected Human Detroit 6 Cells, J. Virol.*, 33:739–748, 1980.

Clark, Voulgaropoulou, Fraley, Johnson, "Cell lines for the production of recombinant adeno-associated virus," *Human Gene Therapy*, 6:1329–1341, 1995.

Cody, Prasher, Westler, Prendergast, Ward, "Chemical Structure of the Hexapeptide Chromophore of The Aequorea Green-Fluorescent Protein," *Biochemistry*, 32:1212–1218, 1993.

Cohen, "Naked DNA Points Way to Vaccines," *Science*, 259:1691–1692, 1993.

Colberre-Garapin et al., *J. Mol. Biol.*, 150:1, 1981.

Coupar et al., "A general method for the construction of recombinant vaccinia virus expressing multiple foreign genes," *Gene*, 68:1–10, 1988.

Cox et al, *J. Virol.* 67(9):5664–5667, 1993.

Crea et al., *Proc. Natl. Acad. Sci. USA*, 75:5765, 1978.

Culver, Ram, Wallbridge, Ishii, Oldfield, Blaese, "In vivo gene transfer with retroviral vector-producer cells for treatment of experimental brain tumors," *Science*, 256:1550–1552, 1992.

*Current Protocols in Molecular Biology*, John Wiley & Sons, Chapter 8, 1995.

Cutler and Ward, 1993.

Delagrave and Youvan, "Searching sequence space to engineer proteins: Exponential ensemble mutagenesis," *Bio/Technology*, 11:1548–1552, 1993.

Delagrave et al., "Recursive ensemble mutagenesis," *Protein Engineering*, 6:327–331, 1993.

Delagrave et al, "Red-Shifted Excitation Mutants of the Green Fluorescent Protein," *Bio/Technology*, 13:151–154, February, 1995.

Dirks, Wirth, Hauser, "Dicistronic Transcription Units for Gene Expression in Mammalian Cells," *Gene*, 128:247–249, 1993.

Dopf and Horiagon, *Fluorescent Proteins and Applications Meeting*, Palo Alto, Calif. (Abstract), 1995.

Ehrig et al., *FEBS Lett.*, 367:163–166, 1995.

Eichenlaub, *J. Bacteriol*, 138:559–566, 1979.

Flotte, Solow, Owens, Afione, Zeitlin, Carter, "Gene expression from adeno associated virus vector in airway epithelial cells," *Am. J. Respir. Cell Mol. Biol.*, 7:349–356, 1992.

Flotte, Afione, Conrad, McGrath, Solow, Oka, Zeitlin, Guggino, Carter, "Stable in vivo expression of the cystic fibrosis transmembrane conductance regulator with an adeno-associated virus vector," *Proc. Natl. Acad. Sci. USA*, 90:10613–10617, 1993.

Flotte, Afione, Zeitlin, "Adeno-associated virus vector gene expression occurs in nondividing cells in the absence of vector DNA integration," *Am.J. Respir. Cell Mol. Biol.*, 11:517–521, 1994.

Flotte, Barraza-Ortiz, Solow, Afione, Carter, Guggino, "An improved system for packaging recombinant adeno-associated virus vectors capable of in vivo transduction," *Gene Therapy*, 2:29–37, 1995.

Freedman et al., *Journal of Biological Chemistry*, 268:2254, 1993.

Fynan et al., "DNA vaccines: Protective immunizations by parenteral, mucosal, and gene-gun inoculations," *Proc. Natl. Acad. Sci. USA*, 90:11478–11482, 1993.

Gal et. al., *Lab. Invest.*, 68(1):18, 1993.

Ghosh-Choudhury and Graham, *Biochem. Biophys. Res. Comm.*, 147:964–973, 1987.

Gluzman et al., In: *Eukaryotic Viral Vectors* (Gluzman, Y., ed) pp. 187–192, Cold Spring Harbor Press, Cold Spring Harbor, N.Y., 1982.

Goldman and Youvan, "An algorithmically optimized combinatorial library screened by digital imaging spectroscopy," *Bio/Technology*, 10:1557–1561, 1992.

Gopal, "Gene transfer method for transient gene expression, stable transfection, and cotransfection of suspension cell cultures," *Mol. Cell Biol.*, 5:1188–1190, 1985.

Graham and van der Eb, "A new technique for the assay of infectivity of human adenovirus 5 DNA", *Virology*, 52:456–467, 1973.

Grantham, et al., "Codon Catalog Usage and the Genome Hypothesis," *Nucleic Acids Research*, 8(1):r49–r62, 1980.

Grantham, Gautier, Gouy, Jacobzone, Mercier, "Codon Catalog Usage is a Genome Strategy Modulated for Gene Expressivity," *Nucleic Acids Research*, 9(1):r43–r74, 1981.

Heim, Cubitt, Tsien, "Improved green fluorescence," *Nature*, 373:663–664, February, 1995.

Heim, Cubitt, Tsien, "Wavelength Mutations and Posttranslational Autoxidation of Green Fluorescent Protein," *Proc. Natl. Acad. Sci. USA*, 91:12501–12504, 1994.

Hermonat and Muzyczka, "Use of adeno-associated virus as a mammalian DNA cloning vector; transduction of neomycin. resistance into mammalian tissue culture cells," *Proc. Natl. Acad. Sci. USA*, 81:6466–6470, 1984.

Horwich et al. "Synthesis of hepadenovirus particles that contain replication-defective duck hepatitis B virus genomes in cultured HuH7 cells," *J. Virol*, 64:642–650, 1990.

Ikemura, "Correlation Between the Abundance of *Escherichia coli* Transfer RNAs and the Occurrence of the Respective Codons in its Protein Genes," *J. Mol. Biol.*, 146:1–21, 1981.

Ikemura, "Correlation Between the Abundance of *Escherichia coli* Transfer RNAs and the Occurrence of the Respective Codons in its Protein Genes: A Proposal for a Synonymous Codon Choice that is Optimal for the *E. coli* Translational System," *J. Mol. Biol.*, 151:389–409, 1981.

Ikemura, "Correlation Between the Abundance of Yeast Transfer RNAs and the Occurrence of the Respective Codons in Protein Genes. Differences in Synonymous Codon Choice Patterns of Yeast and *Escherichia coli* with reference to the Abundance of Isoaccepting Transfer RNAs," *J. Mol. Biol.*, 158:573–597, 1982.

Ikemura, "The Frequency of Codon Usage in *E. coli* Genes: Correlation With Abundance of Cognate tRNA," p. 519–534, In: *Genetics And Evolution of RNA Polymerase, tRNA, And Ribosomes*, S. Osawa et al. (ed.), University of Tokyo Press, Tokyo and Elsevier/North Holland, Amsterdam, 1980.

Inouye and Tsuji, *FEBS Lett.*, 341:277–280, 1994.

Jackson, Howell, Kaminski, "The Novel Mechanism of Initiation of Picornavirus RNA Translation," *Trends. Biochem. Sci.*, 15:477–483, 1990.

Jang, Krausslich, Nicklin, Duke, Palmenberg, Wimner, "A Segment of The 5' Nontranslated Region of Encephalomyocarditis Virus RNA Directs Internal Entry of Ribosomes During in vitro Translation," *J. Virol.* 62:2636–2643, 1988.

Jiao et al., "Particle Bombardment-Mediated Gene Transfer and Expression in Rat Brain Tissues", *BIO/TECHNOLOGY*, 11:497–502, 1993.

Kaplitt, Leone, Samulski, Siao, Pfaff, O'Malley, During, "Long-term gene expression and phenotypic correction suing adeno-associated virus vectors in the mammalian brain," *Nature Genetics*, 8:148–154, 1994.

Karlsson et al., *EMBO J.*, 5:2377–2385, 1986.

Kasahara et al, *Science*, 266:1373–1376, 1994.

Kotin, Siniscalco, Samulski, Zhu, Hunter, McLaughlin, Muzyczka, Berns, "Site-specific integration by adeno-associated virus," *Proc. Natl. Acad.Sci. USA*, 87:2211–2215, 1990.

Kozak, "At Least Six Nucleotides Preceding the AUG Initiator Codon Enhance Translation in Mammalian Cells," *J. Mol. Biol.*, 196:947–950, 1987.

Kozak, "Downstream Secondary Structure Facilitates Recognition of Initiator Codons by Eukaryotic Ribosomes," *Proc. Natl. Acad. Sci. USA*, 87:8301–8305, 1990.

LaFace, Hermonat, Wakeland, Peck, "Gene transfer into hematopoietic progenitor cells mediated by an adeno-associated virus vector, *Viology*, 162:483–486, 1988.

Laughlin, Cardellichio, Coon, "Latent Infection of KB Cells with Adeno-Associated Virus Type 2," *J. Virol.*, 60:515–524, 1986.

Lebkowski, McNally, Okarma, Lerch, "Adeno-associated virus: a vector system for efficient introduction and integration of DNA into a variety of manmralian cell types," *Mol. Cell. Biol.*, *:3988–3996, 1988.

Ledley, *J. Pediatrics*, 110:1. 1987.

Li, Adamian, Roof, Berson, Dryja, Roessler, Davidson, "In vivo Transfer of a Reporter Gene to the Retina Mediated by an Adenoviral Vector," *Invest. Ophthalmol. Vis. Sci.*, 35:2543–2549, 1994.

Lim et al., *J. Biochem.* (Tokyo), 118:13–17, 1995.

Lowy et al., *Cell*, 22:817, 1980.

Luo, Zhou, Cooper, Munshi, Boswell, Broxmeyer, Srivastava, "Adeno-associated virus 2 mediated transfer and functional expression of a gene encoding the human granulocyte-macrophage colony-stimulating factor," *Blood*, 82: suppl. 1,303A, 1994.

Macejak and Sarnow, "Internal Initiation of Translation Mediated by the 5' Leader of a Cellular mRNA [see comments]," *Nature*, 353:90–94, 1991.

McCarty, Christensen, Muzyczka, "Sequences Required for Coordinate Induction of Adeno-Associated Virus p19 and p40 Promoters by Rep Protein," *J. Virol.*, 65:2936–2945, 1991.

McGrory, Bautista, Graham, "A Simple Technique for the Rescue of Early Region I Mutations Into Infectious Human Adenovirus Type 5," *Virology*, 163:614–617, 1988.

McLaughlin, Collis, Hermonat, Muzyczka, "Adeno-Associated Virus General Transduction Vectors: Analysis of Proviral Structures," *J. Virol.*, 62:1963–1973, 1988.

Messing et al., Third Cleveland Symposium on Macromolecules and Recombinant DNA, Editor A. Walton, Elsevier, Amsterdam, 1981.

Miller, *Curr. Top. Microbiol. Immunol.*, 158:1, 1992.

Morin and Hastings, "Energy Transfer in a Bioluminescent System," *J. Cell Physiol*, 77:313–318, 1971.

Morise et al., *Biochemistry*, 13:2656–2662, 1974.

Muhlrad et al., *Yeast*, 8:79–82, 1992.

Mulligan et al., *Proc. Natl. Acad. Sci. USA*, 78:2072, 1981.

Muzyczka, "Use of Adeno-Associated Virus as a General Transduction Vector for Mammalian Cells," *Curr. Top. Microbiol. Immunol.*, 158:97–129, 1992.

Muzyczka, "Use of AAV as a general transduction vector for mammalian cells," In: *Curr. Top. Micro. Imm. Viral Expression Vectors*, (N. Muzyczka, ed), Springer Verlag, Berlin, 158:97–129, 1991.

Nicolau, et al, *Proc. Natl. Acad. Sci. U.S.A.*, 80:1068, 1983.

Nicolau and Sene, "Liposome-mediated DNA transfer in eukaryotic cells," *Biochem. Biophys. Acta*, 721:185–190, 1982.

O'Hare et al., *Proc. Natl. Acad. Sci. USA*, 78:1527, 1981.

Ohi, Dixit, Tillery, Plonk, "Construction and replication of an adeno-associated virus expression vector that contains human λ-globin cDNA," *Gene*, 89L,:279–282, 1990.

Pelletier and Sonenberg, "Internal initiation of translation of eukaryotic mRNA directed by a sequence derived from poliovirus RNA," *Nature*, 334:320–325, 1988.

Perozzo et al., *J. Biol. Chem.*, 263:7713–7716, 1988.

Pines, "GFP in *Dictyostelium*," TIG, 11(8):326–327, August, 1995.

Potter et al, "Enhancer-dependent expression of human k immunoglobulin genes introduced into mouse pre-B lymphocytes by electroporation," *Proc. Natl Acad. Sci. USA*, 81:7161–7165, 1984.

Prasher, Eckenrode, Ward, Prendergast, Cormier, "Primary Structure of the Aequorea Victoria Green-Fluorescent Protein," *Gene*, 111:229–233, 1992.

Ridgeway, "Manmualian expression vectors," *In: Vectors: A survey of molecular cloning vectors and their uses*, Rodriguez R L, Denhardt D T, ed., Stoneham: Butterworth, pp. 467–492, 1988.

Rippe et al., "DNA-mediated gene transfer into adult rat hepatocytes in primary culture," *Mol. Cell Biol.*, 10:689–695, 1990.

Rizzuto et al., "Chimeric green fluorescent protein as a tool for visualizing subcellular organelles in living cells," *Current Biology*, 5(6):635–642, 1995.

Rosenfeld, Siegfried, Yoshimura, Yoneyama, Fukayama, Stier, Pääkkö, Gilardi, Stratford-Perricaudet, Perricaudet, Jallat, Pavirani, Lecocq, Crystal, *Science*, 2.52:431–434, 1991.

Rosenfeld, Yoshimura, Trapnell, Yoneyama, Rosenthal, Dalemans, Fukayama, Bargon, Stier, Stratford-Perricaudet, Perricaudet, Guggino, Pavirani, Lecocq, Crystal, *Cell*, 68:143–155, 1992.

Ryan et al., "Sequence Requirements For Binding of Rep68 to the Adeno-Associated Virus Terminal Repeats," *J. Virol.*, 1995.

Sambrook et al., Molecular cloning: A laboratory manual, Cold Spring Harbor Laboratory, Cold Spring Harbor, N.Y., 1989.

Samulski, Chang, Shenk, "Helper-Free Stocks of Recombinant Adeno-Associated Viruses: Normal Integration Does Not Require Viral Gene Expression," *J. Virol.*, 63:3822–3828, 1989.

Samulski, Berns, Tan, Muzyczka, "Cloning of AAV into pBR322: Rescue of intact virus from the recombinant plasmid in human cells," *Proc.Natl.Acad.Sci. USA*, 79-2077–2081, 1982.

Samulski, Chang, Shenk, "Helper-free stocks of recombinant adeno-associated viruses: Normal integration does not require viral gene expression," J. Virol., 63:3822–3828, 1989.

Samulski, Zhu, Xiao, Brook, Housman, Epstein, Hunter, "Targeted integration of adeno-associated virus (AAV) into human chromosome 19," *EMBO J.*, 10:3 941–3950, 1991.

Santerre et al., *Gene*, 30:147, 1984.

Shelling and Smith, "Targeted integration of transfected and infected adeno-associated virus vectors containing the neomycin resistance gene," *Gene Therapy*, 1:165–169, 1994.

Shimomura, "Structure of the Chromophore of the Aequorea Green Fluorescent Protein," *FEBS. Lett.*, 104:220–222, 1979.

Sikorski and Boeke, *Methods Enzymol.*, 194:302–318, 1991.

Snyder, Im, Ni, Xiao, Samulski, Muzyczka, "Features of The Adeno-Associated Virus Origin Involved in Substrate Recognition by the Viral Rep Protein," *J. Virol.*, 67:6096–6104, 1993.

Stewart et al., *Hum. Gene Ther.*, 3:267, 1992.

Stratford-Perricaudet, Levrero, Chasse, Perricaudet, Briand, *Hum. Gene Ther.*, 1:241–256, 1990.

Stratford-Perricaudet, Makeh, Perricaudet, Briand, *J. Clin. Invest.*, 90:626–630, 1992.

Stringham et al., *Molecular Biology of the Cell*,3:221, 1992.

Suipin and Ward, *Photochem. Photobiol.*, 45:62S, 1989.

Szybalska et al., *Proc. Natl. Acad. Sci. USA*,48:2026, 1962.

Tang et al., *Nature*, 356:152–154, 1992.

Thomsen et al., *Proc. Natl. Acad. Sci. USA*, 81:659–663, 1984.

Torchilin et al., *Faseb J.*, 6:2716, 1992.

Tratschin, West, Sandbank, Carter, "A human parvovirus, adeno-associated virus, as a eucaryotic vector: transient expression and encapsidation of the procaryotic gene for chlorarnphenicol acetyltransferase," *Mol.Cell.Biol.*, 4:2072–2081, 1984.

Tratschin, Miller, Smith, Carter, "Adeno-associated virus vector for high-frequency integration, expression and rescue of genes in mammalian cells," *Mol.Cell.Biol.*, 5:32581–3260, 1985.

Tur-Kaspa et al., "Use of electroporation to introduce biologically active foreign genes into primary rat hepatocytes," *Mol. Cell Biol.*, 6:716–718, 1986.

Ulmer et al., "Heterologous Protection Against Influenza by Injection of DNA Encoding a Viral Protein," *Science*, 259:1745–1749, 1993.

Wada, Aota, Tsuchiya, Ishibashi, Gojobori, Ikemura, "Codon Usage Tabulated form the GenBank Genetic Sequence Data," *Nucleic Acids Research*, 18(Supplement):2367–2411, 1990.

Walsh, Nienhuis, Samulski, Brown, Miller, Young, Liu, "Phenotypic correction of Fanconi anemia in human hematopoietic cells with a recombinant adeno-associated virus vector," *Proc. Natl. Acad. Sci. USA*, 89:7257–7261, 1994.

Walsh, Nienhuis, Samulski, Brown, Miller, Young, Liu, "Phenotypic correction of Fanconi anemia in human hematopoietic cells with a recombinant adeno-associated virus vector," *J. Clin. Invest.*, 94:1440–1448, 1994.

Wampler et al., *Biochem. Biophys. Acta.* 314:104–109, 1973.

Wang and Hazelrigg, *Nature*, 369:400–403, 1994.

Wang et al, *Proc. Natl. Acad. Sci. USA*, 90:4156–4160, 1993.

Ward and Bokman, Biochemistry, 21:4535–4540, 1982.

Ward, Cody, Hart, Cormier, "Adeno-Associated Virus DNA Replication in vitro: Activation by a Maltose Binding Protein/Rep 68 Fusion Protein," *J. Virol.*, 68:6029–6037, 1994.

Ward et al., "Spectrophotometric Identity of the Energy-Transfer Chromophores in Renilla And Aequorea Green Fluorescent Proteins," *Photochem. Photobiol.*, 31:611–615, 1980.

Ward et al., *Photochem. Photobiol.*, 35:803–808, 1982.

Ward, *In: Bioluminescence and Chemiluminescence: Basic Chemistry and Analytical Applications* (DeLuca and McElroy, eds.), Academic Press, pp. 235–252, 1981.

Wei, Wei, Samulski, Barranger, "Expression of the human glucocerebrosidase and arylsulfatase A genes in murine and patient primary fibroblasts transduced by an adeno-associated virus vector," *Gene Therapy*, 1:261–268, 1994.

Yang, Chen, Trempe, "Characterization of cell lines that inducibly express the adeno-associated virus Rep proteins," *J. Virol.*, 68:4847–4856, 1994.

Yoder, Kang, Zhou, Luo, Srivastava, "In vivo gene transfer in murine hematopoietic reconstituting stem cells mediated by the adeno-associated virus 2-based vectors," *Blood*, 82:suppl. 1:347A, 1994.

Welch, *Scientific American*, p. 56, May, 1993.

Whitton et al., *J. Virol.* 67:(1)348–352,1993.

Wigler et al., *Cell*, 11:223, 1977.

Wigler et al., *Proc. Natl. Acad. Sci. USA*, 77:3567, 1980.

Wolff, Malone, Williams, Chong, Acsadi, Jani, Felgner, "Direct gene transfer into mouse muscle in vivo, *Science*, 247:1465–1468, 1990.

Youvan, "Imaging sequence space," *Nature*, 369:79–80, 1994.

Youvan et al., "Digital imaging spectroscopy for massively parallel screening of mutants," *Methods in Enzymology*, 246:732–748, 1995.

Zhou, Broxmyer, Cooper, Harrington, Srivastava, "Adeno-associated virus 2 mediated gene transfer in murine hematopoietic cells," *Exp. Hematol.*, (NY). 21:928–933, 1993.

Zhou, Cooper, Kang, Ruggieri, Heimfeld, Srivastava, Broxmeyer, "Adeno-associated virus 2-mediated high efficiency gene transfer into immature and mature subsets of hematopoietic progenitor cells in human umbilical cord blood," *J.Exp.Med.*, 179:1867–1875, 1994.

Zhu, et al., *Science*, 261:209–211, 1993.

What is claimed is:

1. A humanized green fluorescent protein (GFP) gene comprising the sequence of SEQ ID NO:3 wherein TTC encoding phenylalanine at position 64 and TCT encoding serine at position 65 is replaced by CTG and ACC, respectively.

2. A recombinant AAV vector comprising the nucleic acid sequence of SEQ ID NO:15.

3. A recombinant AAV vector comprising the nucleic acid sequence of SEQ ID NO:17.

4. A recombinant AAV vector comprising the nucleic acid sequence of SEQ ID NO:19.

5. A humanized GFP gene encoding a polypeptide having the amino acid sequence of SEQ ID NO:18.

6. A humanized GFP gene encoding a polypeptide having the amino acid sequence of SEQ ID NO:20.

7. A humanized GFP gene operatively fused 5' to a nuclear targeting sequence.

8. The humanized GFP of claim 7 wherein the nuclear targeting sequence is SV40 large T-antigen nuclear localization signal.

9. The humanized GFP of claim 8 wherein the GFP gene is modified to express leucine64 in place of phenylalanine64 and threonine 65 in place of serine 65.

10. A humanized GFP gene of comprising the sequence of SEQ ID NO. 19 wherein said gene is modified at position 1210, 1211 and 1212 (CAT) and at 1457, 1458 and 1459.

11. The humanized GFP of claim 10 wherein the nuclear targeting sequence comprises nucleotides 987–1014 of SEQ ID NO. 19.

* * * * *

UNITED STATES PATENT AND TRADEMARK OFFICE
CERTIFICATE OF CORRECTION

PATENT NO.    : 6,020,192
DATED         : February 1, 2000
INVENTOR(S)   : Muzyczka et al.

It is certified that error appears in the above-identified patent and that said Letters Patent is hereby corrected as shown below:

In claim 10, column 94, line 42, after 'gene', delete "of".

Signed and Sealed this

Tenth Day of October, 2000

Attest:

Q. TODD DICKINSON

*Attesting Officer*    *Director of Patents and Trademarks*

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 717 base pairs
      (B) TYPE: nucleic acid
      (C) STRANDEDNESS: single
      (D) TOPOLOGY: linear (xi) SEQUENCE DESCRIPTION: SEQ ID NO:1:

```
ATGAGTAAAG GAGAAGAACT TTTCACTGGA GTTGTCCCAA TTCTTGTTGA ATTAGATGGT      60

GATGTTAATG GGCACAAATT TTCTGTCAGT GGAGAGGGTG AAGGTGATGC AACATACGGA     120

AAACTTACCC TTAAATTTAT TTGCACTACT GGAAAACTAC CTGTTCCATG GCCAACACTT     180

GTCACTACTT TCTCTTATGG TGTTCAATGC TTTTCAAGAT ACCCAGATCA TATGAAACAG     240

CATGACTTTT TCAAGAGTGC CATGCCCGAA GGTTATGTAC AGGAAAGAAC TATATTTTTC     300

AAAGATGACG GGAACTACAA GACACGTGCT GAAGTCAAGT TTGAAGGTGA TACCCTTGTT     360

AATAGAATCG AGTTAAAAGG TATTGATTTT AAAGAAGATG GAAACATTCT TGGACACAAA     420

TTGGAATACA ACTATAACTC ACACAATGTA TACATCATGG CAGACAAACA AAAGAATGGA     480

ATCAAAGTTA ACTTCAAAAT TAGACACAAC ATTGAAGATG GAAGCGTTCA ACTAGCAGAC     540

CATTATCAAC AAAATACTCC AATTGGCGAT GGCCCTGTCC TTTTACCAGA CAACCATTAC     600

CTGTCCACAC AATCTGCCCT TTCGAAAGAT CCCAACGAAA AGAGAGACCA CATGGTCCTT     660

CTTGAGTTTG TAACAGCTGC TGGGATTACA CATGGCATGG ATGAACTATA CAAATAA       717
```

(2) INFORMATION FOR SEQ ID NO:2:

(i) SEQUENCE CHARACTERISTICS:
      (A) LENGTH: 238 amino acids
      (B) TYPE: amino acid
      (C) STRANDEDNESS:

(D) TOPOLOGY: linear (ix) FEATURE:
                (A) NAME/KEY: Modified-site
                (B) LOCATION: 65
                (D) OTHER INFORMATION: /product= "OTHER"
                    /note= "Xaa = Ser or Ther"

(ix) FEATURE:
                (A) NAME/KEY: Modified-site
                (B) LOCATION: 66
                (D) OTHER INFORMATION: /product= "OTHER"
                    /note= "Xaa = Tyr or His"

(xi) SEQUENCE DESCRIPTION: SEQ ID NO:2:

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Xaa Xaa Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
25                  230                 235

(2) INFORMATION FOR SEQ ID NO:3:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 193
        (D) OTHER INFORMATION: /mod_base= OTHER
            /note= "W = A or T"

(ix) FEATURE:
        (A) NAME/KEY: modified_base
        (B) LOCATION: 195..196
        (D) OTHER INFORMATION: /mod_base= OTHER /note= "Y = C or T"

(xi) SEQUENCE DESCRIPTION: SEQ ID NO:3:

| | | | | | |
|---|---|---|---|---|---|
| ATGAGCAAGG | GCGAGGAACT | GTTCACTGGC | GTGGTCCCAA | TTCTCGTGGA | ACTGGATGGC | 60
| GATGTGAATG | GGCACAAATT | TTCTGTCAGC | GGAGAGGGTG | AAGGTGATGC | CACATACGGA | 120
| AAGCTCACCC | TGAAATTCAT | CTGCACCACT | GGAAAGCTCC | CTGTGCCATG | GCCAACACTG | 180
| GTCACTACCT | TCWCYYATGG | CGTGCAGTGC | TTTTCCAGAT | ACCCAGACCA | TATGAAGCAG | 240
| CATGACTTTT | TCAAGAGCGC | CATGCCCGAG | GGCTATGTGC | AGGAGAGAAC | CATCTTTTTC | 300
| AAAGATGACG | GGAACTACAA | GACCCGCGCT | GAAGTCAAGT | TCGAAGGTGA | CACCCTGGTG | 360
| AATAGAATCG | AGTTGAAGGG | CATTGACTTT | AAGGAAGATG | GAAACATTCT | CGGCCACAAG | 420
| CTGGAATACA | ACTATAACTC | CCACAATGTG | TACATCATGG | CCGACAAGCA | AAAGAATGGC | 480
| ATCAAGGTCA | ACTTCAAGAT | CAGACACAAC | ATTGAGGATG | GATCCGTGCA | GCTGGCCGAC | 540
| CATTATCAAC | AGAACACTCC | AATCGGCGAC | GGCCCTGTGC | TCCTCCCAGA | CAACCATTAC | 600
| CTGTCCACCC | AGTCTGCCCT | GTCTAAAGAT | CCCAACGAAA | AGAGAGACCA | CATGGTCCTG | 660
| CTGGAGTTTG | TGACCGCTGC | TGGGATCACA | CATGGCATGG | ACGAGCTGTA | CAAGTGA | 717

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:4:

Phe Ser Tyr Gly Val Gln
1           5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:5:

Met Gly Tyr Gly Val Leu
1           5

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:6:

Pro Pro Lys Lys Lys Arg Lys Val
1           5

(2) INFORMATION FOR SEQ ID NO:7:

(i) SEQUENCE CHARACTERISTICS:
        (A) LENGTH: 18 amino acids
        (B) TYPE: amino acid
        (C) STRANDEDNESS:
        (D) TOPOLOGY: linear (xi) SEQUENCE DESCRIPTION: SEQ ID NO:7:

Met Leu Ser Leu Arg Gln Ser Ile Arg Phe Phe Lys Pro Ala Thr Arg
1               5                   10                  15

Thr Leu (2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 7
        (D) OTHER INFORMATION: /mod_base= OTHER
            /note= "R = A or G"

(xi) SEQUENCE DESCRIPTION: SEQ ID NO:8:

GCCGCCRCCA TG                                                          12

(2) INFORMATION FOR SEQ ID NO:9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:9:

TGCTCTAGAG CGGCCGCCGC CACCATGAGC AAGGGCGAGG AACTG                      45

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:10:

CGGAAGCTTG CGGCCGCTCA CTTGTACAGC TCGTCCAT                              38

(2) INFORMATION FOR SEQ ID NO:11:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:11:

GCTTCATATG GTCTGGGTAT CTGGAAAAGC ACTGCACGCC ATACCAGAAG GTAG            54

(2) INFORMATION FOR SEQ ID NO:12:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:12:

GCTTCATATG GTCTGGGTAT CTGGAAAAGC ACTGCACGCC ATGAGAGAAG GTAG            54

(2) INFORMATION FOR SEQ ID NO:13:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (xi) SEQUENCE DESCRIPTION: SEQ ID NO:13:

TGCTCTAGAG CGGCCGCCGC CACCATGGTG CCCAAGAAGA AGAGGAAGGT GATGAGCAAG    60

GGCGAG                                                              66

(2) INFORMATION FOR SEQ ID NO:14:

(i) SEQUENCE CHARACTERISTICS:
            (A) LENGTH: 5030 base pairs
            (B) TYPE: nucleic acid
            (C) STRANDEDNESS: single
            (D) TOPOLOGY: linear (xi) SEQUENCE DESCRIPTION: SEQ ID NO:14:

GGCCGCTCTA GCTTGGGATC TTTGTGAAGG AACCTTACTT CTGTGGTGTG ACATAATTGG    60

ACAAACTACC TACAGAGATT TAAAGCTCTA AGGTAAATAT AAAATTTTTA AGTGTATAAT   120

GTGTTAAACT AGCTGCATAT GCTTGCTGCT TGAGAGTTTT GCTTACTGAG TATGATTTAT   180

GAAAATATTA TACACAGGAG CTAGTGATTC TAATTGTTTG TGTATTTTAG ATTCACAGTC   240

CCAAGGCTCA TTTCAGGCCC CTCAGTCCTC ACAGTCTGTT CATGATCATA ATCAGCCATA   300

CCACATTTGT AGAGGTTTTA CTTGCTTTAA AAAACCTCCC ACACCTCCCC CTGAACCTGA   360

AACATAAAAT GAATGCAATT GTTGTTGTTA ACTTGTTTAT TGCAGCTTAT AATGGTTACA   420

AATAAAGCAA TAGCATCACA AATTTCACAA ATAAAGCATT TTTTTCACTG CATTCTAGTT   480

GTGGTTTGTC CAAACTCATC AATGTATCTT ATCATGTCTG GATCGATCCT GCATTAATGA   540

ATCGGCCAAC GCGCGGGGAG AGGCGGTTTG CGTATTGGCT GGCGTAATAG CGAAGAGGCC   600

CGCACCGATC GCCCTTCCCA ACAGTTGCGC AGCCTGAATG GCGAATGGAC GCGCCCTGTA   660

GCGGCGCATT AAGCGCGGCG GGTGTGGTGG TTACGCGCAG CGTGACCGCT ACACTTGCCA   720

GCGCCCTAGC GCCCGCTCCT TTCGCTTTCT TCCCTTCCTT TCTCGCCACG TTCGCCGGCT   780

TTCCCCGTCA AGCTCTAAAT CGGGGGCTCC CTTTAGGGTT CCGATTTAGT GCTTTACGGC   840

ACCTCGACCC CAAAAAACTT GATTAGGGTG ATGGTTCACG TAGTGGGCCA TCGCCCTGAT   900

AGACGGTTTT TCGCCCTTTG ACGTTGGAGT CCACGTTCTT TAATAGTGGA CTCTTGTTCC   960

AAACTGGAAC AACACTCAAC CCTATCTCGG TCTATTCTTT TGATTTATAA GGGATTTTGC  1020

CGATTTCGGC CTATTGGTTA AAAAATGAGC TGATTTAACA AAAATTTAAC GCGAATTTTA  1080

ACAAAATATT AACGTTTACA ATTTCAGGTG GCACTTTTCG GGGAAATGTG CGCGGAACCC  1140

CTATTTGTTT ATTTTTCTAA ATACATTCAA ATATGTATCC GCTCATGCCA GGTCTTGGAC  1200

TGGTGAGAAC GGCTTGCTCG GCAGCTTCGA TGTGTGCTGG AGGGAGAATA AAGGTCTAAG  1260

ATGTGCGATA GAGGGAAGTC GCATTGAATT ATGTGCTGTG TAGGGATCGC TGGTATCAAA  1320

TATGTGTGCC CACCCCTGGC ATGAGACAAT AACCCTGATA AATGCTTCAA TAATATTGAA  1380

AAAGGAAGAG TATGAGTATT CAACATTTCC GTGTCGCCCT TATTCCCTTT TTTGCGGCAT  1440

TTTGCCTTCC TGTTTTTGCT CACCCAGAAA CGCTGGTGAA AGTAAAAGAT GCTGAAGATC  1500

AGTTGGGTGC ACGAGTGGGT TACATCGAAC TGGATCTCAA CAGCGGTAAG ATCCTTGAGA  1560

GTTTTCGCCC CGAAGAACGT TTTCAATGA TGAGCACTTT TAAAGTTCTG CTATGTGGCG  1620

CGGTATTATC CCGTATTGAC GCCGGGCAAG AGCAACTCGG TCGCCGCATA CACTATTCTC  1680

AGAATGACTT GGTTGAGTAC TCACCAGTCA CAGAAAAGCA TCTTACGGAT GGCATGACAG  1740

```
TAAGAGAATT ATGCAGTGCT GCCATAACCA TGAGTGATAA CACTGCGGCC AACTTACTTC    1800

TGACAACGAT CGGAGGACCG AAGGAGCTAA CCGCTTTTTT GCACAACATG GGGGATCATG    1860

TAACTCGCCT TGATCGTTGG GAACCGGAGC TGAATGAAGC CATACCAAAC GACGAGCGTG    1920

ACACCACGAT GCCTGTAGCA ATGGCAACAA CGTTGCGCAA ACTATTAACT GGCGAACTAC    1980

TTACTCTAGC TTCCCGGCAA CAATTAATAG ACTGGATGGA GGCGGATAAA GTTGCAGGAC    2040

CACTTCTGCG CTCGGCCCTT CCGGCTGGCT GGTTTATTGC TGATAAATCT GGAGCCGGTG    2100

AGCGTGGGTC TCGCGGTATC ATTGCAGCAC TGGGGCCAGA TGGTAAGCCC TCCCGTATCG    2160

TAGTTATCTA CACGACGGGG AGTCAGGCAA CTATGGATGA ACGAAATAGA CAGATCGCTG    2220

AGATAGGTGC CTCACTGATT AAGCATTGGT AACTGTCAGA CCAAGTTTAC TCATATATAC    2280

TTTAGATTGA TTTAAAACTT CATTTTTAAT TTAAAAGGAT CTAGGTGAAG ATCCTTTTTG    2340

ATAATCTCAT GCCATAACTT CGTATAATGT ATGCTATACG AAGTTATGGC ATGACCAAAA    2400

TCCCTTAACG TGAGTTTTCG TTCCACTGAG CGTCAGACCC CGTAGAAAAG ATCAAAGGAT    2460

CTTCTTGAGA TCCTTTTTTT CTGCGCGTAA TCTGCTGCTT GCAAACAAAA AAACCACCGC    2520

TACCAGCGGT GGTTTGTTTG CCGGATCAAG AGCTACCAAC TCTTTTTCCG AAGGTAACTG    2580

GCTTCAGCAG AGCGCAGATA CCAAATACTG TCCTTCTAGT GTAGCCGTAG TTAGGCCACC    2640

ACTTCAAGAA CTCTGTAGCA CCGCCTACAT ACCTCGCTCT GCTAATCCTG TTACCAGTGG    2700

CTGCTGCCAG TGGCGATAAG TCGTGTCTTA CCGGGTTGGA CTCAAGACGA TAGTTACCGG    2760

ATAAGGCGCA GCGGTCGGGC TGAACGGGGG GTTCGTGCAC ACAGCCCAGC TTGGAGCGAA    2820

CGACCTACAC CGAACTGAGA TACCTACAGC GTGAGCATTG AGAAAGCGCC ACGCTTCCCG    2880

AAGGGAGAAA GGCGGACAGG TATCCGGTAA GCGGCAGGGT CGGAACAGGA GAGCGCACGA    2940

GGGAGCTTCC AGGGGGAAAC GCCTGGTATC TTTATAGTCC TGTCGGGTTT CGCCACCTCT    3000

GACTTGAGCG TCGATTTTTG TGATGCTCGT CAGGGGGGCG GAGCCTATGG AAAAACGCCA    3060

GCAACGCGGC CTTTTTACGG TTCCTGGCCT TTTGCTGGCC TTTTGCTCAC ATGTTCTTTC    3120

CTGCGTTATC CCCTGATTCT GTGGATAACC GTATTACCGC CTTTGAGTGA GCTGATACCG    3180

CTCGCCGCAG CCGAACGACC GAGCGCAGCG AGTCAGTGAG CGAGGAAGCG GAAGAGCGCC    3240

CAATACGCAA ACCGCCTCTC CCCGCGCGTT GGCCGATTCA TTAATGCAGA GCTTGCAATT    3300

CGCGCGTTTT TCAATATTAT TGAAGCATTT ATCAGGGTTA TTGTCTCATG AGCGGATACA    3360

TATTTGAATG TATTTAGAAA AATAAACAAA TAGGGGTTCC GCGCACATTT CCCCGAAAAG    3420

TGCCACCTGA CGTCTAAGAA ACCATTATTA TCATGACATT AACCTATAAA AATAGGCGTA    3480

TACGAGGCCC TTTCACTCAT TAGGCACCCC AGGCTTTACA CTTTATAGCT TCCGGCTCGT    3540

ATAATGTGTG GAATTGTGAG CGGATAACAA TTTCACACAG GAAACAGCAT CGTGCAGGTC    3600

GTTACATAAC TTACGGTAAA TGGCCCGCCT GGCTGACCGC CCAACGACCC CGCCCATTG    3660

ACGTCAATAA TGACGTATGT TCCCATAGTA ACGCCAATAG GGACTTTCCA TTGACGTCAA    3720

TGGGTGGAGT ATTTACGGTA AACTGCCCAC TTGGCAGTAC ATCAAGTGTA TCATATGCCA    3780

AGTACGCCCC CTATTGACGT CAATGACGGT AAATGGCCCG CCTGGCATTA TGCCCAGTAC    3840

ATGACCTTAT GGGACTTTCC TACTTGGCAG TACATCTACG TATTAGTCAT CGCTATTACC    3900

ATGGTGATGC GGTTTTGGCA GTACATCAAT GGGCGTGGAT AGCGGTTTGA CTCACGGGGA    3960

TTTCCAAGTC TCCACCCCAT TGACGTCAAT GGGAGTTTGT TTTGGCACCA AAATCAACGG    4020

GACTTTCCAA AATGTCGTAA CAACTCCGCC CCATTGACGC AAATGGGCGG TAGGCGTGTA    4080

CGGTGGGAGG TCTATATAAG CAGAGCTCGT TTAGTGAACC GTCAGATCGC CTGGAGACGC    4140
```

```
CATCCACGCT GTTTTGACCT CCATAGAAGA CACCGGGACC GATCCAGCCT CCGGACTCTA      4200

GCCTAGGCTT TTGCAAAAAG CTATTTAGGT GACACTATAG AAGGTACGCC TGCAGGTACC      4260

GGTCCGGAAT TCCCGGGTCG ACGAGCTCAC TAGTCGGCGG CCGCCGCCAC CATGAGCAAG      4320

GGCGAGGAAC TGTTCACTGG CGTGGTCCCA ATTCTCGTGG AACTGGATGG CGATGTGAAT      4380

GGGCACAAAT TTTCTGTCAG CGGAGAGGGT GAAGGTGATG CCACATACGG AAAGCTCACC      4440

CTGAAATTCA TCTGCACCAC TGGAAAGCTC CCTGTGCCAT GGCCAACACT GGTCACTACC      4500

TTCACCTATG GCGTGCAGTG CTTTTCCAGA TACCCAGACC ATATGAAGCA GCATGACTTT      4560

TTCAAGAGCG CCATGCCCGA GGGCTATGTG CAGGAGAGAA CCATCTTTTT CAAAGATGAC      4620

GGGAACTACA AGACCCGCGC TGAAGTCAAG TTCGAAGGTG ACACCCTGGT GAATAGAATC      4680

GAGTTGAAGG GCATTGACTT TAAGGAAGAT GGAAACATTC TCGGCCACAA GCTGGAATAC      4740

AACTATAACT CCCACAATGT GTACATCATG GCCGACAAGC AAAAGAATGG CATCAAGGTC      4800

AACTTCAAGA TCAGACACAA CATTGAGGAT GGATCCGTGC AGCTGGCCGA CCATTATCAA      4860

CAGAACACTC CAATCGGCGA CGGCCCTGTG CTCCTCCCAG ACAACCATTA CCTGTCCACC      4920

CAGTCTGCCC TGTCTAAAGA TCCCAACGAA AAGAGAGACC ACATGGTCCT GCTGGAGTTT      4980

GTGACCGCTG CTGGGATCAC ACATGGCATG GACGAGCTGT ACAAGTGAGC                 5030

(2) INFORMATION FOR SEQ ID NO:15:

(i) SEQUENCE CHARACTERISTICS:
        (A) LENGTH: 6253 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 988..1701

(xi) SEQUENCE DESCRIPTION: SEQ ID NO:15:

GGGGGGGGGG GGGGGGGGTT GGCCACTCCC TCTCTGCGCG CTCGCTCGCT CACTGAGGCC        60

GGGCGACCAA AGGTCGCCCG ACGCCCGGGC TTTGCCCGGG CGGCCTCAGT GAGCGAGCGA       120

GCGCGCAGAG AGGGAGTGGC CAACTCCATC ACTAGGGGTT CCTAGATCTG AATTCGGTAC       180

CCGTTACATA ACTTACGGTA AATGGCCCGC CTGGCTGACC GCCCAACGAC CCCCGCCCAT       240

TGACGTCAAT AATGACGTAT GTTCCCATAG TAACGCCAAT AGGGACTTTC CATTGACGTC       300

AATGGGTGGA GTATTTACGG TAAACTGCCC ACTTGGCAGT ACATCAAGTG TATCATATGC       360

CAAGTACGCC CCCTATTGAC GTCAATGACG GTAAATGGCC CGCCTGGCAT TATGCCCAGT       420

ACATGACCTT ATGGGACTTT CCTACTTGGC AGTACATCTA CGTATTAGTC ATCGCTATTA       480

CCATGGTGAT GCGGTTTTGG CAGTACATCA ATGGGCGTGG ATAGCGGTTT GACTCACGGG       540

GATTTCCAAG TCTCCACCCC ATTGACGTCA ATGGGAGTTT GTTTTGGCAC CAAAATCAAC       600

GGGACTTTCC AAAATGTCGT AACAACTCCG CCCCATTGAC GCAAATGGGC GGTAGGCGTG       660

TACGGTGGGA GGTCTATATA AGCAGAGCTC GTTTAGTGAA CCGTCAGATC GCCTGGAGAC       720

GCCATCCACG CTGTTTTGAC CTCCATAGAA GACACCGGGA CCGATCCAGC CTCCGGACTC       780

TAGAGGATCC GGTACTCGAG GAACTGAAAA ACCAGAAAGT TAACTGGTAA GTTTAGTCTT       840

TTTGTCTTTT ATTTCAGGTC CCGGATCCGG TGGTGGTGCA AATCAAAGAA CTGCTCCTCA       900

GTGGATGTTG CCTTTACTTC TAGGCCTGTA CGGAAGTGTT ACTTCTGCTC TAAAAGCTGC       960

GGAATTGTAC CCGCGGCCGC CGCCACC ATG AGC AAG GGC GAG GAA CTG TTC         1011
                               Met Ser Lys Gly Glu Glu Leu Phe
```

-continued

```
                    1               5
ACT GGC GTG GTC CCA ATT CTC GTG GAA CTG GAT GGC GAT GTG AAT GGG      1059
Thr Gly Val Val Pro Ile Leu Val Glu Leu Asp Gly Asp Val Asn Gly
     10              15                  20

CAC AAA TTT TCT GTC AGC GGA GAG GGT GAA GGT GAT GCC ACA TAC GGA      1107
His Lys Phe Ser Val Ser Gly Glu Gly Glu Gly Asp Ala Thr Tyr Gly
 25              30                  35                   40

AAG CTC ACC CTG AAA TTC ATC TGC ACC ACT GGA AAG CTC CCT GTG CCA      1155
Lys Leu Thr Leu Lys Phe Ile Cys Thr Thr Gly Lys Leu Pro Val Pro
             45                  50                  55

TGG CCA ACA CTG GTC ACT ACC CTG ACC TAT GGC GTG CAG TGC TTT TCC      1203
Trp Pro Thr Leu Val Thr Thr Leu Thr Tyr Gly Val Gln Cys Phe Ser
             60                  65                  70

AGA TAC CCA GAC CAT ATG AAG CAG CAT GAC TTT TTC AAG AGC GCC ATG      1251
Arg Tyr Pro Asp His Met Lys Gln His Asp Phe Phe Lys Ser Ala Met
         75                  80                  85

CCC GAG GGC TAT GTG CAG GAG AGA ACC ATC TTT TTC AAA GAT GAC GGG      1299
Pro Glu Gly Tyr Val Gln Glu Arg Thr Ile Phe Phe Lys Asp Asp Gly
         90                  95                  100

AAC TAC AAG ACC CGC GCT GAA GTC AAG TTC GAA GGT GAC ACC CTG GTG      1347
Asn Tyr Lys Thr Arg Ala Glu Val Lys Phe Glu Gly Asp Thr Leu Val
105                  110                 115                 120

AAT AGA ATC GAG CTG AAG GGC ATT GAC TTT AAG GAG GAT GGA AAC ATT      1395
Asn Arg Ile Glu Leu Lys Gly Ile Asp Phe Lys Glu Asp Gly Asn Ile
                 125                 130                 135

CTC GGC CAC AAG CTG GAA TAC AAC TAT AAC TCC CAC AAT GTG TAC ATC      1443
Leu Gly His Lys Leu Glu Tyr Asn Tyr Asn Ser His Asn Val Tyr Ile
             140                 145                 150

ATG GCC GAC AAG CAA AAG AAT GGC ATC AAG GTC AAC TTC AAG ATC AGA      1491
Met Ala Asp Lys Gln Lys Asn Gly Ile Lys Val Asn Phe Lys Ile Arg
             155                 160                 165

CAC AAC ATT GAG GAT GGA TCC GTG CAG CTG GCC GAC CAT TAT CAA CAG      1539
His Asn Ile Glu Asp Gly Ser Val Gln Leu Ala Asp His Tyr Gln Gln
         170                 175                 180

AAC ACT CCA ATC GGC GAC GGC CCT GTG CTC CTC CCA GAC AAC CAT TAC      1587
Asn Thr Pro Ile Gly Asp Gly Pro Val Leu Leu Pro Asp Asn His Tyr
185                 190                 195                 200

CTG TCC ACC CAG TCT GCC CTG TCT AAA GAT CCC AAC GAA AAG AGA GAC      1635
Leu Ser Thr Gln Ser Ala Leu Ser Lys Asp Pro Asn Glu Lys Arg Asp
                 205                 210                 215

CAC ATG GTC CTG CTG GAG TTT GTG ACC GCT GCT GGG ATC ACA CAT GGC      1683
His Met Val Leu Leu Glu Phe Val Thr Ala Ala Gly Ile Thr His Gly
             220                 225                 230

ATG GAC GAG CTG TAC AAG TGAGCGGCCG CGGGGATCCA GACATGATAA             1731
Met Asp Glu Leu Tyr Lys
             235

GATACATTGA TGAGTTTGGA CAAACCACAA CTAGAATGCA GTGAAAAAAA TGCTTTATTT    1791

GTGAAATTTG TGATGCTATT GCTTTATTTG TAACCATTAT AAGCTGCAAT AAACAAGTTA    1851

ACAACAACAA TTGCATTCAT TTTATGTTTC AGGTTCAGGG GGAGGTGTGG GAGGTTTTTT    1911

AGTCGACCTC GAGCAGTGTG GTTTTGCAAG AGGAAGCAAA AAGCCTCTCC ACCCAGGCCT    1971

GGAATGTTTC CACCCAAGTC GAAGGCAGTG TGGTTTTGCA AGAGGAAGCA AAAAGCCTCT    2031

CCACCCAGGC CTGGAATGTT TCCACCCAAT GTCGAGCAAC CCCGCCCAGC GTCTTGTCAT    2091

TGGCGAATTC GAACACGCAG ATGCAGTCGG GGCGGCGCGG TCCCAGGTCC ACTTCGCATA    2151

TTAAGGTGAC GCGTGTGGCC TCGAACACCG AGCGACCCTG CAGCCAATAT GGGATCGGCC    2211

ATTGAACAAG ATGGATTGCA CGCAGGTTCT CCGGCCGCTT GGGTGGAGAG GCTATTCGGC    2271
```

```
TATGACTGGG CACAACAGAC AATCGGCTGC TCTGATGCCG CCGTGTTCCG GCTGTCAGCG    2331

CAGGGGCGCC CGGTTCTTTT TGTCAAGACC GACCTGTCCG GTGCCCTGAA TGAACTGCAG    2391

GACGAGGCAG CGCGGCTATC GTGGCTGGCC ACGACGGGG TTCCTTGCGC AGCTGTGCTC     2451

GACGTTGTCA CTGAAGCGGG AAGGGACTGG CTGCTATTGG GCGAAGTGCC GGGGCAGGAT    2511

CTCCTGTCAT CTCACCTTGC TCCTGCCGAG AAAGTATCCA TCATGGCTGA TGCAATGCGG    2571

CGGCTGCATA CGCTTGATCC GGCTACCTGC CCATTCGACC ACCAAGCGAA ACATCGCATC    2631

GAGCGAGCAC GTACTCGGAT GGAAGCCGGT CTTGTCGATC AGGATGATCT GGACGAAGAG    2691

CATCAGGGGC TCGCGCCAGC CGAACTGTTC GCCAGGCTCA AGGCGCGCAT GCCCGACGGC    2751

GAGGATCTCG TCGTGACCCA TGGCGATGCC TGCTTGCCGA ATATCATGGT GGAAAATGGC    2811

CGCTTTTCTG GATTCATCGA CTGTGGCCGG CTGGGTGTGG CGGACCGCTA TCAGGACATA    2871

GCGTTGGCTA CCCGTGATAT TGCTGAAGAG CTTGGCGGCG AATGGGCTGA CCGCTTCCTC    2931

GTGCTTTACG GTATCGCCGC TCCCGATTCG CAGCGCATCG CCTTCTATCG CCTTCTTGAC    2991

GAGTTCTTCT GAGGGGATCC GTCGACTAGA GCTCGCTGAT CAGCCTCGAC TGTGCCTTCT    3051

AGTTGCCAGC CATCTGTTGT TTGCCCCTCC CCCGTGCCTT CCTTGACCCT GGAAGGTGCC    3111

ACTCCCACTG TCCTTTCCTA ATAAAATGAG GAAATTGCAT CGCATTGTCT GAGTAGGTGT    3171

CATTCTATTC TGGGGGGTGG GGTGGGGCAG GACAGCAAGG GGGAGGATTG GGAAGACAAT    3231

AGCAGGCATG CTGGGGAGAG ATCTAGGAAC CCCTAGTGAT GGAGTTGGCC ACTCCCTCTC    3291

TGCGCGCTCG CTCGCTCACT GAGGCCGCCC GGGCAAAGCC CGGGCGTCGG GCGACCTTTG    3351

GTCGCCCGGC CTCAGTGAGC GAGCGAGCGC GCAGAGAGGG AGTGGCCAAC CCCCCCCCCC    3411

CCCCCCCTGC AGCCCTGCAT TAATGAATCG GCCAACGCGC GGGGAGAGGC GGTTTGCGTA    3471

TTGGGCGCTC TTCCGCTTCC TCGCTCACTG ACTCGCTGCG CTCGGTCGTT CGGCTGCGGC    3531

GAGCGGTATC AGCTCACTCA AAGGCGGTAA TACGGTTATC CACAGAATCA GGGGATAACG    3591

CAGGAAAGAA CATGTGAGCA AAAGGCCAGC AAAAGGCCAG GAACCGTAAA AAGGCCGCGT    3651

TGCTGGCGTT TTTCCATAGG CTCCGCCCCC CTGACGAGCA TCACAAAAAT CGACGCTCAA    3711

GTCAGAGGTG GCGAAACCCG ACAGGACTAT AAAGATACCA GGCGTTTCCC CCTGGAAGCT    3771

CCCTCGTGCG CTCTCCTGTT CCGACCCTGC CGCTTACCGG ATACCTGTCC GCCTTTCTCC    3831

CTTCGGGAAG CGTGGCGCTT TCTCAATGCT CACGCTGTAG GTATCTCAGT TCGGTGTAGG    3891

TCGTTCGCTC CAAGCTGGGC TGTGTGCACG AACCCCCCGT TCAGCCCGAC CGCTGCGCCT    3951

TATCCGGTAA CTATCGTCTT GAGTCCAACC CGGTAAGACA CGACTTATCG CCACTGGCAG    4011

CAGCCACTGG TAACAGGATT AGCAGAGCGA GGTATGTAGG CGGTGCTACA GAGTTCTTGA    4071

AGTGGTGGCC TAACTACGGC TACACTAGAA GGACAGTATT TGGTATCTGC GCTCTGCTGA    4131

AGCCAGTTAC CTTCGGAAAA AGAGTTGGTA GCTCTTGATC CGGCAAACAA ACCACCGCTG    4191

GTAGCGGTGG TTTTTTTGTT TGCAAGCAGC AGATTACGCG CAGAAAAAAA GGATCTCAAG    4251

AAGATCCTTT GATCTTTTCT ACGGGGTCTG ACGCTCAGTG GAACGAAAAC TCACGTTAAG    4311

GGATTTTGGT CATGAGATTA TCAAAAAGGA TCTTCACCTA GATCCTTTTA AATTAAAAAT    4371

GAAGTTTTAA ATCAATCTAA AGTATATATG AGTAAACTTG GTCTGACAGT TACCAATGCT    4431

TAATCAGTGA GGCACCTATC TCAGCGATCT GTCTATTTCG TTCATCCATA GTTGCCTGAC    4491

TCCCCGTCGT GTAGATAACT ACGATACGGG AGGGCTTACC ATCTGGCCCC AGTGCTGCAA    4551

TGATACCGCG AGACCCACGC TCACCGGCTC CAGATTTATC AGCAATAAAC CAGCCAGCCG    4611

GAAGGGCCGA GCGCAGAAGT GGTCCTGCAA CTTTATCCGC CTCCATCCAG TCTATTAATT    4671
```

```
GTTGCCGGGA AGCTAGAGTA AGTAGTTCGC CAGTTAATAG TTTGCGCAAC GTTGTTGCCA    4731

TTGCTACAGG CATCGTGGTG TCACGCTCGT CGTTTGGTAT GGCTTCATTC AGCTCCGGTT    4791

CCCAACGATC AAGGCGAGTT ACATGATCCC CCATGTTGTG CAAAAAAGCG GTTAGCTCCT    4851

TCGGTCCTCC GATCGTTGTC AGAAGTAAGT TGGCCGCAGT GTTATCACTC ATGGTTATGG    4911

CAGCACTGCA TAATTCTCTT ACTGTCATGC CATCCGTAAG ATGCTTTTCT GTGACTGGTG    4971

AGTACTCAAC CAAGTCATTC TGAGAATAGT GTATGCGGCG ACCGAGTTGC TCTTGCCCGG    5031

CGTCAATACG GGATAATACC GCGCCACATA GCAGAACTTT AAAAGTGCTC ATCATTGGAA    5091

AACGTTCTTC GGGGCGAAAA CTCTCAAGGA TCTTACCGCT GTTGAGATCC AGTTCGATGT    5151

AACCCACTCG TGCACCCAAC TGATCTTCAG CATCTTTTAC TTTCACCAGC GTTTCTGGGT    5211

GAGCAAAAAC AGGAAGGCAA AATGCCGCAA AAAAGGGAAT AAGGGCGACA CGGAAATGTT    5271

GAATACTCAT ACTCTTCCTT TTTCAATATT ATTGAAGCAT TTATCAGGGT TATTGTCTCA    5331

TGAGCGGATA CATATTTGAA TGTATTTAGA AAAATAAACA AATAGGGGTT CCGCGCACAT    5391

TTCCCCGAAA AGTGCCACCT GACGTCTAAG AAACCATTAT TATCATGACA TTAACCTATA    5451

AAAATAGGCG TATCACGAGG CCCTTTCGTC TCGCGCGTTT CGGTGATGAC GGTGAAAACC    5511

TCTGACACAT GCAGCTCCCG GAGACGGTCA CAGCTTGTCT GTAAGCGGAT GCCGGGAGCA    5571

GACAAGCCCG TCAGGGCGCG TCAGCGGGTG TTGGCGGGTG TCGGGCTGG CTTAACTATG    5631

CGGCATCAGA GCAGATTGTA CTGAGAGTGC ACCATATGCG GTGTGAAATA CCGCACAGAT    5691

GCGTAAGGAG AAAATACCGC ATCAGGAAAT TGTAAACGTT AATATTTTGT TAAAATTCGC    5751

GTTAAATTTT TGTTAAATCA GCTCATTTTT TAACCAATAG GCCGAAATCG GCAAAATCCC    5811

TTATAAATCA AAAGAATAGA CCGAGATAGG GTTGAGTGTT GTTCCAGTTT GGAACAAGAG    5871

TCCACTATTA AAGAACGTGG ACTCCAACGT CAAAGGGCGA AAAACCGTCT ATCAGGGCGA    5931

TGGCCCACTA CGTGAACCAT CACCCTAATC AAGTTTTTTG GGGTCGAGGT GCCGTAAAGC    5991

ACTAAATCGG AACCCTAAAG GGAGCCCCCG ATTTAGAGCT TGACGGGGAA AGCCGGCGAA    6051

CGTGGCGAGA AAGGAAGGGA AGAAAGCGAA AGGAGCGGGC GCTAGGGCGC TGGCAAGTGT    6111

AGCGGTCACG CTGCGCGTAA CCACCACACC CGCCGCGCTT AATGCGCCGC TACAGGGCGC    6171

GTCGCGCCAT TCGCCATTCA GGCTACGCAA CTGTTGGGAA GGGCGATCGG TGCGGGCCTC    6231

TTCGCTATTA CGCCAGGCTG CA                                            6253
```

(2) INFORMATION FOR SEQ ID NO:16:

(i) SEQUENCE CHARACTERISTICS:
      (A) LENGTH: 238 amino acids
      (B) TYPE: amino acid
      (D) TOPOLOGY: linear (ii) MOLECULE TYPE: protein (xi) SEQUENCE DESCRIPTION: SEQ ID NO:16:

```
Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Leu
        50                  55                  60

Thr Tyr Gly Val Gln Cys Phe Ser Arg Tyr Pro Asp His Met Lys Gln
65                  70                  75                  80
```

His Asp Phe Phe Lys Ser Ala Met Pro Glu Gly Tyr Val Gln Glu Arg
            85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

(2) INFORMATION FOR SEQ ID NO:17:

(i) SEQUENCE CHARACTERISTICS:
       (A) LENGTH: 6280 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 988..1728

(xi) SEQUENCE DESCRIPTION: SEQ ID NO:17:

```
GGGGGGGGGG GGGGGGGGTT GGCCACTCCC TCTCTGCGCG CTCGCTCGCT CACTGAGGCC      60

GGGCGACCAA AGGTCGCCCG ACGCCCGGGC TTTGCCCGGG CGGCCTCAGT GAGCGAGCGA     120

GCGCGCAGAG AGGGAGTGGC CAACTCCATC ACTAGGGGTT CCTAGATCTG AATTCGGTAC     180

CCGTTACATA ACTTACGGTA AATGGCCCGC CTGGCTGACC GCCCAACGAC CCCCGCCCAT     240

TGACGTCAAT AATGACGTAT GTTCCCATAG TAACGCCAAT AGGGACTTTC CATTGACGTC     300

AATGGGTGGA GTATTTACGG TAAACTGCCC ACTTGGCAGT ACATCAAGTG TATCATATGC     360

CAAGTACGCC CCCTATTGAC GTCAATGACG GTAAATGGCC CGCCTGGCAT TATGCCCAGT     420

ACATGACCTT ATGGGACTTT CCTACTTGGC AGTACATCTA CGTATTAGTC ATCGCTATTA     480

CCATGGTGAT GCGGTTTTGG CAGTACATCA ATGGGCGTGG ATAGCGGTTT GACTCACGGG     540

GATTTCCAAG TCTCCACCCC ATTGACGTCA ATGGGAGTTT GTTTTGGCAC CAAAATCAAC     600

GGGACTTTCC AAAATGTCGT AACAACTCCG CCCCATTGAC GCAAATGGGC GGTAGGCGTG     660

TACGGTGGGA GGTCTATATA AGCAGAGCTC GTTTAGTGAA CCGTCAGATC GCCTGGAGAC     720

GCCATCCACG CTGTTTTGAC CTCCATAGAA GACACCGGGA CCGATCCAGC CTCCGGACTC     780

TAGAGGATCC GGTACTCGAG GAACTGAAAA ACCAGAAAGT TAACTGGTAA GTTTAGTCTT     840

TTTGTCTTTT ATTTCAGGTC CCGGATCCGG TGGTGGTGCA AATCAAAGAA CTGCTCCTCA     900

GTGGATGTTG CCTTTACTTC TAGGCCTGTA CGGAAGTGTT ACTTCTGCTC TAAAAGCTGC     960

GGAATTGTAC CCGCGGCCGC CGCCACC ATG GTG CCC AAG AAG AAG AGG AAG        1011
                                Met Val Pro Lys Lys Lys Arg Lys
```

```
                              1               5
GTG ATG AGC AAG GGC GAG GAA CTG TTC ACT GGC GTG GTC CCA ATT CTC    1059
Val Met Ser Lys Gly Glu Glu Leu Phe Thr Gly Val Val Pro Ile Leu
     10              15                  20

GTG GAA CTG GAT GGC GAT GTG AAT GGG CAC AAA TTT TCT GTC AGC GGA    1107
Val Glu Leu Asp Gly Asp Val Asn Gly His Lys Phe Ser Val Ser Gly
 25              30                  35                  40

GAG GGT GAA GGT GAT GCC ACA TAC GGA AAG CTC ACC CTG AAA TTC ATC    1155
Glu Gly Glu Gly Asp Ala Thr Tyr Gly Lys Leu Thr Leu Lys Phe Ile
                 45                  50                  55

TGC ACC ACT GGA AAG CTC CCT GTG CCA TGG CCA ACA CTG GTC ACT ACC    1203
Cys Thr Thr Gly Lys Leu Pro Val Pro Trp Pro Thr Leu Val Thr Thr
             60                  65                  70

CTG ACC TAT GGC GTG CAG TGC TTT TCC AGA TAC CCA GAC CAT ATG AAG    1251
Leu Thr Tyr Gly Val Gln Cys Phe Ser Arg Tyr Pro Asp His Met Lys
         75                  80                  85

CAG CAT GAC TTT TTC AAG AGC GCC ATG CCC GAG GGC TAT GTG CAG GAG    1299
Gln His Asp Phe Phe Lys Ser Ala Met Pro Glu Gly Tyr Val Gln Glu
     90                  95                 100

AGA ACC ATC TTT TTC AAA GAT GAC GGG AAC TAC AAG ACC CGC GCT GAA    1347
Arg Thr Ile Phe Phe Lys Asp Asp Gly Asn Tyr Lys Thr Arg Ala Glu
105                 110                 115                 120

GTC AAG TTC GAA GGT GAC ACC CTG GTG AAT AGA ATC GAG CTG AAG GGC    1395
Val Lys Phe Glu Gly Asp Thr Leu Val Asn Arg Ile Glu Leu Lys Gly
                125                 130                 135

ATT GAC TTT AAG GAG GAT GGA AAC ATT CTC GGC CAC AAG CTG GAA TAC    1443
Ile Asp Phe Lys Glu Asp Gly Asn Ile Leu Gly His Lys Leu Glu Tyr
            140                 145                 150

AAC TAT AAC TCC CAC AAT GTG TAC ATC ATG GCC GAC AAG CAA AAG AAT    1491
Asn Tyr Asn Ser His Asn Val Tyr Ile Met Ala Asp Lys Gln Lys Asn
        155                 160                 165

GGC ATC AAG GTC AAC TTC AAG ATC AGA CAC AAC ATT GAG GAT GGA TCC    1539
Gly Ile Lys Val Asn Phe Lys Ile Arg His Asn Ile Glu Asp Gly Ser
    170                 175                 180

GTG CAG CTG GCC GAC CAT TAT CAA CAG AAC ACT CCA ATC GGC GAC GGC    1587
Val Gln Leu Ala Asp His Tyr Gln Gln Asn Thr Pro Ile Gly Asp Gly
185                 190                 195                 200

CCT GTG CTC CTC CCA GAC AAC CAT TAC CTG TCC ACC CAG TCT GCC CTG    1635
Pro Val Leu Leu Pro Asp Asn His Tyr Leu Ser Thr Gln Ser Ala Leu
                205                 210                 215

TCT AAA GAT CCC AAC GAA AAG AGA GAC CAC ATG GTC CTG CTG GAG TTT    1683
Ser Lys Asp Pro Asn Glu Lys Arg Asp His Met Val Leu Leu Glu Phe
            220                 225                 230

GTG ACC GCT GCT GGG ATC ACA CAT GGC ATG GAC GAG CTG TAC AAG        1728
Val Thr Ala Ala Gly Ile Thr His Gly Met Asp Glu Leu Tyr Lys
        235                 240                 245

TGAGCGGCCG CGGGGATCCA GACATGATAA GATACATTGA TGAGTTTGGA CAAACCACAA   1788

CTAGAATGCA GTGAAAAAAA TGCTTTATTT GTGAAATTTG TGATGCTATT GCTTTATTTG   1848

TAACCATTAT AAGCTGCAAT AAACAAGTTA ACAACAACAA TTGCATTCAT TTTATGTTTC   1908

AGGTTCAGGG GGAGGTGTGG GAGGTTTTTT AGTCGACCTC GAGCAGTGTG GTTTTGCAAG   1968

AGGAAGCAAA AAGCCTCTCC ACCCAGGCCT GGAATGTTTC CACCCAAGTC GAAGGCAGTG   2028

TGGTTTTGCA AGAGGAAGCA AAAAGCCTCT CCACCCAGGC CTGGAATGTT TCCACCCAAT   2088

GTCGAGCAAC CCCGCCCAGC GTCTTGTCAT TGGCGAATTC GAACACGCAG ATGCAGTCGG   2148

GGCGGCGCGG TCCCAGGTCC ACTTCGCATA TTAAGGTGAC GCGTGTGGCC TCGAACACCG   2208

AGCGACCCTG CAGCCAATAT GGGATCGGCC ATTGAACAAG ATGGATTGCA CGCAGGTTCT   2268
```

```
CCGGCCGCTT GGGTGGAGAG GCTATTCGGC TATGACTGGG CACAACAGAC AATCGGCTGC   2328

TCTGATGCCG CCGTGTTCCG GCTGTCAGCG CAGGGGCGCC CGGTTCTTTT TGTCAAGACC   2388

GACCTGTCCG GTGCCCTGAA TGAACTGCAG GACGAGGCAG CGCGGCTATC GTGGCTGGCC   2448

ACGACGGGCG TTCCTTGCGC AGCTGTGCTC GACGTTGTCA CTGAAGCGGG AAGGGACTGG   2508

CTGCTATTGG GCGAAGTGCC GGGGCAGGAT CTCCTGTCAT CTCACCTTGC TCCTGCCGAG   2568

AAAGTATCCA TCATGGCTGA TGCAATGCGG CGGCTGCATA CGCTTGATCC GGCTACCTGC   2628

CCATTCGACC ACCAAGCGAA ACATCGCATC GAGCGAGCAC GTACTCGGAT GGAAGCCGGT   2688

CTTGTCGATC AGGATGATCT GGACGAAGAG CATCAGGGGC TCGCGCCAGC CGAACTGTTC   2748

GCCAGGCTCA AGGCGCGCAT GCCCGACGGC GAGGATCTCG TCGTGACCCA TGGCGATGCC   2808

TGCTTGCCGA ATATCATGGT GGAAAATGGC CGCTTTTCTG GATTCATCGA CTGTGGCCGG   2868

CTGGGTGTGG CGGACCGCTA TCAGGACATA GCGTTGGCTA CCCGTGATAT TGCTGAAGAG   2928

CTTGGCGGCG AATGGGCTGA CCGCTTCCTC GTGCTTTACG GTATCGCCGC TCCCGATTCG   2988

CAGCGCATCG CCTTCTATCG CCTTCTTGAC GAGTTCTTCT GAGGGGATCC GTCGACTAGA   3048

GCTCGCTGAT CAGCCTCGAC TGTGCCTTCT AGTTGCCAGC CATCTGTTGT TTGCCCCTCC   3108

CCCGTGCCTT CCTTGACCCT GGAAGGTGCC ACTCCCACTG TCCTTTCCTA ATAAAATGAG   3168

GAAATTGCAT CGCATTGTCT GAGTAGGTGT CATTCTATTC TGGGGGGTGG GGTGGGGCAG   3228

GACAGCAAGG GGGAGGATTG GGAAGACAAT AGCAGGCATG CTGGGGAGAG ATCTAGGAAC   3288

CCCTAGTGAT GGAGTTGGCC ACTCCCTCTC TGCGCGCTCG CTCGCTCACT GAGGCCGCCC   3348

GGGCAAAGCC CGGGCGTCGG GCGACCTTTG GTCGCCCGGC CTCAGTGAGC GAGCGAGCGC   3408

GCAGAGAGGG AGTGGCCAAC CCCCCCCCCC CCCCCCCTGC AGCCCTGCAT TAATGAATCG   3468

GCCAACGCGC GGGGAGAGGC GGTTTGCGTA TTGGGCGCTC TTCCGCTTCC TCGCTCACTG   3528

ACTCGCTGCG CTCGGTCGTT CGGCTGCGGC GAGCGGTATC AGCTCACTCA AAGGCGGTAA   3588

TACGGTTATC CACAGAATCA GGGGATAACG CAGGAAAGAA CATGTGAGCA AAAGGCCAGC   3648

AAAAGGCCAG GAACCGTAAA AAGGCCGCGT TGCTGGCGTT TTTCCATAGG CTCCGCCCCC   3708

CTGACGAGCA TCACAAAAAT CGACGCTCAA GTCAGAGGTG GCGAAACCCG ACAGGACTAT   3768

AAAGATACCA GGCGTTTCCC CCTGGAAGCT CCCTCGTGCG CTCTCCTGTT CCGACCCTGC   3828

CGCTTACCGG ATACCTGTCC GCCTTTCTCC CTTCGGGAAG CGTGGCGCTT TCTCAATGCT   3888

CACGCTGTAG GTATCTCAGT TCGGTGTAGG TCGTTCGCTC CAAGCTGGGC TGTGTGCACG   3948

AACCCCCCGT TCAGCCCGAC CGCTGCGCCT TATCCGGTAA CTATCGTCTT GAGTCCAACC   4008

CGGTAAGACA CGACTTATCG CCACTGGCAG CAGCCACTGG TAACAGGATT AGCAGAGCGA   4068

GGTATGTAGG CGGTGCTACA GAGTTCTTGA AGTGGTGGCC TAACTACGGC TACACTAGAA   4128

GGACAGTATT TGGTATCTGC GCTCTGCTGA AGCCAGTTAC CTTCGGAAAA AGAGTTGGTA   4188

GCTCTTGATC CGGCAAACAA ACCACCGCTG GTAGCGGTGG TTTTTTTGTT TGCAAGCAGC   4248

AGATTACGCG CAGAAAAAAA GGATCTCAAG AAGATCCTTT GATCTTTTCT ACGGGGTCTG   4308

ACGCTCAGTG GAACGAAAAC TCACGTTAAG GGATTTTGGT CATGAGATTA TCAAAAAGGA   4368

TCTTCACCTA GATCCTTTTA AATTAAAAAT GAAGTTTTAA ATCAATCTAA AGTATATATG   4428

AGTAAACTTG GTCTGACAGT TACCAATGCT TAATCAGTGA GGCACCTATC TCAGCGATCT   4488

GTCTATTTCG TTCATCCATA GTTGCCTGAC TCCCCGTCGT GTAGATAACT ACGATACGGG   4548

AGGGCTTACC ATCTGGCCCC AGTGCTGCAA TGATACCGCG AGACCCACGC TCACCGGCTC   4608

CAGATTTATC AGCAATAAAC CAGCCAGCCG GAAGGGCCGA GCGCAGAAGT GGTCCTGCAA   4668
```

-continued

```
CTTTATCCGC CTCCATCCAG TCTATTAATT GTTGCCGGGA AGCTAGAGTA AGTAGTTCGC    4728

CAGTTAATAG TTTGCGCAAC GTTGTTGCCA TTGCTACAGG CATCGTGGTG TCACGCTCGT    4788

CGTTTGGTAT GGCTTCATTC AGCTCCGGTT CCCAACGATC AAGGCGAGTT ACATGATCCC    4848

CCATGTTGTG CAAAAAAGCG GTTAGCTCCT TCGGTCCTCC GATCGTTGTC AGAAGTAAGT    4908

TGGCCGCAGT GTTATCACTC ATGGTTATGG CAGCACTGCA TAATTCTCTT ACTGTCATGC    4968

CATCCGTAAG ATGCTTTTCT GTGACTGGTG AGTACTCAAC CAAGTCATTC TGAGAATAGT    5028

GTATGCGGCG ACCGAGTTGC TCTTGCCCGG CGTCAATACG GGATAATACC GCGCCACATA    5088

GCAGAACTTT AAAAGTGCTC ATCATTGGAA AACGTTCTTC GGGGCGAAAA CTCTCAAGGA    5148

TCTTACCGCT GTTGAGATCC AGTTCGATGT AACCCACTCG TGCACCCAAC TGATCTTCAG    5208

CATCTTTTAC TTTCACCAGC GTTTCTGGGT GAGCAAAAAC AGGAAGGCAA AATGCCGCAA    5268

AAAAGGGAAT AAGGGCGACA CGGAAATGTT GAATACTCAT ACTCTTCCTT TTTCAATATT    5328

ATTGAAGCAT TTATCAGGGT TATTGTCTCA TGAGCGGATA CATATTTGAA TGTATTTAGA    5388

AAAATAAACA AATAGGGGTT CCGCGCACAT TTCCCCGAAA AGTGCCACCT GACGTCTAAG    5448

AAACCATTAT TATCATGACA TTAACCTATA AAAATAGGCG TATCACGAGG CCCTTTCGTC    5508

TCGCGCGTTT CGGTGATGAC GGTGAAAACC TCTGACACAT GCAGCTCCCG GAGACGGTCA    5568

CAGCTTGTCT GTAAGCGGAT GCCGGGAGCA GACAAGCCCG TCAGGGCGCG TCAGCGGGTG    5628

TTGGCGGGTG TCGGGCTGG CTTAACTATG CGGCATCAGA GCAGATTGTA CTGAGAGTGC     5688

ACCATATGCG GTGTGAAATA CCGCACAGAT GCGTAAGGAG AAAATACCGC ATCAGGAAAT    5748

TGTAAACGTT AATATTTTGT TAAAATTCGC GTTAAATTTT TGTTAAATCA GCTCATTTTT    5808

TAACCAATAG GCCGAAATCG GCAAAATCCC TTATAAATCA AAAGAATAGA CCGAGATAGG    5868

GTTGAGTGTT GTTCCAGTTT GGAACAAGAG TCCACTATTA AGAACGTGG ACTCCAACGT     5928

CAAAGGGCGA AAACCGTCT ATCAGGGCGA TGGCCCACTA CGTGAACCAT CACCCTAATC     5988

AAGTTTTTTG GGGTCGAGGT GCCGTAAAGC ACTAAATCGG AACCCTAAAG GGAGCCCCCG    6048

ATTTAGAGCT TGACGGGGAA AGCCGGCGAA CGTGGCGAGA AAGGAAGGGA AGAAAGCGAA    6108

AGGAGCGGGC GCTAGGGCGC TGGCAAGTGT AGCGGTCACG CTGCGCGTAA CCACCACACC    6168

CGCCGCGCTT AATGCGCCGC TACAGGGCGC GTCGCGCCAT TCGCCATTCA GGCTACGCAA    6228

CTGTTGGGAA GGGCGATCGG TGCGGGCCTC TTCGCTATTA CGCCAGGCTG CA            6280
```

(2) INFORMATION FOR SEQ ID NO:18:

(i) SEQUENCE CHARACTERISTICS:
        (A) LENGTH: 247 amino acids
        (B) TYPE: amino acid
        (D) TOPOLOGY: linear (ii) MOLECULE TYPE: protein (xi) SEQUENCE DESCRIPTION: SEQ ID NO:18:

```
Met Val Pro Lys Lys Arg Lys Val Met Ser Lys Gly Glu Glu Leu
 1               5                  10                  15

Phe Thr Gly Val Val Pro Ile Leu Val Glu Leu Asp Gly Asp Val Asn
                20                  25                  30

Gly His Lys Phe Ser Val Ser Gly Glu Gly Glu Gly Asp Ala Thr Tyr
            35                  40                  45

Gly Lys Leu Thr Leu Lys Phe Ile Cys Thr Thr Gly Lys Leu Pro Val
        50                  55                  60

Pro Trp Pro Thr Leu Val Thr Thr Leu Thr Tyr Gly Val Gln Cys Phe
65                  70                  75                  80
```

```
Ser Arg Tyr Pro Asp His Met Lys Gln His Asp Phe Phe Lys Ser Ala
             85                  90                  95

Met Pro Glu Gly Tyr Val Gln Glu Arg Thr Ile Phe Phe Lys Asp Asp
        100                 105                 110

Gly Asn Tyr Lys Thr Arg Ala Glu Val Lys Phe Glu Gly Asp Thr Leu
        115                 120                 125

Val Asn Arg Ile Glu Leu Lys Gly Ile Asp Phe Lys Glu Asp Gly Asn
    130                 135                 140

Ile Leu Gly His Lys Leu Glu Tyr Asn Tyr Asn Ser His Asn Val Tyr
145                 150                 155                 160

Ile Met Ala Asp Lys Gln Lys Asn Gly Ile Lys Val Asn Phe Lys Ile
                165                 170                 175

Arg His Asn Ile Glu Asp Gly Ser Val Gln Leu Ala Asp His Tyr Gln
            180                 185                 190

Gln Asn Thr Pro Ile Gly Asp Gly Pro Val Leu Leu Pro Asp Asn His
        195                 200                 205

Tyr Leu Ser Thr Gln Ser Ala Leu Ser Lys Asp Pro Asn Glu Lys Arg
    210                 215                 220

Asp His Met Val Leu Leu Glu Phe Val Thr Ala Ala Gly Ile Thr His
225                 230                 235                 240

Gly Met Asp Glu Leu Tyr Lys
                245
```

(2) INFORMATION FOR SEQ ID NO:19:

(i) SEQUENCE CHARACTERISTICS:
        (A) LENGTH: 6280 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 988..1728

(xi) SEQUENCE DESCRIPTION: SEQ ID NO:19:

```
GGGGGGGGGG GGGGGGGGTT GGCCACTCCC TCTCTGCGCG CTCGCTCGCT CACTGAGGCC    60

GGGCGACCAA AGGTCGCCCG ACGCCCGGGC TTTGCCCGGG CGGCCTCAGT GAGCGAGCGA   120

GCGCGCAGAG AGGGAGTGGC CAACTCCATC ACTAGGGGTT CCTAGATCTG AATTCGGTAC   180

CCGTTACATA ACTTACGGTA AATGGCCCGC CTGGCTGACC GCCCAACGAC CCCCGCCCAT   240

TGACGTCAAT AATGACGTAT GTTCCCATAG TAACGCCAAT AGGGACTTTC CATTGACGTC   300

AATGGGTGGA GTATTTACGG TAAACTGCCC ACTTGGCAGT ACATCAAGTG TATCATATGC   360

CAAGTACGCC CCCTATTGAC GTCAATGACG GTAAATGGCC CGCCTGGCAT TATGCCCAGT   420

ACATGACCTT ATGGGACTTT CCTACTTGGC AGTACATCTA CGTATTAGTC ATCGCTATTA   480

CCATGGTGAT GCGGTTTTGG CAGTACATCA ATGGGCGTGG ATAGCGGTTT GACTCACGGG   540

GATTTCCAAG TCTCCACCCC ATTGACGTCA ATGGGAGTTT GTTTTGGCAC CAAAATCAAC   600

GGGACTTTCC AAAATGTCGT AACAACTCCG CCCCATTGAC GCAAATGGGC GGTAGGCGTG   660

TACGGTGGGA GGTCTATATA AGCAGAGCTC GTTTAGTGAA CCGTCAGATC GCCTGGAGAC   720

GCCATCCACG CTGTTTTGAC CTCCATAGAA GACACCGGGA CCGATCCAGC CTCCGGACTC   780

TAGAGGATCC GGTACTCGAG GAACTGAAAA ACCAGAAAGT TAACTGGTAA GTTTAGTCTT   840

TTTGTCTTTT ATTTCAGGTC CCGGATCCGG TGGTGGTGCA AATCAAAGAA CTGCTCCTCA   900

GTGGATGTTG CCTTTACTTC TAGGCCTGTA CGGAAGTGTT ACTTCTGCTC TAAAAGCTGC   960
```

```
GGAATTGTAC CCGCGGCCGC CGCCACC ATG GTG CCC AAG AAG AAG AGG AAG        1011
                               Met Val Pro Lys Lys Lys Arg Lys
                                1               5

GTG ATG AGC AAG GGC GAG GAA CTG TTC ACT GGC GTG GTC CCA ATT CTC      1059
Val Met Ser Lys Gly Glu Glu Leu Phe Thr Gly Val Val Pro Ile Leu
    10              15                  20

GTG GAA CTG GAT GGC GAT GTG AAT GGG CAC AAA TTT TCT GTC AGC GGA      1107
Val Glu Leu Asp Gly Asp Val Asn Gly His Lys Phe Ser Val Ser Gly
25              30                  35                  40

GAG GGT GAA GGT GAT GCC ACA TAC GGA AAG CTC ACC CTG AAA TTC ATC      1155
Glu Gly Glu Gly Asp Ala Thr Tyr Gly Lys Leu Thr Leu Lys Phe Ile
                45                  50                  55

TGC ACC ACT GGA AAG CTC CCT GTG CCA TGG CCA ACA CTG GTC ACT ACC      1203
Cys Thr Thr Gly Lys Leu Pro Val Pro Trp Pro Thr Leu Val Thr Thr
            60                  65                  70

TTC TCT CAT GGC GTG CAG TGC TTT TCC AGA TAC CCA GAC CAT ATG AAG      1251
Phe Ser His Gly Val Gln Cys Phe Ser Arg Tyr Pro Asp His Met Lys
        75                  80                  85

CAG CAT GAC TTT TTC AAG AGC GCC ATG CCC GAG GGC TAT GTG CAG GAG      1299
Gln His Asp Phe Phe Lys Ser Ala Met Pro Glu Gly Tyr Val Gln Glu
    90                  95                  100

AGA ACC ATC TTT TTC AAA GAT GAC GGG AAC TAC AAG ACC CGC GCT GAA      1347
Arg Thr Ile Phe Phe Lys Asp Asp Gly Asn Tyr Lys Thr Arg Ala Glu
105                 110                 115                 120

GTC AAG TTC GAA GGT GAC ACC CTG GTG AAT AGA ATC GAG CTG AAG GGC      1395
Val Lys Phe Glu Gly Asp Thr Leu Val Asn Arg Ile Glu Leu Lys Gly
                125                 130                 135

ATT GAC TTT AAG GAG GAT GGA AAC ATT CTC GGC CAC AAG CTG GAA TAC      1443
Ile Asp Phe Lys Glu Asp Gly Asn Ile Leu Gly His Lys Leu Glu Tyr
            140                 145                 150

AAC TTC AAC TCC CAC AAT GTG TAC ATC ATG GCC GAC AAG CAA AAG AAT      1491
Asn Phe Asn Ser His Asn Val Tyr Ile Met Ala Asp Lys Gln Lys Asn
        155                 160                 165

GGC ATC AAG GTC AAC TTC AAG ATC AGA CAC AAC ATT GAG GAT GGA TCC      1539
Gly Ile Lys Val Asn Phe Lys Ile Arg His Asn Ile Glu Asp Gly Ser
    170                 175                 180

GTG CAG CTG GCC GAC CAT TAT CAA CAG AAC ACT CCA ATC GGC GAC GGC      1587
Val Gln Leu Ala Asp His Tyr Gln Gln Asn Thr Pro Ile Gly Asp Gly
185                 190                 195                 200

CCT GTG CTC CTC CCA GAC AAC CAT TAC CTG TCC ACC CAG TCT GCC CTG      1635
Pro Val Leu Leu Pro Asp Asn His Tyr Leu Ser Thr Gln Ser Ala Leu
                205                 210                 215

TCT AAA GAT CCC AAC GAA AAG AGA GAC CAC ATG GTC CTG CTG GAG TTT      1683
Ser Lys Asp Pro Asn Glu Lys Arg Asp His Met Val Leu Leu Glu Phe
            220                 225                 230

GTG ACC GCT GCT GGG ATC ACA CAT GGC ATG GAC GAG CTG TAC AAG          1728
Val Thr Ala Ala Gly Ile Thr His Gly Met Asp Glu Leu Tyr Lys
        235                 240                 245

TGAGCGGCCG CGGGGATCCA GACATGATAA GATACATTGA TGAGTTTGGA CAAACCACAA    1788

CTAGAATGCA GTGAAAAAAA TGCTTTATTT GTGAAATTTG TGATGCTATT GCTTTATTTG    1848

TAACCATTAT AAGCTGCAAT AAACAAGTTA ACAACAACAA TTGCATTCAT TTATGTTTC     1908

AGGTTCAGGG GGAGGTGTGG GAGGTTTTTT AGTCGACCTC GAGCAGTGTG GTTTTGCAAG    1968

AGGAAGCAAA AAGCCTCTCC ACCCAGGCCT GGAATGTTTC CACCCAAGTC GAAGGCAGTG    2028

TGGTTTTGCA AGAGGAAGCA AAAAGCCTCT CCACCCAGGC CTGGAATGTT TCCACCCAAT    2088

GTCGAGCAAC CCCGCCCAGC GTCTTGTCAT TGGCGAATTC GAACACGCAG ATGCAGTCGG    2148

GGCGGCGCGG TCCCAGGTCC ACTTCGCATA TTAAGGTGAC GCGTGTGGCC TCGAACACCG    2208
```

```
AGCGACCCTG CAGCCAATAT GGGATCGGCC ATTGAACAAG ATGGATTGCA CGCAGGTTCT    2268

CCGGCCGCTT GGGTGGAGAG GCTATTCGGC TATGACTGGG CACAACAGAC AATCGGCTGC    2328

TCTGATGCCG CCGTGTTCCG GCTGTCAGCG CAGGGGCGCC CGGTTCTTTT TGTCAAGACC    2388

GACCTGTCCG GTGCCCTGAA TGAACTGCAG GACGAGGCAG CGCGGCTATC GTGGCTGGCC    2448

ACGACGGGCG TTCCTTGCGC AGCTGTGCTC GACGTTGTCA CTGAAGCGGG AAGGGACTGG    2508

CTGCTATTGG GCGAAGTGCC GGGGCAGGAT CTCCTGTCAT CTCACCTTGC TCCTGCCGAG    2568

AAAGTATCCA TCATGGCTGA TGCAATGCGG CGGCTGCATA CGCTTGATCC GGCTACCTGC    2628

CCATTCGACC ACCAAGCGAA ACATCGCATC GAGCGAGCAC GTACTCGGAT GGAAGCCGGT    2688

CTTGTCGATC AGGATGATCT GGACGAAGAG CATCAGGGGC TCGCGCCAGC CGAACTGTTC    2748

GCCAGGCTCA AGGCGCGCAT GCCCGACGGC GAGGATCTCG TCGTGACCCA TGGCGATGCC    2808

TGCTTGCCGA ATATCATGGT GGAAAATGGC CGCTTTTCTG GATTCATCGA CTGTGGCCGG    2868

CTGGGTGTGG CGGACCGCTA TCAGGACATA GCGTTGGCTA CCCGTGATAT TGCTGAAGAG    2928

CTTGGCGGCG AATGGGCTGA CCGCTTCCTC GTGCTTTACG GTATCGCCGC TCCCGATTCG    2988

CAGCGCATCG CCTTCTATCG CCTTCTTGAC GAGTTCTTCT GAGGGGATCC GTCGACTAGA    3048

GCTCGCTGAT CAGCCTCGAC TGTGCCTTCT AGTTGCCAGC CATCTGTTGT TTGCCCCTCC    3108

CCCGTGCCTT CCTTGACCCT GGAAGGTGCC ACTCCCACTG TCCTTTCCTA ATAAAATGAG    3168

GAAATTGCAT CGCATTGTCT GAGTAGGTGT CATTCTATTC TGGGGGGTGG GGTGGGGCAG    3228

GACAGCAAGG GGGAGGATTG GGAAGACAAT AGCAGGCATG CTGGGGAGAG ATCTAGGAAC    3288

CCCTAGTGAT GGAGTTGGCC ACTCCCTCTC TGCGCGCTCG CTCGCTCACT GAGGCCGCCC    3348

GGGCAAAGCC CGGGCGTCGG GCGACCTTTG GTCGCCCGGC CTCAGTGAGC GAGCGAGCGC    3408

GCAGAGAGGG AGTGGCCAAC CCCCCCCCCC CCCCCCCTGC AGCCCTGCAT TAATGAATCG    3468

GCCAACGCGC GGGGAGAGGC GGTTTGCGTA TTGGGCGCTC TTCCGCTTCC TCGCTCACTG    3528

ACTCGCTGCG CTCGGTCGTT CGGCTGCGGC GAGCGGTATC AGCTCACTCA AAGGCGGTAA    3588

TACGGTTATC CACAGAATCA GGGGATAACG CAGGAAAGAA CATGTGAGCA AAAGGCCAGC    3648

AAAAGGCCAG GAACCGTAAA AAGGCCGCGT TGCTGGCGTT TTTCCATAGG CTCCGCCCCC    3708

CTGACGAGCA TCACAAAAAT CGACGCTCAA GTCAGAGGTG GCGAAACCCG ACAGGACTAT    3768

AAAGATACCA GGCGTTTCCC CCTGGAAGCT CCCTCGTGCG CTCTCCTGTT CCGACCCTGC    3828

CGCTTACCGG ATACCTGTCC GCCTTTCTCC CTTCGGGAAG CGTGGCGCTT TCTCAATGCT    3888

CACGCTGTAG GTATCTCAGT TCGGTGTAGG TCGTTCGCTC CAAGCTGGGC TGTGTGCACG    3948

AACCCCCCGT TCAGCCCGAC CGCTGCGCCT TATCCGGTAA CTATCGTCTT GAGTCCAACC    4008

CGGTAAGACA CGACTTATCG CCACTGGCAG CAGCCACTGG TAACAGGATT AGCAGAGCGA    4068

GGTATGTAGG CGGTGCTACA GAGTTCTTGA AGTGGTGGCC TAACTACGGC TACACTAGAA    4128

GGACAGTATT TGGTATCTGC GCTCTGCTGA AGCCAGTTAC CTTCGGAAAA AGAGTTGGTA    4188

GCTCTTGATC CGGCAAACAA ACCACCGCTG GTAGCGGTGG TTTTTTTGTT TGCAAGCAGC    4248

AGATTACGCG CAGAAAAAAA GGATCTCAAG AAGATCCTTT GATCTTTTCT ACGGGGTCTG    4308

ACGCTCAGTG GAACGAAAAC TCACGTTAAG GGATTTTGGT CATGAGATTA TCAAAAAGGA    4368

TCTTCACCTA GATCCTTTTA AATTAAAAAT GAAGTTTTAA ATCAATCTAA AGTATATATG    4428

AGTAAACTTG GTCTGACAGT TACCAATGCT TAATCAGTGA GGCACCTATC TCAGCGATCT    4488

GTCTATTTCG TTCATCCATA GTTGCCTGAC TCCCCGTCGT GTAGATAACT ACGATACGGG    4548

AGGGCTTACC ATCTGGCCCC AGTGCTGCAA TGATACCGCG AGACCCACGC TCACCGGCTC    4608
```

-continued

```
CAGATTTATC AGCAATAAAC CAGCCAGCCG GAAGGGCCGA GCGCAGAAGT GGTCCTGCAA    4668

CTTTATCCGC CTCCATCCAG TCTATTAATT GTTGCCGGGA AGCTAGAGTA AGTAGTTCGC    4728

CAGTTAATAG TTTGCGCAAC GTTGTTGCCA TTGCTACAGG CATCGTGGTG TCACGCTCGT    4788

CGTTTGGTAT GGCTTCATTC AGCTCCGGTT CCCAACGATC AAGGCGAGTT ACATGATCCC    4848

CCATGTTGTG CAAAAAGCG GTTAGCTCCT TCGGTCCTCC GATCGTTGTC AGAAGTAAGT    4908

TGGCCGCAGT GTTATCACTC ATGGTTATGG CAGCACTGCA TAATTCTCTT ACTGTCATGC    4968

CATCCGTAAG ATGCTTTTCT GTGACTGGTG AGTACTCAAC CAAGTCATTC TGAGAATAGT    5028

GTATGCGGCG ACCGAGTTGC TCTTGCCCGG CGTCAATACG GGATAATACC GCGCCACATA    5088

GCAGAACTTT AAAAGTGCTC ATCATTGGAA AACGTTCTTC GGGGCGAAAA CTCTCAAGGA    5148

TCTTACCGCT GTTGAGATCC AGTTCGATGT AACCCACTCG TGCACCCAAC TGATCTTCAG    5208

CATCTTTTAC TTTCACCAGC GTTTCTGGGT GAGCAAAAAC AGGAAGGCAA AATGCCGCAA    5268

AAAAGGGAAT AAGGGCGACA CGGAAATGTT GAATACTCAT ACTCTTCCTT TTTCAATATT    5328

ATTGAAGCAT TTATCAGGGT TATTGTCTCA TGAGCGGATA CATATTTGAA TGTATTTAGA    5388

AAAATAAACA AATAGGGGTT CCGCGCACAT TTCCCCGAAA AGTGCCACCT GACGTCTAAG    5448

AAACCATTAT TATCATGACA TTAACCTATA AAAATAGGCG TATCACGAGG CCCTTTCGTC    5508

TCGCGCGTTT CGGTGATGAC GGTGAAAACC TCTGACACAT GCAGCTCCCG GAGACGGTCA    5568

CAGCTTGTCT GTAAGCGGAT GCCGGGAGCA GACAAGCCCG TCAGGGCGCG TCAGCGGGTG    5628

TTGGCGGGTG TCGGGCTGG CTTAACTATG CGGCATCAGA GCAGATTGTA CTGAGAGTGC    5688

ACCATATGCG GTGTGAAATA CCGCACAGAT GCGTAAGGAG AAAATACCGC ATCAGGAAAT    5748

TGTAAACGTT AATATTTTGT TAAAATTCGC GTTAAATTTT TGTTAAATCA GCTCATTTTT    5808

TAACCAATAG GCCGAAATCG GCAAAATCCC TTATAAATCA AAAGAATAGA CCGAGATAGG    5868

GTTGAGTGTT GTTCCAGTTT GGAACAAGAG TCCACTATTA AGAACGTGG ACTCCAACGT     5928

CAAAGGGCGA AAAACCGTCT ATCAGGGCGA TGGCCCACTA CGTGAACCAT CACCCTAATC    5988

AAGTTTTTTG GGGTCGAGGT GCCGTAAAGC ACTAAATCGG AACCCTAAAG GGAGCCCCCG    6048

ATTTAGAGCT TGACGGGGAA AGCCGGCGAA CGTGGCGAGA AAGGAAGGGA AGAAAGCGAA    6108

AGGAGCGGGC GCTAGGGCGC TGGCAAGTGT AGCGGTCACG CTGCGCGTAA CCACCACACC    6168

CGCCGCGCTT AATGCGCCGC TACAGGGCGC GTCGCGCCAT TCGCCATTCA GGCTACGCAA    6228

CTGTTGGGAA GGGCGATCGG TGCGGGCCTC TTCGCTATTA CGCCAGGCTG CA            6280
```

(2) INFORMATION FOR SEQ ID NO:20:

(i) SEQUENCE CHARACTERISTICS:
        (A) LENGTH: 247 amino acids
        (B) TYPE: amino acid
        (D) TOPOLOGY: linear (ii) MOLECULE TYPE: protein (xi) SEQUENCE DESCRIPTION: SEQ ID NO:20:

```
Met Val Pro Lys Lys Arg Lys Val Met Ser Lys Gly Glu Glu Leu
 1               5                  10                  15

Phe Thr Gly Val Val Pro Ile Leu Val Glu Leu Asp Gly Asp Val Asn
                20                  25                  30

Gly His Lys Phe Ser Val Ser Gly Glu Gly Glu Gly Asp Ala Thr Tyr
         35                  40                  45

Gly Lys Leu Thr Leu Lys Phe Ile Cys Thr Thr Gly Lys Leu Pro Val
     50                  55                  60
```

-continued

```
Pro Trp Pro Thr Leu Val Thr Thr Phe Ser His Gly Val Gln Cys Phe
 65              70              75                  80

Ser Arg Tyr Pro Asp His Met Lys Gln His Asp Phe Phe Lys Ser Ala
             85              90                  95

Met Pro Glu Gly Tyr Val Gln Glu Arg Thr Ile Phe Phe Lys Asp Asp
            100             105             110

Gly Asn Tyr Lys Thr Arg Ala Glu Val Lys Phe Glu Gly Asp Thr Leu
        115             120             125

Val Asn Arg Ile Glu Leu Lys Gly Ile Asp Phe Lys Glu Asp Gly Asn
        130             135             140

Ile Leu Gly His Lys Leu Glu Tyr Asn Phe Asn Ser His Asn Val Tyr
145             150             155             160

Ile Met Ala Asp Lys Gln Lys Asn Gly Ile Lys Val Asn Phe Lys Ile
                165             170             175

Arg His Asn Ile Glu Asp Gly Ser Val Gln Leu Ala Asp His Tyr Gln
            180             185             190

Gln Asn Thr Pro Ile Gly Asp Gly Pro Val Leu Leu Pro Asp Asn His
        195             200             205

Tyr Leu Ser Thr Gln Ser Ala Leu Ser Lys Asp Pro Asn Glu Lys Arg
    210             215             220

Asp His Met Val Leu Leu Glu Phe Val Thr Ala Ala Gly Ile Thr His
225             230             235             240

Gly Met Asp Glu Leu Tyr Lys
                245
```